(12) United States Patent
Mueller et al.

(10) Patent No.: US 9,303,082 B2
(45) Date of Patent: Apr. 5, 2016

(54) IMMUNOGENIC POLYPEPTIDES COMPRISING A SCAFFOLD POLYPEPTIDE AND A L2 POLYPEPTIDE OR A FRAGMENT THEREOF

(75) Inventors: Martin Mueller, Neckargemuend (DE); Ivonne Rubio, Heidelberg (DE); Massimo Tommasino, Charly-Lyon (IT); Simone Ottonello, Parma (IT); Angelo Bolchi, Parma (IT)

(73) Assignee: DKFZ Deutsches Krebsforschungszentrum, Heidelberg (DE)

( * ) Notice: Subject to any disclaimer, the term of this patent is extended or adjusted under 35 U.S.C. 154(b) by 131 days.

(21) Appl. No.: 13/140,793

(22) PCT Filed: Dec. 17, 2009

(86) PCT No.: PCT/EP2009/067422
§ 371 (c)(1),
(2), (4) Date: Aug. 11, 2011

(87) PCT Pub. No.: WO2010/070052
PCT Pub. Date: Jun. 24, 2010

(65) Prior Publication Data
US 2011/0293621 A1    Dec. 1, 2011

(30) Foreign Application Priority Data
Dec. 19, 2008  (EP) .................................. 08172349

(51) Int. Cl.
| | | |
|---|---|---|
| A61K 39/395 | (2006.01) | |
| C07K 16/08 | (2006.01) | |
| A61K 39/12 | (2006.01) | |
| C07K 14/005 | (2006.01) | |
| C12N 7/00 | (2006.01) | |
| A61K 39/385 | (2006.01) | |
| A61K 39/00 | (2006.01) | |

(52) U.S. Cl.
CPC .............. *C07K 16/084* (2013.01); *A61K 39/12* (2013.01); *A61K 39/385* (2013.01); *C07K 14/005* (2013.01); *C12N 7/00* (2013.01); *A61K 2039/505* (2013.01); *A61K 2039/55566* (2013.01); *A61K 2039/6031* (2013.01); *C07K 2317/34* (2013.01); *C07K 2319/35* (2013.01); *C12N 2710/20022* (2013.01); *C12N 2710/20034* (2013.01)

(58) Field of Classification Search
None
See application file for complete search history.

(56) References Cited

U.S. PATENT DOCUMENTS

| | | | |
|---|---|---|---|
| 5,792,455 A | | 8/1998 | Chapman et al. |
| 6,143,524 A | * | 11/2000 | McCoy et al. ............... 435/69.7 |
| 6,551,597 B1 | * | 4/2003 | Harrison et al. ........... 424/204.1 |
| 2008/0127359 A1 | | 5/2008 | Beck et al. |
| 2010/0183648 A1 | | 7/2010 | Kanda et al. |

FOREIGN PATENT DOCUMENTS

| | | |
|---|---|---|
| WO | WO 02/70004 | 9/2002 |
| WO | WO 2008/140474 A1 | 11/2008 |
| WO | WO 2009/001867 A1 | 12/2008 |

OTHER PUBLICATIONS

Alphs et al., "Protection against heterologous human papillomavirus challenge by a synthetic lipopeptide vaccine containing a broadly cross-neutralizing epitope of L2," *Proc Natl Acad Sci USA*, pp. 5850-5855, vol. 105 (2008).
Arnér et al., "Physiological functions of thioredoxin and thioredoxin reductase," *European Journal of Biochemistry*, pp. 6102-6109, vol. 267, No. 20 (2000).
Attanasio, "Idiotypic Cascades Associated with the CD4-HIV gp120 Interational: Principles for Idiotype-Based Vaccines," *Int Rev Immunol.*, pp. 109-19, vol. 7(1), (1990).
Dalgleish, "An anti-idiotype vaccine for AIDS based on the HIV receptor," *Ann. 1st Super. Sanita*, pp. 27-31, vol. 27(1), (1991).
De Jong et al., "Enhancement of human papillomavirus (HPV) type 16 E6 and E7-specific T-cell immunity in healthy volunteers through vaccination with TA-CIN, an HPV16 L2E7E6 fusion protein vaccine," *Vaccine*, vol. 20(29-30), pp. 3456-3464 (2002).
Gambhira, et al., "A protective and broadly cross-neutralizing epitope of human papillomavirus L2," *J. Virol.*, pp. 13927-13931, vol. 81, (2007).
Giroglou et al., "Immunological analyses of human papillomavirus capsids," *Vaccine*, pp. 1783-1793, vol. 19 (2001).
Huh et al., "The future of vaccines for cervical cancer," *Gynecol Oncol*, pp. S48-56, vol. 109 (2008).
Kawana et al., "Nasal immunization of mice with peptide having a cross-neutralization epitope on minor capsid protein L2 of human papillomavirus type 16 elicit systemic and mucosal antibodies," *Vaccine*, pp. 1496-1502, vol. 19 (2001).

(Continued)

*Primary Examiner* — Yunsoo Kim
(74) *Attorney, Agent, or Firm* — Foley & Lardner LLP

(57) ABSTRACT

The present invention relates to an immunogenic polypeptide comprising a) a scaffold polypeptide, and b) a L2 polypeptide or a fragment of said L2 polypeptide, wherein said scaffold polypeptide constrains the structure of said L2 polypeptide, or of a fragment of said L2 polypeptide. Moreover, the present invention relates to a vaccine comprising said immunogenic polypeptide. The present invention is also concerned with a method for producing an antibody against human papillomavirus. Also encompassed by the present invention is an antibody obtained by carrying out the said method.

16 Claims, 15 Drawing Sheets

(56) References Cited

OTHER PUBLICATIONS

Figure 1B:
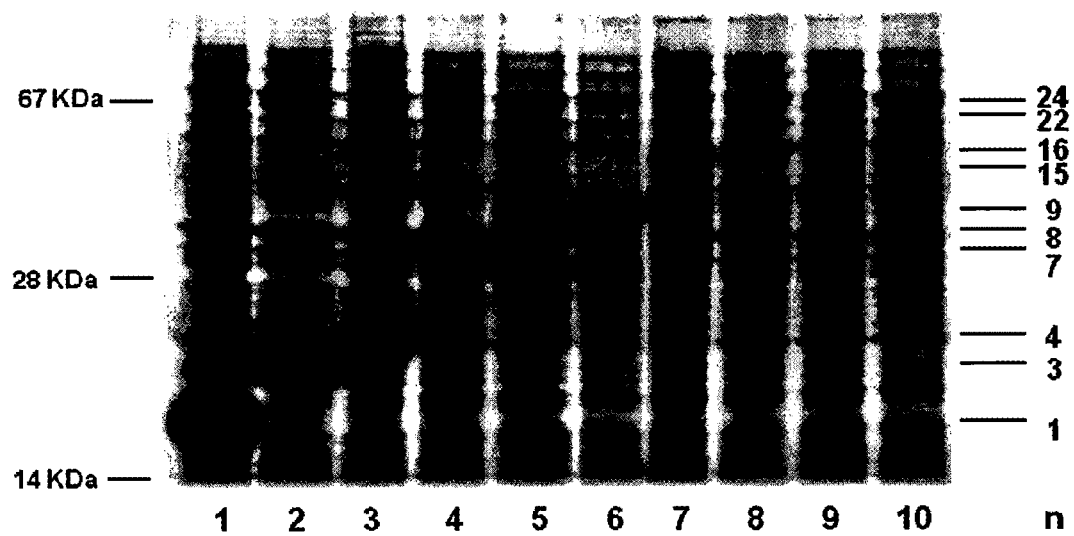
Figure 1C:
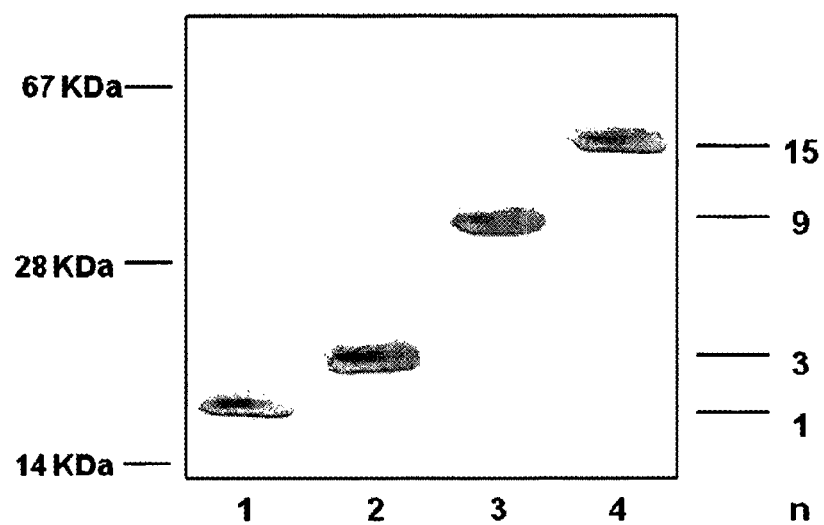
Figure 1D:
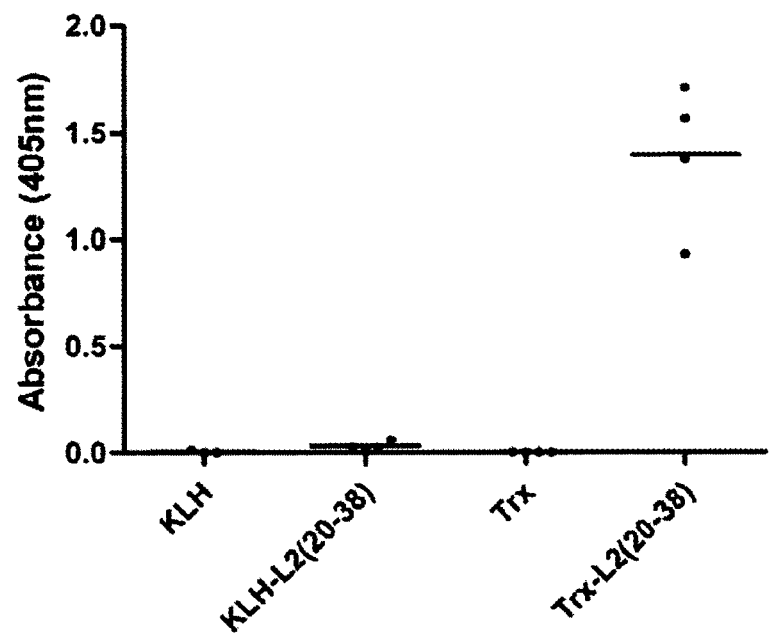
Figure 2:
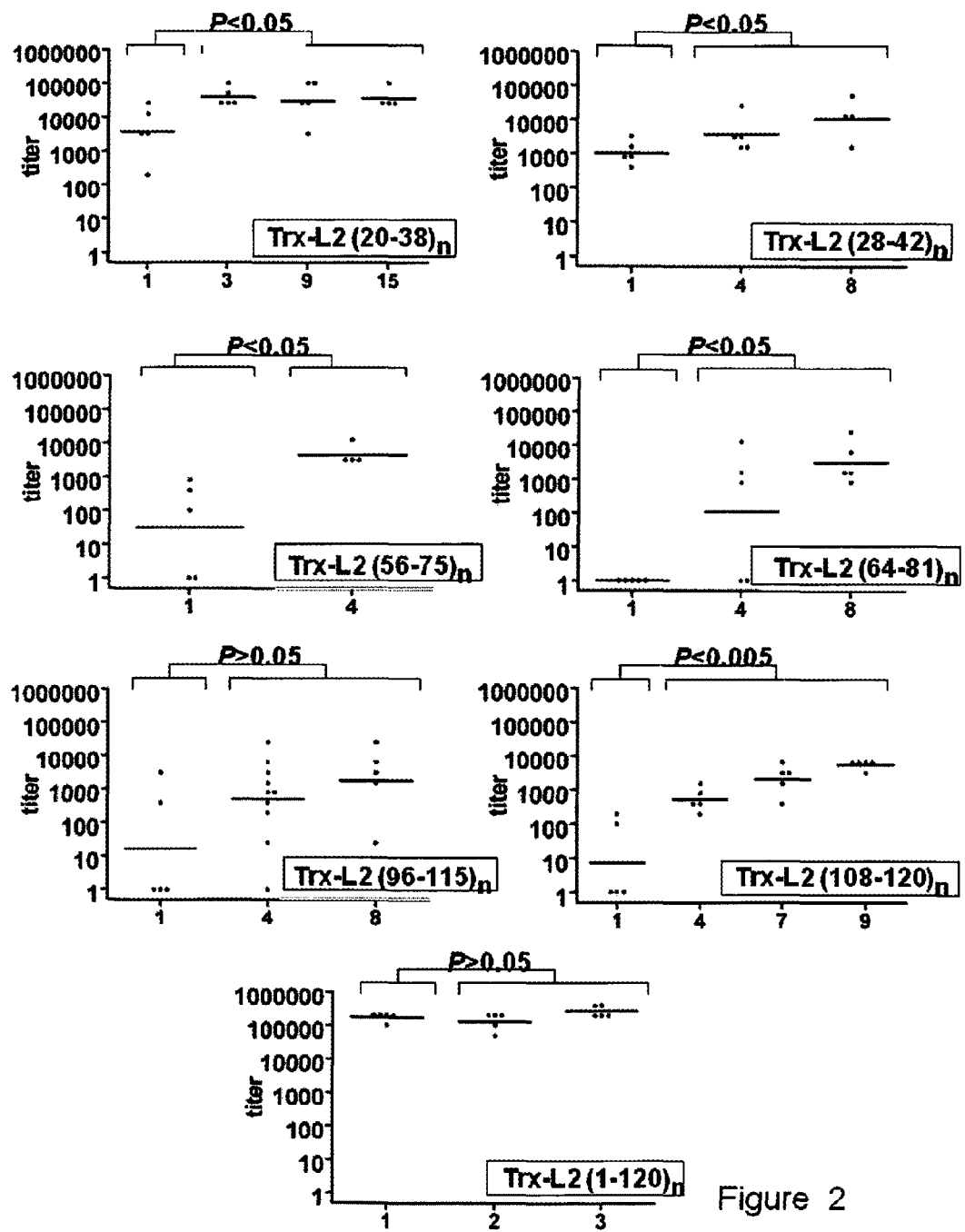

Kondo et al., "Neutralization of HPV16, 18, 31, and 58 pseudovirions with antisera induced by immunizing rabbits with synthetic peptides representing segments of the HPV16 minor capsid protein L2 surface region," *Virology*, Academic Press, Orlando, U.S., pp. 266-272, vol. 358, No. 2 (2007).

Mambetisaeva et al., "Expression of Three Functional Domains of connexin 32 as Thioredoxin Fusion Proteins in *Escherichia coli* and Generation of Antibodies," *Protein Expression and Purification*, Academic Press, San Diego, CA, pp. 26-34, vol. 11, No. 1 (1997).

Moretto et al., "Conformation-sensitive antibodies against Alzheimer amyloid-beta by immunization with a thioredoxin-constrained B-cell epitope peptide," *J Biol Chem*, pp. 11436-11445, vol. 282 (2007).

Muller et al., "A long way: history of the prophylactic papillomavirus," *Vaccine*, 2007, Dis Markers, pp. 331-336, vol. 23 (2007).

Pastrana et al., "Cross-neutralization of cutaneous and mucosal Papillomavirus types with anti-sera to the amino terminus of L2," *Virology*, pp. 365-372, vol. 337 (2005).

Roden et al., "How will HPV vaccines affect cervical cancer?" *Nat Rev Cancer*, pp. 753-763, vol. 6 (2006).

Rubio et al., "Potent anti-HPV immune responses induced by tandem repeats of the HPV16 L2 (20-38) peptide displayed on bacterial thioredoxin," *Vaccine*, pp. 1949-1956, vol. 27. (2009).

Schmiedeskamp et al., "Human papillomavirus vaccines," *Ann. Pharmacother*, pp. 1344-1352, vol. 40 (2006).

Skerra et al., "Alternative non-antibody scaffolds for molecular recognition," Current Opinion in Biotechnology, London, GB, pp. 295-304, vol. 18, No. 4 (2007).

Woodman et al., "Design and validation of a Neutral Protein scaffold for the Presentation of Peptide Aptamers," *Journal of Molecular Biology*, London, GB, pp. 1118-1133, vol. 352, No. 5 (2005).

Yang et al., "Cell surface-binding motifs of L2 that facilitate papillomavirus infection," *J Virol*, pp. 3531-3541, vol. 77 (2003).

International Preliminary Report on Patentability and Written Opinion cited in related International Patent Application No. PCT/EP2009/067422, dated Jun. 21, 2011.

International Search Report cited in related International Patent Application No. PCT/EP2009/067422, completed Feb. 25, 2010.

\* cited by examiner

| L2(x) | n |
|---|---|
| L2 (1-120) | 1, 2, 3 |
| L2 (20-38) | 1, 3, 9, 15 |
| L2 (28-42) | 1, 4, 8 |
| L2 (56-75) | 1, 4 |
| L2 (64-81) | 1, 4, 8 |
| L2 (96-115) | 1, 4, 8 |
| L2 (108-120) | 1, 4, 7, 9 |

Figure 1A

```
           20         KTCKQAGTCPPDIIPKVEG
                                        38
HPV16
HPV18    .....S........VV...  .
HPV58    Q...AS........V....  .
HPV45    R....S........V.N...
HPV31    Q....A.......S.V...I.H
``` figure 6

| PSV | Disease (relative contribution) | Neutralizing mAbs | | | | | |
|---|---|---|---|---|---|---|---|
| | | (20-38)#4 | (20-38)#18 | (20-38)#15 | (28-42)#8 | (64-81)#1 |
| HPV16 | cervical cancer (53) | 3125 | 625 | <5 | 3125 | 78125 |
| HPV58 | cervical cancer (2,2) | 625 | 3125 | <5 | <5 | <5 |
| HPV31 | cervical cancer (2,9) | <5 | 50 | <5 | <5 | <5 |
| HPV45 | cervical cancer (6,7) | 625 | 625 | <5 | <5 | <5 |
| HPV18 | cervical cancer (17,2) | 625 | 3125 | <5 | <5 | <5 |
| HPV57 | common warts | 625 | 625 | <5 | <5 | <5 |
| HPV27 | common warts | 625 | 625 | <5 | <5 | <5 |
| BPV-1 | Bovine fibropapilloma | 625 | 125 | <5 | <5 | <5 | figure 7

SEQUENCE LISTING

<160> NUMBER OF SEQ ID NOS: 498

<210> SEQ ID NO 1
<211> LENGTH: 120
<212> TYPE: PRT
<213> ORGANISM: Human papillomavirus type 16

<400> SEQUENCE: 1

Met Arg His Lys Arg Ser Ala Lys Arg Thr Lys Arg Ala Ser Ala Thr
1               5                   10                  15

Gln Leu Tyr Lys Thr Cys Lys Gln Ala Gly Thr Cys Pro Pro Asp Ile
            20                  25                  30

Ile Pro Lys Val Glu Gly Lys Thr Ile Ala Glu Gln Ile Leu Gln Tyr
        35                  40                  45

Gly Ser Met Gly Val Phe Phe Gly Gly Leu Gly Ile Gly Thr Gly Ser
    50                  55                  60

Gly Thr Gly Gly Arg Thr Gly Tyr Ile Pro Leu Gly Thr Arg Pro Pro
65                  70                  75                  80

Thr Ala Thr Asp Thr Leu Ala Pro Val Arg Pro Pro Leu Thr Val Asp
                85                  90                  95

Pro Val Gly Pro Ser Asp Pro Ser Ile Val Ser Leu Val Glu Glu Thr
            100                 105                 110

```
Ser Phe Ile Asp Ala Gly Ala Pro
        115                 120

<210> SEQ ID NO 2
<211> LENGTH: 19
<212> TYPE: PRT
<213> ORGANISM: Human papillomavirus type 16

<400> SEQUENCE: 2

Lys Thr Cys Lys Gln Ala Gly Thr Cys Pro Pro Asp Ile Ile Pro Lys
1               5                   10                  15

Val Glu Gly

<210> SEQ ID NO 3
<211> LENGTH: 12
<212> TYPE: PRT
<213> ORGANISM: Human papillomavirus type 16

<400> SEQUENCE: 3

Lys Thr Cys Lys Gln Ala Gly Thr Cys Pro Pro Asp
1               5                   10

<210> SEQ ID NO 4
<211> LENGTH: 11
<212> TYPE: PRT
<213> ORGANISM: Human papillomavirus type 16

<400> SEQUENCE: 4

Thr Cys Lys Gln Ala Gly Thr Cys Pro Pro Asp
1               5                   10

<210> SEQ ID NO 5
<211> LENGTH: 10
<212> TYPE: PRT
<213> ORGANISM: Human papillomavirus type 16

<400> SEQUENCE: 5

Cys Lys Gln Ala Gly Thr Cys Pro Pro Asp
1               5                   10

<210> SEQ ID NO 6
<211> LENGTH: 10
<212> TYPE: PRT
<213> ORGANISM: Human papillomavirus type 16

<400> SEQUENCE: 6

Thr Cys Lys Gln Ala Gly Thr Cys Pro Pro
1               5                   10

<210> SEQ ID NO 7
<211> LENGTH: 9
<212> TYPE: PRT
<213> ORGANISM: Human papillomavirus type 16

<400> SEQUENCE: 7

Cys Lys Gln Ala Gly Thr Cys Pro Pro
1               5

<210> SEQ ID NO 8
<211> LENGTH: 10
<212> TYPE: PRT
<213> ORGANISM: Human papillomavirus type 16

<400> SEQUENCE: 8
```

Asp Ile Ile Pro Lys Val Glu Gly Lys Thr
1               5                   10

<210> SEQ ID NO 9
<211> LENGTH: 9
<212> TYPE: PRT
<213> ORGANISM: Human papillomavirus type 16

<400> SEQUENCE: 9

Thr Gly Tyr Ile Pro Leu Gly Thr Arg
1               5

<210> SEQ ID NO 10
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 10

Lys Thr Cys Lys Gln Xaa Gly Thr Cys Pro Pro Asp Ile Ile Pro Lys
1               5                   10                  15

Val Glu Gly

<210> SEQ ID NO 11
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 11

Lys Thr Cys Lys Gln Xaa Gly Thr Cys Pro Pro Asp
1               5                   10

<210> SEQ ID NO 12
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 12

Thr Cys Lys Gln Xaa Gly Thr Cys Pro Pro Asp
1               5                   10

<210> SEQ ID NO 13
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 13

Cys Lys Gln Xaa Gly Thr Cys Pro Pro Asp
1               5                   10

<210> SEQ ID NO 14
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 14

Thr Cys Lys Gln Xaa Gly Thr Cys Pro Pro
1               5                   10

<210> SEQ ID NO 15
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 15

Cys Lys Gln Xaa Gly Thr Cys Pro Pro
1               5

<210> SEQ ID NO 16
<211> LENGTH: 3
<212> TYPE: PRT
<213> ORGANISM: artificial
<220> FEATURE:
<223> OTHER INFORMATION: linker peptide

<400> SEQUENCE: 16

Gly Gly Pro
1

<210> SEQ ID NO 17
<211> LENGTH: 4
<212> TYPE: PRT
<213> ORGANISM: artificial
<220> FEATURE:
<223> OTHER INFORMATION: linker peptide

<400> SEQUENCE: 17

Gly Pro Gly Pro
1

<210> SEQ ID NO 18
<211> LENGTH: 5
<212> TYPE: PRT
<213> ORGANISM: artificial
<220> FEATURE:
<223> OTHER INFORMATION: linker peptide

<400> SEQUENCE: 18

Gly Pro Gly Pro Gly
1               5

```
<210> SEQ ID NO 19
<211> LENGTH: 4
<212> TYPE: PRT
<213> ORGANISM: artificial
<220> FEATURE:
<223> OTHER INFORMATION: linker peptide

<400> SEQUENCE: 19

Ser Gly Ser Gly
1

<210> SEQ ID NO 20
<211> LENGTH: 63
<212> TYPE: PRT
<213> ORGANISM: artificial
<220> FEATURE:
<223> OTHER INFORMATION: Multimers with (GGP) linker

<400> SEQUENCE: 20

Lys Thr Cys Lys Gln Ala Gly Thr Cys Pro Pro Asp Ile Ile Pro Lys
1               5                  10                  15

Val Glu Gly Gly Gly Pro Lys Thr Cys Lys Gln Ala Gly Thr Cys Pro
            20                  25                  30

Pro Asp Ile Ile Pro Lys Val Glu Gly Gly Gly Pro Lys Thr Cys Lys
        35                  40                  45

Gln Ala Gly Thr Cys Pro Pro Asp Ile Ile Pro Lys Val Glu Gly
    50                  55                  60

<210> SEQ ID NO 21
<211> LENGTH: 195
<212> TYPE: PRT
<213> ORGANISM: artificial
<220> FEATURE:
<223> OTHER INFORMATION: Multimers with (GGP) linker

<400> SEQUENCE: 21

Lys Thr Cys Lys Gln Ala Gly Thr Cys Pro Pro Asp Ile Ile Pro Lys
1               5                  10                  15

Val Glu Gly Gly Gly Pro Lys Thr Cys Lys Gln Ala Gly Thr Cys Pro
            20                  25                  30

Pro Asp Ile Ile Pro Lys Val Glu Gly Gly Gly Pro Lys Thr Cys Lys
        35                  40                  45

Gln Ala Gly Thr Cys Pro Pro Asp Ile Ile Pro Lys Val Glu Gly Gly
    50                  55                  60

Gly Pro Lys Thr Cys Lys Gln Ala Gly Thr Cys Pro Pro Asp Ile Ile
65                  70                  75                  80

Pro Lys Val Glu Gly Gly Gly Pro Lys Thr Cys Lys Gln Ala Gly Thr
                85                  90                  95

Cys Pro Pro Asp Ile Ile Pro Lys Val Glu Gly Gly Gly Pro Lys Thr
            100                 105                 110

Cys Lys Gln Ala Gly Thr Cys Pro Pro Asp Ile Ile Pro Lys Val Glu
        115                 120                 125

Gly Gly Gly Pro Lys Thr Cys Lys Gln Ala Gly Thr Cys Pro Pro Asp
    130                 135                 140

Ile Ile Pro Lys Val Glu Gly Gly Gly Pro Lys Thr Cys Lys Gln Ala
145                 150                 155                 160

Gly Thr Cys Pro Pro Asp Ile Ile Pro Lys Val Glu Gly Gly Gly Pro
                165                 170                 175

Lys Thr Cys Lys Gln Ala Gly Thr Cys Pro Pro Asp Ile Ile Pro Lys
```

```
                    180                 185                 190

Val Glu Gly
        195

<210> SEQ ID NO 22
<211> LENGTH: 72
<212> TYPE: PRT
<213> ORGANISM: artificial
<220> FEATURE:
<223> OTHER INFORMATION: Multimers with (GGP) linker

<400> SEQUENCE: 22

Lys Thr Cys Lys Gln Ala Gly Thr Cys Pro Pro Asp Gly Gly Pro Lys
1               5                   10                  15

Thr Cys Lys Gln Ala Gly Thr Cys Pro Pro Asp Gly Gly Pro Lys Thr
            20                  25                  30

Cys Lys Gln Ala Gly Thr Cys Pro Pro Asp Gly Gly Pro Lys Thr Cys
        35                  40                  45

Lys Gln Ala Gly Thr Cys Pro Pro Asp Gly Gly Pro Lys Thr Cys Lys
    50                  55                  60

Gln Ala Gly Thr Cys Pro Pro Asp
65                  70

<210> SEQ ID NO 23
<211> LENGTH: 4
<212> TYPE: PRT
<213> ORGANISM: artificial
<220> FEATURE:
<223> OTHER INFORMATION: Thioredoxin display site

<400> SEQUENCE: 23

Cys Gly Pro Cys
1

<210> SEQ ID NO 24
<211> LENGTH: 109
<212> TYPE: PRT
<213> ORGANISM: Escherichia coli

<400> SEQUENCE: 24

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105

<210> SEQ ID NO 25
<211> LENGTH: 109
<212> TYPE: PRT
<213> ORGANISM: Salmonella enterica

<400> SEQUENCE: 25
```

```
Met Ser Asp Lys Ile Ile His Leu Thr Asp Asp Ser Phe Gly Thr Asp
1               5                   10                  15

Val Leu Lys Ala Asp Gly Ala Ile Leu Val Asp Phe Trp Ala Glu Trp
                20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala
            100                 105
```

<210> SEQ ID NO 26
<211> LENGTH: 105
<212> TYPE: PRT
<213> ORGANISM: Mus musculus

<400> SEQUENCE: 26

```
Met Val Lys Leu Ile Glu Ser Lys Glu Ala Phe Gln Glu Ala Leu Ala
1               5                   10                  15

Ala Ala Gly Asp Lys Leu Val Val Asp Phe Ser Ala Thr Trp Cys
                20                  25                  30

Gly Pro Cys Lys Met Ile Lys Pro Phe Phe His Ser Leu Cys Asp Lys
            35                  40                  45

Tyr Ser Asn Val Val Phe Leu Glu Val Asp Val Asp Asp Cys Gln Asp
    50                  55                  60

Val Ala Ala Asp Cys Glu Val Lys Cys Met Pro Thr Phe Gln Phe Tyr
65                  70                  75                  80

Lys Lys Gly Gln Lys Val Gly Glu Phe Ser Gly Ala Asn Lys Glu Lys
                85                  90                  95

Leu Glu Ala Ser Ile Thr Glu Tyr Ala
            100                 105
```

<210> SEQ ID NO 27
<211> LENGTH: 105
<212> TYPE: PRT
<213> ORGANISM: Rattus norvegicus

<400> SEQUENCE: 27

```
Met Val Lys Gln Ile Glu Ser Lys Ser Ala Phe Gln Glu Val Leu Asp
1               5                   10                  15

Ser Ala Gly Asp Lys Leu Val Val Asp Phe Ser Ala Thr Trp Cys
                20                  25                  30

Gly Pro Cys Lys Met Ile Lys Pro Phe Phe His Ala Leu Ser Glu Lys
            35                  40                  45

Phe Asn Asn Val Val Phe Ile Glu Val Asp Val Asp Asp Cys Lys Asp
    50                  55                  60

Ile Ala Ala Glu Cys Glu Val Lys Cys Met Pro Thr Phe Gln Phe Phe
65                  70                  75                  80

Lys Lys Gly Gln Lys Val Gly Glu Phe Ser Gly Ala Asn Lys Glu Lys
                85                  90                  95

Leu Glu Ala Thr Ile Asn Glu Leu Leu
            100                 105
```

<210> SEQ ID NO 28
<211> LENGTH: 105
<212> TYPE: PRT
<213> ORGANISM: Homo sapiens

<400> SEQUENCE: 28

```
Met Val Lys Gln Ile Glu Ser Lys Thr Ala Phe Gln Glu Ala Leu Asp
1               5                   10                  15

Ala Ala Gly Asp Lys Leu Val Val Asp Phe Ser Ala Thr Trp Cys
                20                  25                  30

Gly Pro Cys Lys Met Ile Lys Pro Phe Phe His Ser Leu Ser Glu Lys
                35                  40                  45

Tyr Ser Asn Val Ile Phe Leu Glu Val Asp Val Asp Cys Gln Asp
            50                  55                  60

Val Ala Ser Glu Cys Glu Val Lys Cys Met Pro Thr Phe Gln Phe Phe
65                  70                  75                  80

Lys Lys Gly Gln Lys Val Gly Phe Ser Gly Ala Asn Lys Glu Lys
                85                  90                  95

Leu Glu Ala Thr Ile Asn Glu Leu Val
                100                 105
```

<210> SEQ ID NO 29
<211> LENGTH: 216
<212> TYPE: PRT
<213> ORGANISM: artificial
<220> FEATURE:
<223> OTHER INFORMATION: immunogenic polypeptide

<400> SEQUENCE: 29

```
Met Gly Ser Ser His His His His His His Ser Ser Gly Leu Val Pro
1               5                   10                  15

Arg Gly Ser His Met Gly Asp Lys Ile Ile His Leu Thr Asp Asp Ser
                20                  25                  30

Phe Asp Thr Asp Val Leu Lys Ala Asp Gly Ala Ile Leu Val Asp Phe
                35                  40                  45

Trp Ala Glu Trp Cys Gly Pro Lys Thr Cys Lys Gln Ala Gly Thr Cys
            50                  55                  60

Pro Pro Asp Ile Ile Pro Lys Val Glu Gly Gly Pro Lys Thr Cys
65                  70                  75                  80

Lys Gln Ala Gly Thr Cys Pro Pro Asp Ile Ile Pro Lys Val Glu Gly
                85                  90                  95

Gly Gly Pro Lys Thr Cys Lys Gln Ala Gly Thr Cys Pro Pro Asp Ile
                100                 105                 110

Ile Pro Lys Val Glu Gly Gly Pro Cys Lys Met Ile Ala Pro Ile
                115                 120                 125

Leu Asp Glu Ile Ala Asp Glu Tyr Gln Gly Lys Leu Thr Val Ala Lys
    130                 135                 140

Leu Asn Ile Asp Gln Asn Pro Gly Thr Ala Pro Lys Tyr Gly Ile Arg
145                 150                 155                 160

Gly Ile Pro Thr Leu Leu Leu Phe Lys Asn Gly Glu Val Ala Ala Thr
                165                 170                 175

Lys Val Gly Ala Leu Ser Lys Gly Gln Leu Lys Glu Phe Leu Asp Ala
                180                 185                 190

Asn Leu Arg Asp Pro Asn Ser Ser Ser Val Asp Lys Leu Ala Ala Ala
                195                 200                 205
```

Leu Glu His His His His His His
    210                 215

<210> SEQ ID NO 30
<211> LENGTH: 348
<212> TYPE: PRT
<213> ORGANISM: artificial
<220> FEATURE:
<223> OTHER INFORMATION: immunogenic polypeptide

<400> SEQUENCE: 30

Met Gly Ser Ser His His His His Ser Ser Gly Leu Val Pro
1               5                   10                  15

Arg Gly Ser His Met Gly Asp Lys Ile Ile His Leu Thr Asp Asp Ser
            20                  25                  30

Phe Asp Thr Asp Val Leu Lys Ala Asp Gly Ala Ile Leu Val Asp Phe
        35                  40                  45

Trp Ala Glu Trp Cys Gly Pro Lys Thr Cys Lys Gln Ala Gly Thr Cys
    50                  55                  60

Pro Pro Asp Ile Ile Pro Lys Val Glu Gly Gly Pro Lys Thr Cys
65                  70                  75                  80

Lys Gln Ala Gly Thr Cys Pro Pro Asp Ile Ile Pro Lys Val Glu Gly
                85                  90                  95

Gly Gly Pro Lys Thr Cys Lys Gln Ala Gly Thr Cys Pro Pro Asp Ile
            100                 105                 110

Ile Pro Lys Val Glu Gly Gly Pro Lys Thr Cys Lys Gln Ala Gly
        115                 120                 125

Thr Cys Pro Pro Asp Ile Ile Pro Lys Val Glu Gly Gly Pro Lys
130                 135                 140

Thr Cys Lys Gln Ala Gly Thr Cys Pro Pro Asp Ile Ile Pro Lys Val
145                 150                 155                 160

Glu Gly Gly Gly Pro Lys Thr Cys Lys Gln Ala Gly Thr Cys Pro Pro
                165                 170                 175

Asp Ile Ile Pro Lys Val Glu Gly Gly Pro Lys Thr Cys Lys Gln
            180                 185                 190

Ala Gly Thr Cys Pro Pro Asp Ile Ile Pro Lys Val Glu Gly Gly Gly
        195                 200                 205

Pro Lys Thr Cys Lys Gln Ala Gly Thr Cys Pro Pro Asp Ile Ile Pro
    210                 215                 220

Lys Val Glu Gly Gly Gly Pro Lys Thr Cys Lys Gln Ala Gly Thr Cys
225                 230                 235                 240

Pro Pro Asp Ile Ile Pro Lys Val Glu Gly Gly Pro Cys Lys Met
                245                 250                 255

Ile Ala Pro Ile Leu Asp Glu Ile Ala Asp Glu Tyr Gln Gly Lys Leu
            260                 265                 270

Thr Val Ala Lys Leu Asn Ile Asp Gln Asn Pro Gly Thr Ala Pro Lys
        275                 280                 285

Tyr Gly Ile Arg Gly Ile Pro Thr Leu Leu Leu Phe Lys Asn Gly Glu
    290                 295                 300

Val Ala Ala Thr Lys Val Gly Ala Leu Ser Lys Gly Gln Leu Lys Glu
305                 310                 315                 320

Phe Leu Asp Ala Asn Leu Arg Asp Pro Asn Ser Ser Val Asp Lys
                325                 330                 335

Leu Ala Ala Ala Leu Glu His His His His His His
            340                 345

<210> SEQ ID NO 31
<211> LENGTH: 9
<212> TYPE: PRT
<213> ORGANISM: Human papillomavirus type 16

<400> SEQUENCE: 31

Ile Ile Pro Lys Val Glu Gly Lys Thr
1               5

<210> SEQ ID NO 32
<211> LENGTH: 8
<212> TYPE: PRT
<213> ORGANISM: Human papillomavirus type 16

<400> SEQUENCE: 32

Ile Pro Lys Val Glu Gly Lys Thr
1               5

<210> SEQ ID NO 33
<211> LENGTH: 19
<212> TYPE: PRT
<213> ORGANISM: artificial
<220> FEATURE:
<223> OTHER INFORMATION: L2 fragment

<400> SEQUENCE: 33

Arg Gly Cys Lys Gln Ala Gly Thr Cys Pro Pro Asp Val Ile Asn Lys
1               5                   10                  15

Val Glu Gln

<210> SEQ ID NO 34
<211> LENGTH: 19
<212> TYPE: PRT
<213> ORGANISM: artificial
<220> FEATURE:
<223> OTHER INFORMATION: L2 fragment

<400> SEQUENCE: 34

Arg Gly Cys Lys Ala Ser Asn Thr Cys Pro Pro Asp Val Ile Asn Lys
1               5                   10                  15

Val Glu Gln

<210> SEQ ID NO 35
<211> LENGTH: 19
<212> TYPE: PRT
<213> ORGANISM: artificial
<220> FEATURE:
<223> OTHER INFORMATION: L2 fragment

<400> SEQUENCE: 35

Arg Gly Cys Lys Ala Ala Gly Thr Cys Pro Pro Asp Val Ile Asn Lys
1               5                   10                  15

Val Glu Gln

<210> SEQ ID NO 36
<211> LENGTH: 19
<212> TYPE: PRT
<213> ORGANISM: artificial
<220> FEATURE:
<223> OTHER INFORMATION: L2 fragment

<400> SEQUENCE: 36

Gln Ser Cys Lys Ala Ala Gly Thr Cys Pro Pro Asp Val Leu Asn Lys
1               5                   10                  15

Val Glu Gln

```
<210> SEQ ID NO 37
<211> LENGTH: 19
<212> TYPE: PRT
<213> ORGANISM: artificial
<220> FEATURE:
<223> OTHER INFORMATION: L2 fragment

<400> SEQUENCE: 37
```

Gln Ser Cys Lys Ala Ala Gly Thr Cys Pro Pro Asp Val Val Asn Lys
1               5                   10                  15

Val Glu Gln

```
<210> SEQ ID NO 38
<211> LENGTH: 19
<212> TYPE: PRT
<213> ORGANISM: artificial
<220> FEATURE:
<223> OTHER INFORMATION: L2 fragment

<400> SEQUENCE: 38
```

Gln Thr Cys Lys Gln Ala Gly Thr Cys Pro Pro Asp Val Ile Asn Lys
1               5                   10                  15

Val Glu Gln

```
<210> SEQ ID NO 39
<211> LENGTH: 19
<212> TYPE: PRT
<213> ORGANISM: artificial
<220> FEATURE:
<223> OTHER INFORMATION: L2 fragment

<400> SEQUENCE: 39
```

Gln Thr Cys Lys Gln Ala Gly Thr Cys Pro Pro Asp Val Ile Asn Lys
1               5                   10                  15

Val Glu Gln

```
<210> SEQ ID NO 40
<211> LENGTH: 19
<212> TYPE: PRT
<213> ORGANISM: artificial
<220> FEATURE:
<223> OTHER INFORMATION: L2 fragment

<400> SEQUENCE: 40
```

Arg Thr Cys Lys Gln Ala Gly Thr Cys Pro Pro Asp Val Ile Asn Lys
1               5                   10                  15

Val Glu Ser

```
<210> SEQ ID NO 41
<211> LENGTH: 19
<212> TYPE: PRT
<213> ORGANISM: artificial
<220> FEATURE:
<223> OTHER INFORMATION: L2 fragment

<400> SEQUENCE: 41
```

Arg Thr Cys Lys Gln Ala Gly Thr Cys Pro Pro Asp Val Ile Asn Lys
1               5                   10                  15

Val Glu Gln

```
<210> SEQ ID NO 42
<211> LENGTH: 19
<212> TYPE: PRT
<213> ORGANISM: artificial
<220> FEATURE:
<223> OTHER INFORMATION: L2 fragment

<400> SEQUENCE: 42

Lys Gly Cys Lys Ala Ser Gly Thr Cys Pro Pro Asp Val Ile Asn Lys
1               5                   10                  15
Val Glu Gln

<210> SEQ ID NO 43
<211> LENGTH: 19
<212> TYPE: PRT
<213> ORGANISM: artificial
<220> FEATURE:
<223> OTHER INFORMATION: L2 fragment

<400> SEQUENCE: 43

Arg Thr Cys Lys Gln Ser Gly Thr Cys Pro Pro Asp Val Val Pro Lys
1               5                   10                  15
Val Glu Gly

<210> SEQ ID NO 44
<211> LENGTH: 19
<212> TYPE: PRT
<213> ORGANISM: artificial
<220> FEATURE:
<223> OTHER INFORMATION: L2 fragment

<400> SEQUENCE: 44

Arg Thr Cys Lys Gln Ala Gly Thr Cys Pro Pro Asp Val Ile Pro Lys
1               5                   10                  15
Val Glu Gly

<210> SEQ ID NO 45
<211> LENGTH: 19
<212> TYPE: PRT
<213> ORGANISM: artificial
<220> FEATURE:
<223> OTHER INFORMATION: L2 fragment

<400> SEQUENCE: 45

Arg Thr Cys Lys Val Thr Gly Thr Cys Pro Ala Asp Val Val Pro Lys
1               5                   10                  15
Val Glu Gly

<210> SEQ ID NO 46
<211> LENGTH: 19
<212> TYPE: PRT
<213> ORGANISM: artificial
<220> FEATURE:
<223> OTHER INFORMATION: L2 fragment

<400> SEQUENCE: 46

Arg Thr Cys Lys Ala Thr Gly Thr Arg Pro Ala Asp Val Ile Pro Lys
1               5                   10                  15
Val Glu Gly

<210> SEQ ID NO 47
<211> LENGTH: 19
<212> TYPE: PRT
<213> ORGANISM: artificial
```

<220> FEATURE:
<223> OTHER INFORMATION: L2 fragment

<400> SEQUENCE: 47

Arg Thr Cys Lys Gln Ser Gly Thr Cys Pro Pro Asp Ile Ile Pro Arg
1               5                   10                  15

Val Glu Gln

<210> SEQ ID NO 48
<211> LENGTH: 19
<212> TYPE: PRT
<213> ORGANISM: artificial
<220> FEATURE:
<223> OTHER INFORMATION: L2 fragment

<400> SEQUENCE: 48

Arg Thr Cys Lys Gln Ala Gly Thr Cys Pro Pro Asp Ile Ile Pro Arg
1               5                   10                  15

Leu Glu Gln

<210> SEQ ID NO 49
<211> LENGTH: 19
<212> TYPE: PRT
<213> ORGANISM: artificial
<220> FEATURE:
<223> OTHER INFORMATION: L2 fragment

<400> SEQUENCE: 49

Arg Thr Cys Lys Gln Ala Gly Thr Cys Pro Pro Asp Ile Ile Pro Arg
1               5                   10                  15

Val Glu Gln

<210> SEQ ID NO 50
<211> LENGTH: 19
<212> TYPE: PRT
<213> ORGANISM: artificial
<220> FEATURE:
<223> OTHER INFORMATION: L2 fragment

<400> SEQUENCE: 50

Lys Thr Cys Lys Val Ala Gly Thr Cys Pro Pro Asp Val Ile Pro Lys
1               5                   10                  15

Val Glu Gly

<210> SEQ ID NO 51
<211> LENGTH: 19
<212> TYPE: PRT
<213> ORGANISM: artificial
<220> FEATURE:
<223> OTHER INFORMATION: L2 fragment

<400> SEQUENCE: 51

Lys Thr Cys Lys Ala Ala Gly Thr Cys Pro Pro Asp Val Ile Pro Lys
1               5                   10                  15

Val Glu Gly

<210> SEQ ID NO 52
<211> LENGTH: 19
<212> TYPE: PRT
<213> ORGANISM: artificial
<220> FEATURE:
<223> OTHER INFORMATION: L2 fragment

<400> SEQUENCE: 52

```
Arg Thr Cys Lys Ala Ala Gly Thr Cys Pro Pro Asp Val Ile Pro Lys
1               5                   10                  15

Val Glu Gly
```

<210> SEQ ID NO 53
<211> LENGTH: 19
<212> TYPE: PRT
<213> ORGANISM: artificial
<220> FEATURE:
<223> OTHER INFORMATION: L2 fragment

<400> SEQUENCE: 53

```
Arg Thr Cys Lys Ala Ser Gly Thr Cys Pro Pro Asp Val Ile Pro Lys
1               5                   10                  15

Val Glu Gly
```

<210> SEQ ID NO 54
<211> LENGTH: 19
<212> TYPE: PRT
<213> ORGANISM: artificial
<220> FEATURE:
<223> OTHER INFORMATION: L2 fragment

<400> SEQUENCE: 54

```
Ser Thr Cys Lys Ala Ala Gly Thr Cys Pro Ala Asp Val Ile Pro Lys
1               5                   10                  15

Val Glu Gly
```

<210> SEQ ID NO 55
<211> LENGTH: 19
<212> TYPE: PRT
<213> ORGANISM: artificial
<220> FEATURE:
<223> OTHER INFORMATION: L2 fragment

<400> SEQUENCE: 55

```
Lys Thr Cys Lys Leu Ser Gly Thr Cys Pro Glu Asp Val Ile Asn Lys
1               5                   10                  15

Val Glu Gln
```

<210> SEQ ID NO 56
<211> LENGTH: 19
<212> TYPE: PRT
<213> ORGANISM: artificial
<220> FEATURE:
<223> OTHER INFORMATION: L2 fragment

<400> SEQUENCE: 56

```
Lys Thr Cys Lys Gln Ser Gly Thr Cys Pro Pro Asp Ile Ile Pro Lys
1               5                   10                  15

Val Glu Gly
```

<210> SEQ ID NO 57
<211> LENGTH: 19
<212> TYPE: PRT
<213> ORGANISM: artificial
<220> FEATURE:
<223> OTHER INFORMATION: L2 fragment

<400> SEQUENCE: 57

```
Lys Thr Cys Lys Gln Ala Gly Thr Cys Pro Pro Asp Ile Val Pro Lys
1               5                   10                  15
```

Val Glu Gly

<210> SEQ ID NO 58
<211> LENGTH: 19
<212> TYPE: PRT
<213> ORGANISM: artificial
<220> FEATURE:
<223> OTHER INFORMATION: L2 fragment

<400> SEQUENCE: 58

Gln Thr Cys Lys Ala Ser Gly Thr Cys Pro Pro Asp Val Ile Pro Lys
1               5                   10                  15

Val Glu Gly

<210> SEQ ID NO 59
<211> LENGTH: 19
<212> TYPE: PRT
<213> ORGANISM: artificial
<220> FEATURE:
<223> OTHER INFORMATION: L2 fragment

<400> SEQUENCE: 59

Lys Thr Cys Lys Gln Ala Gly Thr Cys Pro Pro Asp Val Ile Pro Lys
1               5                   10                  15

Val Glu Gly

<210> SEQ ID NO 60
<211> LENGTH: 19
<212> TYPE: PRT
<213> ORGANISM: artificial
<220> FEATURE:
<223> OTHER INFORMATION: L2 fragment

<400> SEQUENCE: 60

Gln Thr Cys Lys Ala Ala Gly Thr Cys Pro Ser Asp Ile Ile Pro Lys
1               5                   10                  15

Val Glu His

<210> SEQ ID NO 61
<211> LENGTH: 19
<212> TYPE: PRT
<213> ORGANISM: artificial
<220> FEATURE:
<223> OTHER INFORMATION: L2 fragment

<400> SEQUENCE: 61

Gln Thr Cys Lys Ala Ser Gly Thr Cys Pro Pro Asp Val Ile Pro Lys
1               5                   10                  15

Val Glu Gln

<210> SEQ ID NO 62
<211> LENGTH: 19
<212> TYPE: PRT
<213> ORGANISM: artificial
<220> FEATURE:
<223> OTHER INFORMATION: L2 fragment

<400> SEQUENCE: 62

Gln Thr Cys Lys Leu Thr Gly Thr Cys Pro Pro Asp Val Ile Pro Lys
1               5                   10                  15

Val Glu His

<210> SEQ ID NO 63

```
<211> LENGTH: 19
<212> TYPE: PRT
<213> ORGANISM: artificial
<220> FEATURE:
<223> OTHER INFORMATION: L2 fragment

<400> SEQUENCE: 63

Gln Thr Cys Lys Ala Ala Gly Thr Cys Pro Ser Asp Val Ile Asn Lys
1               5                   10                  15

Val Glu His

<210> SEQ ID NO 64
<211> LENGTH: 19
<212> TYPE: PRT
<213> ORGANISM: artificial
<220> FEATURE:
<223> OTHER INFORMATION: L2 fragment

<400> SEQUENCE: 64

Lys Gln Cys Gln Leu Gly Ala Asp Cys Pro Pro Asp Val Arg Asn Lys
1               5                   10                  15

Val Glu Gly

<210> SEQ ID NO 65
<211> LENGTH: 19
<212> TYPE: PRT
<213> ORGANISM: artificial
<220> FEATURE:
<223> OTHER INFORMATION: L2 fragment

<400> SEQUENCE: 65

Ala Lys Cys Gln Leu Ser Gly Asn Cys Leu Pro Asp Val Lys Asn Lys
1               5                   10                  15

Val Glu Ala

<210> SEQ ID NO 66
<211> LENGTH: 19
<212> TYPE: PRT
<213> ORGANISM: artificial
<220> FEATURE:
<223> OTHER INFORMATION: L2 fragment

<400> SEQUENCE: 66

Ala Lys Cys Gln Leu Ser Gly Asp Cys Leu Pro Asp Val Lys Asn Lys
1               5                   10                  15

Val Glu Ala

<210> SEQ ID NO 67
<211> LENGTH: 19
<212> TYPE: PRT
<213> ORGANISM: artificial
<220> FEATURE:
<223> OTHER INFORMATION: L2 fragment

<400> SEQUENCE: 67

Arg His Cys Ala Leu Ser Gly Thr Cys Pro Asp Asp Val Lys Asn Lys
1               5                   10                  15

Val Glu Asn

<210> SEQ ID NO 68
<211> LENGTH: 19
<212> TYPE: PRT
<213> ORGANISM: artificial
<220> FEATURE:
```

<223> OTHER INFORMATION: L2 fragment

<400> SEQUENCE: 68

Lys His Cys Ala Gly Ser Gly Thr Cys Pro Glu Asp Val Lys Asn Lys
1               5                   10                  15

Val Glu Gln

<210> SEQ ID NO 69
<211> LENGTH: 19
<212> TYPE: PRT
<213> ORGANISM: artificial
<220> FEATURE:
<223> OTHER INFORMATION: L2 fragment

<400> SEQUENCE: 69

Lys Thr Cys Leu Gln Gly Gly Asp Cys Ile Pro Asp Val Lys Asn Lys
1               5                   10                  15

Phe Glu Asn

<210> SEQ ID NO 70
<211> LENGTH: 19
<212> TYPE: PRT
<213> ORGANISM: artificial
<220> FEATURE:
<223> OTHER INFORMATION: L2 fragment

<400> SEQUENCE: 70

Arg Ser Cys Leu Gln Gly Gly Asp Cys Ile Pro Asp Val Gln Asn Lys
1               5                   10                  15

Phe Glu Gly

<210> SEQ ID NO 71
<211> LENGTH: 19
<212> TYPE: PRT
<213> ORGANISM: artificial
<220> FEATURE:
<223> OTHER INFORMATION: L2 fragment

<400> SEQUENCE: 71

Gln Thr Cys Lys Ala Thr Gly Thr Cys Pro Pro Asp Val Ile Pro Lys
1               5                   10                  15

Val Glu Gly

<210> SEQ ID NO 72
<211> LENGTH: 19
<212> TYPE: PRT
<213> ORGANISM: artificial
<220> FEATURE:
<223> OTHER INFORMATION: L2 fragment

<400> SEQUENCE: 72

Lys Thr Cys Lys Gln Ser Gly Thr Cys Pro Pro Asp Val Val Pro Lys
1               5                   10                  15

Val Glu Gly

<210> SEQ ID NO 73
<211> LENGTH: 19
<212> TYPE: PRT
<213> ORGANISM: artificial
<220> FEATURE:
<223> OTHER INFORMATION: L2 fragment

<400> SEQUENCE: 73

```
Arg Thr Cys Lys Gln Ser Gly Thr Cys Pro Pro Asp Val Ile Asn Lys
1               5                   10                  15

Val Glu Gly
```

<210> SEQ ID NO 74
<211> LENGTH: 19
<212> TYPE: PRT
<213> ORGANISM: artificial
<220> FEATURE:
<223> OTHER INFORMATION: L2 fragment

<400> SEQUENCE: 74

```
Lys Thr Cys Lys Gln Ala Gly Thr Cys Pro Ser Asp Val Ile Asn Lys
1               5                   10                  15

Val Glu Gly
```

<210> SEQ ID NO 75
<211> LENGTH: 19
<212> TYPE: PRT
<213> ORGANISM: artificial
<220> FEATURE:
<223> OTHER INFORMATION: L2 fragment

<400> SEQUENCE: 75

```
Lys Thr Cys Lys Leu Ser Gly Thr Cys Pro Glu Asp Val Val Asn Lys
1               5                   10                  15

Ile Glu Gln
```

<210> SEQ ID NO 76
<211> LENGTH: 19
<212> TYPE: PRT
<213> ORGANISM: artificial
<220> FEATURE:
<223> OTHER INFORMATION: L2 fragment

<400> SEQUENCE: 76

```
Arg Thr Cys Lys Gln Ser Gly Thr Cys Pro Pro Asp Val Val Asp Lys
1               5                   10                  15

Val Glu Gly
```

<210> SEQ ID NO 77
<211> LENGTH: 19
<212> TYPE: PRT
<213> ORGANISM: artificial
<220> FEATURE:
<223> OTHER INFORMATION: L2 fragment

<400> SEQUENCE: 77

```
Ser Thr Cys Lys Ala Ala Gly Thr Cys Pro Pro Asp Val Val Asn Lys
1               5                   10                  15

Val Glu Gly
```

<210> SEQ ID NO 78
<211> LENGTH: 19
<212> TYPE: PRT
<213> ORGANISM: artificial
<220> FEATURE:
<223> OTHER INFORMATION: L2 fragment

<400> SEQUENCE: 78

```
Pro Thr Cys Lys Ile Ala Gly Asn Cys Pro Ala Asp Ile Gln Asn Lys
1               5                   10                  15

Phe Glu Asn
```

```
<210> SEQ ID NO 79
<211> LENGTH: 19
<212> TYPE: PRT
<213> ORGANISM: artificial
<220> FEATURE:
<223> OTHER INFORMATION: L2 fragment

<400> SEQUENCE: 79

Pro Ala Cys Lys Ile Ser Asn Thr Cys Pro Pro Asp Ile Ile Asn Lys
1               5                   10                  15

Tyr Glu Asn

<210> SEQ ID NO 80
<211> LENGTH: 12
<212> TYPE: PRT
<213> ORGANISM: artificial
<220> FEATURE:
<223> OTHER INFORMATION: L2 fragment

<400> SEQUENCE: 80

Arg Gly Cys Lys Gln Ala Gly Thr Cys Pro Pro Asp
1               5                   10

<210> SEQ ID NO 81
<211> LENGTH: 12
<212> TYPE: PRT
<213> ORGANISM: artificial
<220> FEATURE:
<223> OTHER INFORMATION: L2 fragment

<400> SEQUENCE: 81

Arg Gly Cys Lys Ala Ser Asn Thr Cys Pro Pro Asp
1               5                   10

<210> SEQ ID NO 82
<211> LENGTH: 12
<212> TYPE: PRT
<213> ORGANISM: artificial
<220> FEATURE:
<223> OTHER INFORMATION: L2 fragment

<400> SEQUENCE: 82

Arg Gly Cys Lys Ala Ala Gly Thr Cys Pro Pro Asp
1               5                   10

<210> SEQ ID NO 83
<211> LENGTH: 12
<212> TYPE: PRT
<213> ORGANISM: artificial
<220> FEATURE:
<223> OTHER INFORMATION: L2 fragment

<400> SEQUENCE: 83

Gln Ser Cys Lys Ala Ala Gly Thr Cys Pro Pro Asp
1               5                   10

<210> SEQ ID NO 84
<211> LENGTH: 12
<212> TYPE: PRT
<213> ORGANISM: artificial
<220> FEATURE:
<223> OTHER INFORMATION: L2 fragment

<400> SEQUENCE: 84

Gln Thr Cys Lys Gln Ala Gly Thr Cys Pro Pro Asp
```

```
<210> SEQ ID NO 85
<211> LENGTH: 12
<212> TYPE: PRT
<213> ORGANISM: artificial
<220> FEATURE:
<223> OTHER INFORMATION: L2 fragment

<400> SEQUENCE: 85

Arg Thr Cys Lys Gln Ala Gly Thr Cys Pro Pro Asp
1               5                   10

<210> SEQ ID NO 86
<211> LENGTH: 12
<212> TYPE: PRT
<213> ORGANISM: artificial
<220> FEATURE:
<223> OTHER INFORMATION: L2 fragment

<400> SEQUENCE: 86

Lys Gly Cys Lys Ala Ser Gly Thr Cys Pro Pro Asp
1               5                   10

<210> SEQ ID NO 87
<211> LENGTH: 12
<212> TYPE: PRT
<213> ORGANISM: artificial
<220> FEATURE:
<223> OTHER INFORMATION: L2 fragment

<400> SEQUENCE: 87

Arg Thr Cys Lys Gln Ser Gly Thr Cys Pro Pro Asp
1               5                   10

<210> SEQ ID NO 88
<211> LENGTH: 12
<212> TYPE: PRT
<213> ORGANISM: artificial
<220> FEATURE:
<223> OTHER INFORMATION: L2 fragment

<400> SEQUENCE: 88

Arg Thr Cys Lys Val Thr Gly Thr Cys Pro Ala Asp
1               5                   10

<210> SEQ ID NO 89
<211> LENGTH: 12
<212> TYPE: PRT
<213> ORGANISM: artificial
<220> FEATURE:
<223> OTHER INFORMATION: L2 fragment

<400> SEQUENCE: 89

Arg Thr Cys Lys Ala Thr Gly Thr Arg Pro Ala Asp
1               5                   10

<210> SEQ ID NO 90
<211> LENGTH: 12
<212> TYPE: PRT
<213> ORGANISM: artificial
<220> FEATURE:
<223> OTHER INFORMATION: L2 fragment

<400> SEQUENCE: 90

Lys Thr Cys Lys Val Ala Gly Thr Cys Pro Pro Asp
1               5                   10
```

```
<210> SEQ ID NO 91
<211> LENGTH: 12
<212> TYPE: PRT
<213> ORGANISM: artificial
<220> FEATURE:
<223> OTHER INFORMATION: L2 fragment

<400> SEQUENCE: 91

Lys Thr Cys Lys Ala Ala Gly Thr Cys Pro Pro Asp
1               5                   10

<210> SEQ ID NO 92
<211> LENGTH: 12
<212> TYPE: PRT
<213> ORGANISM: artificial
<220> FEATURE:
<223> OTHER INFORMATION: L2 fragment

<400> SEQUENCE: 92

Arg Thr Cys Lys Ala Ala Gly Thr Cys Pro Pro Asp
1               5                   10

<210> SEQ ID NO 93
<211> LENGTH: 12
<212> TYPE: PRT
<213> ORGANISM: artificial
<220> FEATURE:
<223> OTHER INFORMATION: L2 fragment

<400> SEQUENCE: 93

Arg Thr Cys Lys Ala Ser Gly Thr Cys Pro Pro Asp
1               5                   10

<210> SEQ ID NO 94
<211> LENGTH: 12
<212> TYPE: PRT
<213> ORGANISM: artificial
<220> FEATURE:
<223> OTHER INFORMATION: L2 fragment

<400> SEQUENCE: 94

Ser Thr Cys Lys Ala Ala Gly Thr Cys Pro Ala Asp
1               5                   10

<210> SEQ ID NO 95
<211> LENGTH: 12
<212> TYPE: PRT
<213> ORGANISM: artificial
<220> FEATURE:
<223> OTHER INFORMATION: L2 fragment

<400> SEQUENCE: 95

Lys Thr Cys Lys Leu Ser Gly Thr Cys Pro Glu Asp
1               5                   10

<210> SEQ ID NO 96
<211> LENGTH: 12
<212> TYPE: PRT
<213> ORGANISM: artificial
<220> FEATURE:
<223> OTHER INFORMATION: L2 fragment

<400> SEQUENCE: 96

Lys Thr Cys Lys Gln Ala Gly Thr Cys Pro Glu Asp
1               5                   10
```

```
<210> SEQ ID NO 97
<211> LENGTH: 12
<212> TYPE: PRT
<213> ORGANISM: artificial
<220> FEATURE:
<223> OTHER INFORMATION: L2 fragment

<400> SEQUENCE: 97

Gln Thr Cys Lys Ala Ser Gly Thr Cys Pro Pro Asp
1               5                   10

<210> SEQ ID NO 98
<211> LENGTH: 12
<212> TYPE: PRT
<213> ORGANISM: artificial
<220> FEATURE:
<223> OTHER INFORMATION: L2 fragment

<400> SEQUENCE: 98

Gln Thr Cys Lys Ala Ala Gly Thr Cys Pro Ser Asp
1               5                   10

<210> SEQ ID NO 99
<211> LENGTH: 12
<212> TYPE: PRT
<213> ORGANISM: artificial
<220> FEATURE:
<223> OTHER INFORMATION: L2 fragment

<400> SEQUENCE: 99

Gln Thr Cys Lys Leu Thr Gly Thr Cys Pro Pro Asp
1               5                   10

<210> SEQ ID NO 100
<211> LENGTH: 12
<212> TYPE: PRT
<213> ORGANISM: artificial
<220> FEATURE:
<223> OTHER INFORMATION: L2 fragment

<400> SEQUENCE: 100

Lys Gln Cys Gln Leu Gly Ala Asp Cys Pro Pro Asp
1               5                   10

<210> SEQ ID NO 101
<211> LENGTH: 12
<212> TYPE: PRT
<213> ORGANISM: artificial
<220> FEATURE:
<223> OTHER INFORMATION: L2 fragment

<400> SEQUENCE: 101

Ala Lys Cys Gln Leu Ser Gly Asn Cys Leu Pro Asp
1               5                   10

<210> SEQ ID NO 102
<211> LENGTH: 12
<212> TYPE: PRT
<213> ORGANISM: artificial
<220> FEATURE:
<223> OTHER INFORMATION: L2 fragment

<400> SEQUENCE: 102

Ala Lys Cys Gln Leu Ser Gly Asp Cys Leu Pro Asp
1               5                   10
```

```
<210> SEQ ID NO 103
<211> LENGTH: 12
<212> TYPE: PRT
<213> ORGANISM: artificial
<220> FEATURE:
<223> OTHER INFORMATION: L2 fragment

<400> SEQUENCE: 103

Arg His Cys Ala Leu Ser Gly Thr Cys Pro Asp Asp
1               5                   10

<210> SEQ ID NO 104
<211> LENGTH: 12
<212> TYPE: PRT
<213> ORGANISM: artificial
<220> FEATURE:
<223> OTHER INFORMATION: L2 fragment

<400> SEQUENCE: 104

Lys His Cys Ala Gly Ser Gly Thr Cys Pro Glu Asp
1               5                   10

<210> SEQ ID NO 105
<211> LENGTH: 12
<212> TYPE: PRT
<213> ORGANISM: artificial
<220> FEATURE:
<223> OTHER INFORMATION: L2 fragment

<400> SEQUENCE: 105

Lys Thr Cys Leu Gln Gly Gly Asp Cys Ile Pro Asp
1               5                   10

<210> SEQ ID NO 106
<211> LENGTH: 12
<212> TYPE: PRT
<213> ORGANISM: artificial
<220> FEATURE:
<223> OTHER INFORMATION: L2 fragment

<400> SEQUENCE: 106

Arg Ser Cys Leu Gln Gly Gly Asp Cys Ile Pro Asp
1               5                   10

<210> SEQ ID NO 107
<211> LENGTH: 12
<212> TYPE: PRT
<213> ORGANISM: artificial
<220> FEATURE:
<223> OTHER INFORMATION: L2 fragment

<400> SEQUENCE: 107

Gln Thr Cys Lys Ala Thr Gly Thr Cys Pro Pro Asp
1               5                   10

<210> SEQ ID NO 108
<211> LENGTH: 12
<212> TYPE: PRT
<213> ORGANISM: artificial
<220> FEATURE:
<223> OTHER INFORMATION: L2 fragment

<400> SEQUENCE: 108

Lys Thr Cys Lys Gln Ser Gly Thr Cys Pro Pro Asp
1               5                   10

<210> SEQ ID NO 109
```

```
<211> LENGTH: 12
<212> TYPE: PRT
<213> ORGANISM: artificial
<220> FEATURE:
<223> OTHER INFORMATION: L2 fragment

<400> SEQUENCE: 109

Lys Thr Cys Lys Gln Ala Gly Thr Cys Pro Ser Asp
1               5                   10

<210> SEQ ID NO 110
<211> LENGTH: 12
<212> TYPE: PRT
<213> ORGANISM: artificial
<220> FEATURE:
<223> OTHER INFORMATION: L2 fragment

<400> SEQUENCE: 110

Ser Thr Cys Lys Ala Ala Gly Thr Cys Pro Pro Asp
1               5                   10

<210> SEQ ID NO 111
<211> LENGTH: 12
<212> TYPE: PRT
<213> ORGANISM: artificial
<220> FEATURE:
<223> OTHER INFORMATION: L2 fragment

<400> SEQUENCE: 111

Pro Thr Cys Lys Ile Ala Gly Asn Cys Pro Ala Asp
1               5                   10

<210> SEQ ID NO 112
<211> LENGTH: 12
<212> TYPE: PRT
<213> ORGANISM: artificial
<220> FEATURE:
<223> OTHER INFORMATION: L2 fragment

<400> SEQUENCE: 112

Pro Ala Cys Lys Ile Ser Asn Thr Cys Pro Pro Asp
1               5                   10

<210> SEQ ID NO 113
<211> LENGTH: 11
<212> TYPE: PRT
<213> ORGANISM: artificial
<220> FEATURE:
<223> OTHER INFORMATION: L2 fragment

<400> SEQUENCE: 113

Gly Cys Lys Gln Ala Gly Thr Cys Pro Pro Asp
1               5                   10

<210> SEQ ID NO 114
<211> LENGTH: 11
<212> TYPE: PRT
<213> ORGANISM: artificial
<220> FEATURE:
<223> OTHER INFORMATION: L2 fragment

<400> SEQUENCE: 114

Gly Cys Lys Ala Ser Asn Thr Cys Pro Pro Asp
1               5                   10

<210> SEQ ID NO 115
<211> LENGTH: 11
```

<212> TYPE: PRT
<213> ORGANISM: artificial
<220> FEATURE:
<223> OTHER INFORMATION: L2 fragment

<400> SEQUENCE: 115

Gly Cys Lys Ala Ala Gly Thr Cys Pro Pro Asp
1               5                   10

<210> SEQ ID NO 116
<211> LENGTH: 11
<212> TYPE: PRT
<213> ORGANISM: artificial
<220> FEATURE:
<223> OTHER INFORMATION: L2 fragment

<400> SEQUENCE: 116

Ser Cys Lys Ala Ala Gly Thr Cys Pro Pro Asp
1               5                   10

<210> SEQ ID NO 117
<211> LENGTH: 11
<212> TYPE: PRT
<213> ORGANISM: artificial
<220> FEATURE:
<223> OTHER INFORMATION: L2 fragment

<400> SEQUENCE: 117

Thr Cys Lys Gln Ser Gly Thr Cys Pro Ser Asp
1               5                   10

<210> SEQ ID NO 118
<211> LENGTH: 11
<212> TYPE: PRT
<213> ORGANISM: artificial
<220> FEATURE:
<223> OTHER INFORMATION: L2 fragment

<400> SEQUENCE: 118

Gly Cys Lys Ala Ser Gly Thr Cys Pro Pro Asp
1               5                   10

<210> SEQ ID NO 119
<211> LENGTH: 11
<212> TYPE: PRT
<213> ORGANISM: artificial
<220> FEATURE:
<223> OTHER INFORMATION: L2 fragment

<400> SEQUENCE: 119

Thr Cys Lys Gln Ser Gly Thr Cys Pro Pro Asp
1               5                   10

<210> SEQ ID NO 120
<211> LENGTH: 11
<212> TYPE: PRT
<213> ORGANISM: artificial
<220> FEATURE:
<223> OTHER INFORMATION: L2 fragment

<400> SEQUENCE: 120

Thr Cys Lys Val Thr Gly Thr Cys Pro Ala Asp
1               5                   10

<210> SEQ ID NO 121
<211> LENGTH: 11
<212> TYPE: PRT

<213> ORGANISM: artificial
<220> FEATURE:
<223> OTHER INFORMATION: L2 fragment

<400> SEQUENCE: 121

Thr Cys Lys Ala Thr Gly Thr Arg Pro Ala Asp
1               5                   10

<210> SEQ ID NO 122
<211> LENGTH: 11
<212> TYPE: PRT
<213> ORGANISM: artificial
<220> FEATURE
<220> FEATURE:
<223> OTHER INFORMATION: L2 fragment

<400> SEQUENCE: 127

Thr Cys Lys Ala Ala Gly Thr Cys Pro Ser Asp
1               5                   10

<210> SEQ ID NO 128
<211> LENGTH: 11
<212> TYPE: PRT
<213> ORGANISM: artificial
<220> FEATURE:
<223> OTHER INFORMATION: L2 fragment

<400> SEQUENCE: 128

Thr Cys Lys Leu Thr Gly Thr Cys Pro Pro Asp
1               5                   10

<210> SEQ ID NO 129
<211> LENGTH: 11
<212> TYPE: PRT
<213> ORGANISM: artificial
<220> FEATURE:
<223> OTHER INFORMATION: L2 fragment

<400> SEQUENCE: 129

Gln Cys Gln Leu Gly Ala Asp Cys Pro Pro Asp
1               5                   10

<210> SEQ ID NO 130
<211> LENGTH: 11
<212> TYPE: PRT
<213> ORGANISM: artificial
<220> FEATURE:
<223> OTHER INFORMATION: L2 fragment

<400> SEQUENCE: 130

Lys Cys Gln Leu Ser Gly Asn Cys Leu Pro Asp
1               5                   10

<210> SEQ ID NO 131
<211> LENGTH: 11
<212> TYPE: PRT
<213> ORGANISM: artificial
<220> FEATURE:
<223> OTHER INFORMATION: L2 fragment

<400> SEQUENCE: 131

Lys Cys Gln Leu Ser Gly Asp Cys Leu Pro Asp
1               5                   10

<210> SEQ ID NO 132
<211> LENGTH: 11
<212> TYPE: PRT
<213> ORGANISM: artificial
<220> FEATURE:
<223> OTHER INFORMATION: L2 fragment

<400> SEQUENCE: 132

His Cys Ala Leu Ser Gly Thr Cys Pro Asp Asp
1               5                   10

<210> SEQ ID NO 133
<211> LENGTH: 11
<212> TYPE: PRT
<213> ORGANISM: artificial
<220> FEATURE:

<223> OTHER INFORMATION: L2 fragment

<400> SEQUENCE: 133

His Cys Ala Gly Ser Gly Thr Cys Pro Glu Asp
1               5                   10

<210> SEQ ID NO 134
<211> LENGTH: 11
<212> TYPE: PRT
<213> ORGANISM: artificial
<220> FEATURE:
<223> OTHER INFORMATION: L2 fragment

<400> SEQUENCE: 134

Thr Cys Leu Gln Gly Gly Asp Cys Ile Pro Asp
1               5                   10

<210> SEQ ID NO 135
<211> LENGTH: 11
<212> TYPE: PRT
<213> ORGANISM: artificial
<220> FEATURE:
<223> OTHER INFORMATION: L2 fragment

<400> SEQUENCE: 135

Ser Cys Leu Gln Gly Gly Asp Cys Ile Pro Asp
1               5                   10

<210> SEQ ID NO 136
<211> LENGTH: 11
<212> TYPE: PRT
<213> ORGANISM: artificial
<220> FEATURE:
<223> OTHER INFORMATION: L2 fragment

<400> SEQUENCE: 136

Thr Cys Lys Ala Thr Gly Thr Cys Pro Pro Asp
1               5                   10

<210> SEQ ID NO 137
<211> LENGTH: 11
<212> TYPE: PRT
<213> ORGANISM: artificial
<220> FEATURE:
<223> OTHER INFORMATION: L2 fragment

<400> SEQUENCE: 137

Thr Cys Lys Gln Ala Gly Thr Cys Pro Ser Asp
1               5                   10

<210> SEQ ID NO 138
<211> LENGTH: 11
<212> TYPE: PRT
<213> ORGANISM: artificial
<220> FEATURE:
<223> OTHER INFORMATION: L2 fragment

<400> SEQUENCE: 138

Thr Cys Lys Ile Ala Gly Asn Cys Pro Ala Asp
1               5                   10

<210> SEQ ID NO 139
<211> LENGTH: 11
<212> TYPE: PRT
<213> ORGANISM: artificial
<220> FEATURE:
<223> OTHER INFORMATION: L2 fragment

<400> SEQUENCE: 139

Ala Cys Lys Ile Ser Asn Thr Cys Pro Pro Asp
1               5                   10

<210> SEQ ID NO 140
<211> LENGTH: 11
<212> TYPE: PRT
<213> ORGANISM: artificial
<220> FEATURE:
<223> OTHER INFORMATION: L2 fragment

<400> SEQUENCE: 140

Thr Cys Lys Gln Ser Gly Thr Cys Pro Ser Asp
1               5                   10

<210> SEQ ID NO 141
<211> LENGTH: 10
<212> TYPE: PRT
<213> ORGANISM: artificial
<220> FEATURE:
<223> OTHER INFORMATION: L2 fragment

<400> SEQUENCE: 141

Cys Lys Ala Ser Asn Thr Cys Pro Pro Asp
1               5                   10

<210> SEQ ID NO 142
<211> LENGTH: 10
<212> TYPE: PRT
<213> ORGANISM: artificial
<220> FEATURE:
<223> OTHER INFORMATION: L2 fragment

<400> SEQUENCE: 142

Cys Lys Ala Ser Asn Thr Cys Pro Pro Asp
1               5                   10

<210> SEQ ID NO 143
<211> LENGTH: 10
<212> TYPE: PRT
<213> ORGANISM: artificial
<220> FEATURE:
<223> OTHER INFORMATION: L2 fragment

<400> SEQUENCE: 143

Cys Lys Ala Ser Gly Thr Cys Pro Pro Asp
1               5                   10

<210> SEQ ID NO 144
<211> LENGTH: 10
<212> TYPE: PRT
<213> ORGANISM: artificial
<220> FEATURE:
<223> OTHER INFORMATION: L2 fragment

<400> SEQUENCE: 144

Cys Lys Gln Ser Gly Thr Cys Pro Pro Asp
1               5                   10

<210> SEQ ID NO 145
<211> LENGTH: 10
<212> TYPE: PRT
<213> ORGANISM: artificial
<220> FEATURE:
<223> OTHER INFORMATION: L2 fragment

<400> SEQUENCE: 145

Cys Lys Val Thr Gly Thr Cys Pro Ala Asp
1               5                   10

<210> SEQ ID NO 146
<211> LENGTH: 10
<212> TYPE: PRT
<213> ORGANISM: artificial
<220> FEATURE:
<223> OTHER INFORMATION: L2 fragment

<400> SEQUENCE: 146

Cys Lys Ala Thr Gly Thr Arg Pro Ala Asp
1               5                   10

<210> SEQ ID NO 147
<211> LENGTH: 10
<212> TYPE: PRT
<213> ORGANISM: artificial
<220> FEATURE:
<223> OTHER INFORMATION: L2 fragment

<400> SEQUENCE: 147

Cys Lys Val Ala Gly Thr Cys Pro Pro Asp
1               5                   10

<210> SEQ ID NO 148
<211> LENGTH: 10
<212> TYPE: PRT
<213> ORGANISM: artificial
<220> FEATURE:
<223> OTHER INFORMATION: L2 fragment

<400> SEQUENCE: 148

Cys Lys Val Ala Gly Thr Cys Pro Pro Asp
1               5                   10

<210> SEQ ID NO 149
<211> LENGTH: 10
<212> TYPE: PRT
<213> ORGANISM: artificial
<220> FEATURE:
<223> OTHER INFORMATION: L2 fragment

<400> SEQUENCE: 149

Cys Lys Leu Ser Gly Thr Cys Pro Glu Asp
1               5                   10

<210> SEQ ID NO 150
<211> LENGTH: 10
<212> TYPE: PRT
<213> ORGANISM: artificial
<220> FEATURE:
<223> OTHER INFORMATION: L2 fragment

<400> SEQUENCE: 150

Cys Lys Ala Ala Gly Thr Cys Pro Ser Asp
1               5                   10

<210> SEQ ID NO 151
<211> LENGTH: 10
<212> TYPE: PRT
<213> ORGANISM: artificial
<220> FEATURE:
<223> OTHER INFORMATION: L2 fragment

<400> SEQUENCE: 151

Cys Lys Leu Thr Gly Thr Cys Pro Pro Asp
1               5                   10

<210> SEQ ID NO 152
<211> LENGTH: 10
<212> TYPE: PRT
<213> ORGANISM: artificial
<220> FEATURE:
<223> OTHER INFORMATION: L2 fragment

<400> SEQUENCE: 152

Cys Gln Leu Gly Ala Asp Cys Pro Pro Asp
1               5                   10

<210> SEQ ID NO 153
<211> LENGTH: 10
<212> TYPE: PRT
<213> ORGANISM: artificial
<220> FEATURE:
<223> OTHER INFORMATION: L2 fragment

<400> SEQUENCE: 153

Cys Gln Leu Ser Gly Asn Cys Leu Pro Asp
1               5                   10

<210> SEQ ID NO 154
<211> LENGTH: 10
<212> TYPE: PRT
<213> ORGANISM: artificial
<220> FEATURE:
<223> OTHER INFORMATION: L2 fragment

<400> SEQUENCE: 154

Cys Gln Leu Ser Gly Asn Cys Leu Pro Asp
1               5                   10

<210> SEQ ID NO 155
<211> LENGTH: 10
<212> TYPE: PRT
<213> ORGANISM: artificial
<220> FEATURE:
<223> OTHER INFORMATION: L2 fragment

<400> SEQUENCE: 155

Cys Ala Leu Ser Gly Thr Cys Pro Asp Asp
1               5                   10

<210> SEQ ID NO 156
<211> LENGTH: 10
<212> TYPE: PRT
<213> ORGANISM: artificial
<220> FEATURE:
<223> OTHER INFORMATION: L2 fragment

<400> SEQUENCE: 156

Cys Ala Gly Ser Gly Thr Cys Pro Glu Asp
1               5                   10

<210> SEQ ID NO 157
<211> LENGTH: 10
<212> TYPE: PRT
<213> ORGANISM: artificial
<220> FEATURE:
<223> OTHER INFORMATION: L2 fragment

<400> SEQUENCE: 157

Cys Leu Gln Gly Gly Asp Cys Ile Pro Asp
1               5                   10

<210> SEQ ID NO 158
<211> LENGTH: 10
<212> TYPE: PRT
<213> ORGANISM: artificial
<220> FEATURE:
<223> OTHER INFORMATION: L2 fragment

<400> SEQUENCE: 158

Cys Lys Ala Thr Gly Thr Cys Pro Pro Asp
1               5                   10

<210> SEQ ID NO 159
<211> LENGTH: 10
<212> TYPE: PRT
<213> ORGANISM: artificial
<220> FEATURE:
<223> OTHER INFORMATION: L2 fragment

<400> SEQUENCE: 159

Cys Lys Gln Ala Gly Thr Cys Pro Ser Asp
1               5                   10

<210> SEQ ID NO 160
<211> LENGTH: 10
<212> TYPE: PRT
<213> ORGANISM: artificial
<220> FEATURE:
<223> OTHER INFORMATION: L2 fragment

<400> SEQUENCE: 160

Cys Lys Ile Ala Gly Asn Cys Pro Ala Asp
1               5                   10

<210> SEQ ID NO 161
<211> LENGTH: 10
<212> TYPE: PRT
<213> ORGANISM: artificial
<220> FEATURE:
<223> OTHER INFORMATION: L2 fragment

<400> SEQUENCE: 161

Cys Lys Ile Ser Asn Thr Cys Pro Pro Asp
1               5                   10

<210> SEQ ID NO 162
<211> LENGTH: 10
<212> TYPE: PRT
<213> ORGANISM: artificial
<220> FEATURE:
<223> OTHER INFORMATION: L2 fragment

<400> SEQUENCE: 162

Gly Cys Lys Gln Ala Gly Thr Cys Pro Pro
1               5                   10

<210> SEQ ID NO 163
<211> LENGTH: 10
<212> TYPE: PRT
<213> ORGANISM: artificial
<220> FEATURE:
<223> OTHER INFORMATION: L2 fragment

<400> SEQUENCE: 163

Gly Cys Lys Ala Ser Asn Thr Cys Pro Pro

```
1               5                   10
```

<210> SEQ ID NO 164
<211> LENGTH: 10
<212> TYPE: PRT
<213> ORGANISM: artificial
<220> FEATURE:
<223> OTHER INFORMATION: L2 fragment

<400> SEQUENCE: 164

```
Gly Cys Lys Ala Ala Gly Thr Cys Pro Pro
1               5                   10
```

<210> SEQ ID NO 165
<211> LENGTH: 10
<212> TYPE: PRT
<213> ORGANISM: artificial
<220> FEATURE:
<223> OTHER INFORMATION: L2 fragment

<400> SEQUENCE: 165

```
Ser Cys Lys Ala Ala Gly Thr Cys Pro Pro
1               5                   10
```

<210> SEQ ID NO 166
<211> LENGTH: 10
<212> TYPE: PRT
<213> ORGANISM: artificial
<220> FEATURE:
<223> OTHER INFORMATION: L2 fragment

<400> SEQUENCE: 166

```
Thr Cys Lys Leu Ala Gly Thr Cys Pro Pro
1               5                   10
```

<210> SEQ ID NO 167
<211> LENGTH: 10
<212> TYPE: PRT
<213> ORGANISM: artificial
<220> FEATURE:
<223> OTHER INFORMATION: L2 fragment

<400> SEQUENCE: 167

```
Gly Cys Lys Ala Ser Gly Thr Cys Pro Pro
1               5                   10
```

<210> SEQ ID NO 168
<211> LENGTH: 10
<212> TYPE: PRT
<213> ORGANISM: artificial
<220> FEATURE:
<223> OTHER INFORMATION: L2 fragment

<400> SEQUENCE: 168

```
Thr Cys Lys Gln Ser Gly Thr Cys Pro Pro
1               5                   10
```

<210> SEQ ID NO 169
<211> LENGTH: 10
<212> TYPE: PRT
<213> ORGANISM: artificial
<220> FEATURE:
<223> OTHER INFORMATION: L2 fragment

<400> SEQUENCE: 169

```
Thr Cys Lys Val Thr Gly Thr Cys Pro Ala
1               5                   10
```

<210> SEQ ID NO 170
<211> LENGTH: 10
<212> TYPE: PRT
<213> ORGANISM: artificial
<220> FEATURE:
<223> OTHER INFORMATION: L2 fragment

<400> SEQUENCE: 170

Thr Cys Lys Ala Thr Gly Thr Arg Pro Ala
1               5                   10

<210> SEQ ID NO 171
<211> LENGTH: 10
<212> TYPE: PRT
<213> ORGANISM: artificial
<220> FEATURE:
<223> OTHER INFORMATION: L2 fragment

<400> SEQUENCE: 171

Thr Cys Lys Val Ala Gly Thr Cys Pro Pro
1               5                   10

<210> SEQ ID NO 172
<211> LENGTH: 10
<212> TYPE: PRT
<213> ORGANISM: artifiicial

<400> SEQUENCE: 172

Thr Cys Lys Ala Ala Gly Thr Cys Pro Pro
1               5                   10

<210> SEQ ID NO 173
<211> LENGTH: 10
<212> TYPE: PRT
<213> ORGANISM: artificial
<220> FEATURE:
<223> OTHER INFORMATION: L2 fragment

<400> SEQUENCE: 173

Thr Cys Lys Ala Ser Gly Thr Cys Pro Pro
1               5                   10

<210> SEQ ID NO 174
<211> LENGTH: 10
<212> TYPE: PRT
<213> ORGANISM: artificial
<220> FEATURE:
<223> OTHER INFORMATION: L2 fragment

<400> SEQUENCE: 174

Thr Cys Lys Ala Ala Gly Thr Cys Pro Ala
1               5                   10

<210> SEQ ID NO 175
<211> LENGTH: 10
<212> TYPE: PRT
<213> ORGANISM: artificial
<220> FEATURE:
<223> OTHER INFORMATION: L2 fragment

<400> SEQUENCE: 175

Thr Cys Lys Leu Ser Gly Thr Cys Pro Glu
1               5                   10

<210> SEQ ID NO 176

```
<211> LENGTH: 10
<212> TYPE: PRT
<213> ORGANISM: artificial
<220> FEATURE:
<223> OTHER INFORMATION: L2 fragment

<400> SEQUENCE: 176

Thr Cys Lys Ala Ala Gly Thr Cys Pro Ser
1               5                   10

<210> SEQ ID NO 177
<211> LENGTH: 10
<212> TYPE: PRT
<213> ORGANISM: artificial
<220> FEATURE:
<223> OTHER INFORMATION: L2 fragment

<400> SEQUENCE: 177

Thr Cys Lys Leu Thr Gly Thr Cys Pro Pro
1               5                   10

<210> SEQ ID NO 178
<211> LENGTH: 10
<212> TYPE: PRT
<213> ORGANISM: artificial
<220> FEATURE:
<223> OTHER INFORMATION: L2 fragment

<400> SEQUENCE: 178

Gln Cys Gln Leu Gly Ala Asp Cys Pro Pro
1               5                   10

<210> SEQ ID NO 179
<211> LENGTH: 10
<212> TYPE: PRT
<213> ORGANISM: artificial
<220> FEATURE:
<223> OTHER INFORMATION: L2 fragment

<400> SEQUENCE: 179

Lys Cys Gln Leu Ser Gly Asn Cys Leu Pro
1               5                   10

<210> SEQ ID NO 180
<211> LENGTH: 10
<212> TYPE: PRT
<213> ORGANISM: artificial
<220> FEATURE:
<223> OTHER INFORMATION: L2 fragment

<400> SEQUENCE: 180

Lys Cys Gln Leu Ser Gly Asp Cys Leu Pro
1               5                   10

<210> SEQ ID NO 181
<211> LENGTH: 10
<212> TYPE: PRT
<213> ORGANISM: artificial
<220> FEATURE:
<223> OTHER INFORMATION: L2 fragment

<400> SEQUENCE: 181

His Cys Ala Leu Ser Gly Thr Cys Pro Asp
1               5                   10

<210> SEQ ID NO 182
<211> LENGTH: 10
```

<212> TYPE: PRT
<213> ORGANISM: artificial
<220> FEATURE:
<223> OTHER INFORMATION: L2 fragment

<400> SEQUENCE: 182

His Cys Ala Gly Ser Gly Thr Cys Pro Glu
1               5                   10

<210> SEQ ID NO 183
<211> LENGTH: 10
<212> TYPE: PRT
<213> ORGANISM: artificial
<220> FEATURE:
<223> OTHER INFORMATION: L2 fragment

<400> SEQUENCE: 183

Thr Cys Leu Gln Gly Gly Asp Cys Ile Pro
1               5                   10

<210> SEQ ID NO 184
<211> LENGTH: 10
<212> TYPE: PRT
<213> ORGANISM: artificial
<220> FEATURE:
<223> OTHER INFORMATION: L2 fragment

<400> SEQUENCE: 184

Ser Cys Leu Gln Gly Gly Asp Cys Ile Pro
1               5                   10

<210> SEQ ID NO 185
<211> LENGTH: 10
<212> TYPE: PRT
<213> ORGANISM: artificial
<220> FEATURE:
<223> OTHER INFORMATION: L2 fragment

<400> SEQUENCE: 185

Thr Cys Lys Ala Thr Gly Thr Cys Pro Pro
1               5                   10

<210> SEQ ID NO 186
<211> LENGTH: 10
<212> TYPE: PRT
<213> ORGANISM: artificial
<220> FEATURE:
<223> OTHER INFORMATION: L2 fragment

<400> SEQUENCE: 186

Thr Cys Lys Gln Ala Gly Thr Cys Pro Ser
1               5                   10

<210> SEQ ID NO 187
<211> LENGTH: 10
<212> TYPE: PRT
<213> ORGANISM: artificial
<220> FEATURE:
<223> OTHER INFORMATION: L2 fragment

<400> SEQUENCE: 187

Thr Cys Lys Ile Ala Gly Asn Cys Pro Ala
1               5                   10

<210> SEQ ID NO 188
<211> LENGTH: 10
<212> TYPE: PRT

```
<213> ORGANISM: artificial
<220> FEATURE:
<223> OTHER INFORMATION: L2 fragment

<400> SEQUENCE: 188

Ala Cys Lys Ile Ser Asn Thr Cys Pro Pro
1 5 10

<210> SEQ ID NO 189
<211> LENGTH: 9
<212> TYPE: PRT
<213> ORGANISM: artificial
<220> FEATURE:
<223> OTHER INFORMATION: L2 fragment

<400> SEQUENCE: 189

Cys Lys Leu Ala Gly Thr Cys Pro Pro
1 5

<210> SEQ ID NO 190
<211> LENGTH: 9
<212> TYPE: PRT
<213> ORGANISM: artificial
<220> FEATURE:
<223> OTHER INFORMATION: L2 fragment

<400> SEQUENCE: 190

Cys Lys Ala Ser Asn Thr Cys Pro Pro
1 5

<210> SEQ ID NO 191
<211> LENGTH: 9
<212> TYPE: PRT
<213> ORGANISM: artificial
<220> FEATURE:
<223> OTHER INFORMATION: L2 fragment

<400> SEQUENCE: 191

Cys Lys Ala Ala Gly Thr Cys Pro Pro
1 5

<210> SEQ ID NO 192
<211> LENGTH: 9
<212> TYPE: PRT
<213> ORGANISM: artificial
<220> FEATURE:
<223> OTHER INFORMATION: L2 fragment

<400> SEQUENCE: 192

Cys Lys Ala Ser Gly Thr Cys Pro Pro
1 5

<210> SEQ ID NO 193
<211> LENGTH: 9
<212> TYPE: PRT
<213> ORGANISM: artificial
<220> FEATURE:
<223> OTHER INFORMATION: L2 fragment

<400> SEQUENCE: 193

Cys Lys Gln Ser Gly Thr Cys Pro Pro
1 5

<210> SEQ ID NO 194
<211> LENGTH: 9
<212> TYPE: PRT
<213> ORGANISM: artificial

```
<220> FEATURE:
<223> OTHER INFORMATION: L2 fragment

<400> SEQUENCE: 194

Cys Lys Val Thr Gly Thr Cys Pro Ala
1               5

<210> SEQ ID NO 195
<211> LENGTH: 9
<212> TYPE: PRT
<213> ORGANISM: artificial
<220> FEATURE:
<223> OTHER INFORMATION: L2 fragment

<400> SEQUENCE: 195

Cys Lys Ala Thr Gly Thr Arg Pro Ala
1               5

<210> SEQ ID NO 196
<211> LENGTH: 9
<212> TYPE: PRT
<213> ORGANISM: artificial
<220> FEATURE:
<223> OTHER INFORMATION: L2 fragment

<400> SEQUENCE: 196

Cys Lys Val Ala Gly Thr Cys Pro Pro
1               5

<210> SEQ ID NO 197
<211> LENGTH: 9
<212> TYPE: PRT
<213> ORGANISM: artificial
<220> FEATURE:
<223> OTHER INFORMATION: L2 fragment

<400> SEQUENCE: 197

Cys Lys Val Ala Gly Thr Cys Pro Pro
1               5

<210> SEQ ID NO 198
<211> LENGTH: 9
<212> TYPE: PRT
<213> ORGANISM: artificial
<220> FEATURE:
<223> OTHER INFORMATION: L2 fragment

<400> SEQUENCE: 198

Cys Lys Leu Ser Gly Thr Cys Pro Glu
1               5

<210> SEQ ID NO 199
<211> LENGTH: 9
<212> TYPE: PRT
<213> ORGANISM: artificial
<220> FEATURE:
<223> OTHER INFORMATION: L2 fragment

<400> SEQUENCE: 199

Cys Lys Ala Ala Gly Thr Cys Pro Ser
1               5

<210> SEQ ID NO 200
<211> LENGTH: 9
<212> TYPE: PRT
<213> ORGANISM: artificial
<220> FEATURE:
```

<223> OTHER INFORMATION: L2 fragment

<400> SEQUENCE: 200

Cys Lys Leu Thr Gly Thr Cys Pro Pro
1               5

<210> SEQ ID NO 201
<211> LENGTH: 9
<212> TYPE: PRT
<213> ORGANISM: artificial
<220> FEATURE:
<223> OTHER INFORMATION: L2 fragment

<400> SEQUENCE: 201

Cys Gln Leu Gly Ala Asp Cys Pro Pro
1               5

<210> SEQ ID NO 202
<211> LENGTH: 9
<212> TYPE: PRT
<213> ORGANISM: artificial
<220> FEATURE:
<223> OTHER INFORMATION: L2 fragment

<400> SEQUENCE: 202

Cys Gln Leu Ser Gly Asn Cys Leu Pro
1               5

<210> SEQ ID NO 203
<211> LENGTH: 9
<212> TYPE: PRT
<213> ORGANISM: artifical

<400> SEQUENCE: 203

Cys Gln Leu Ser Gly Asp Cys Leu Pro
1               5

<210> SEQ ID NO 204
<211> LENGTH: 9
<212> TYPE: PRT
<213> ORGANISM: artificial
<220> FEATURE:
<223> OTHER INFORMATION: L2 fragment

<400> SEQUENCE: 204

Cys Ala Leu Ser Gly Thr Cys Pro Asp
1               5

<210> SEQ ID NO 205
<211> LENGTH: 9
<212> TYPE: PRT
<213> ORGANISM: artificial
<220> FEATURE:
<223> OTHER INFORMATION: L2 fragment

<400> SEQUENCE: 205

Cys Ala Gly Ser Gly Thr Cys Pro Glu
1               5

<210> SEQ ID NO 206
<211> LENGTH: 9
<212> TYPE: PRT
<213> ORGANISM: artificial
<220> FEATURE:
<223> OTHER INFORMATION: L2 fragment

<400> SEQUENCE: 206

Cys Leu Gln Gly Gly Asp Cys Ile Pro
1               5

<210> SEQ ID NO 207
<211> LENGTH: 9
<212> TYPE: PRT
<213> ORGANISM: artificial
<220> FEATURE:
<223> OTHER INFORMATION: L2 fragment

<400> SEQUENCE: 207

Cys Lys Ala Thr Gly Thr Cys Pro Pro
1               5

<210> SEQ ID NO 208
<211> LENGTH: 9
<212> TYPE: PRT
<213> ORGANISM: artificial
<220> FEATURE:
<223> OTHER INFORMATION: L2 fragment

<400> SEQUENCE: 208

Cys Lys Gln Ala Gly Thr Cys Pro Ser
1               5

<210> SEQ ID NO 209
<211> LENGTH: 9
<212> TYPE: PRT
<213> ORGANISM: artificial
<220> FEATURE:
<223> OTHER INFORMATION: L2 fragment

<400> SEQUENCE: 209

Cys Lys Gln Ala Gly Thr Cys Pro Ser
1               5

<210> SEQ ID NO 210
<211> LENGTH: 9
<212> TYPE: PRT
<213> ORGANISM: artificial
<220> FEATURE:
<223> OTHER INFORMATION: L2 fragment

<400> SEQUENCE: 210

Cys Lys Ile Ser Asn Thr Cys Pro Pro
1               5

<210> SEQ ID NO 211
<211> LENGTH: 10
<212> TYPE: PRT
<213> ORGANISM: artificial
<220> FEATURE:
<223> OTHER INFORMATION: L2 fragment

<400> SEQUENCE: 211

Asp Val Ile Asn Lys Val Glu Gln Thr Thr
1               5                   10

<210> SEQ ID NO 212
<211> LENGTH: 10
<212> TYPE: PRT
<213> ORGANISM: artificial
<220> FEATURE:
<223> OTHER INFORMATION: L2 fragment

<400> SEQUENCE: 212

Asp Val Ile Asn Lys Val Glu Gln Ser Thr
1               5                   10

<210> SEQ ID NO 213
<211> LENGTH: 10
<212> TYPE: PRT
<213> ORGANISM: artificial
<220> FEATURE:
<223> OTHER INFORMATION: L2 fragment

<400> SEQUENCE: 213

Asp Val Ile Asn Lys Val Glu Gln Lys Thr
1               5                   10

<210> SEQ ID NO 214
<211> LENGTH: 10
<212> TYPE: PRT
<213> ORGANISM: artificial
<220> FEATURE:
<223> OTHER INFORMATION: L2 fragment

<400> SEQUENCE: 214

Asp Val Leu Asn Lys Val Glu Gln Thr Thr
1               5                   10

<210> SEQ ID NO 215
<211> LENGTH: 10
<212> TYPE: PRT
<213> ORGANISM: artificial
<220> FEATURE:
<223> OTHER INFORMATION: L2 fragment

<400> SEQUENCE: 215

Asp Val Val Asn Lys Val Glu Gln Thr Thr
1               5                   10

<210> SEQ ID NO 216
<211> LENGTH: 10
<212> TYPE: PRT
<213> ORGANISM: artificial
<220> FEATURE:
<223> OTHER INFORMATION: L2 fragment

<400> SEQUENCE: 216

Asp Val Ile Asn Lys Val Glu Ser Thr Thr
1               5                   10

<210> SEQ ID NO 217
<211> LENGTH: 10
<212> TYPE: PRT
<213> ORGANISM: artificial
<220> FEATURE:
<223> OTHER INFORMATION: L2 fragment

<400> SEQUENCE: 217

Asp Val Ile Asn Lys Val Glu Gln Asn Thr
1               5                   10

<210> SEQ ID NO 218
<211> LENGTH: 10
<212> TYPE: PRT
<213> ORGANISM: artificial
<220> FEATURE:
<223> OTHER INFORMATION: L2 fragment

<400> SEQUENCE: 218

Asp Val Val Pro Lys Val Glu Gly Asp Thr

```
<210> SEQ ID NO 219
<211> LENGTH: 10
<212> TYPE: PRT
<213> ORGANISM: artificial
<220> FEATURE:
<223> OTHER INFORMATION: L2 fragment

<400> SEQUENCE: 219

Asp Val Ile Pro Lys Val Glu Gly Asp Thr
 1               5                  10

<210> SEQ ID NO 220
<211> LENGTH: 10
<212> TYPE: PRT
<213> ORGANISM: artificial
<220> FEATURE:
<223> OTHER INFORMATION: L2 fragment

<400> SEQUENCE: 220

Asp Ile Ile Pro Arg Val Glu Gln Asn Thr
 1               5                  10

<210> SEQ ID NO 221
<211> LENGTH: 10
<212> TYPE: PRT
<213> ORGANISM: artificial
<220> FEATURE:
<223> OTHER INFORMATION: L2 fragment

<400> SEQUENCE: 221

Asp Ile Ile Pro Arg Leu Glu Gln Asn Thr
 1               5                  10

<210> SEQ ID NO 222
<211> LENGTH: 10
<212> TYPE: PRT
<213> ORGANISM: artificial
<220> FEATURE:
<223> OTHER INFORMATION: L2 fragment

<400> SEQUENCE: 222

Asp Ile Ile Pro Arg Val Glu Gln Asp Thr
 1               5                  10

<210> SEQ ID NO 223
<211> LENGTH: 10
<212> TYPE: PRT
<213> ORGANISM: artificial
<220> FEATURE:
<223> OTHER INFORMATION: L2 fragment

<400> SEQUENCE: 223

Asp Ile Ile Pro Arg Val Glu Gln Asp Thr
 1               5                  10

<210> SEQ ID NO 224
<211> LENGTH: 10
<212> TYPE: PRT
<213> ORGANISM: artificial
<220> FEATURE:
<223> OTHER INFORMATION: L2 fragment

<400> SEQUENCE: 224

Asp Ile Ile Pro Lys Val Glu Gln Lys Thr
 1               5                  10
```

```
<210> SEQ ID NO 225
<211> LENGTH: 10
<212> TYPE: PRT
<213> ORGANISM: artificial
<220> FEATURE:
<223> OTHER INFORMATION: L2 fragment

<400> SEQUENCE: 225

Asp Val Ile Pro Lys Val Glu Gly Ser Thr
1               5                   10

<210> SEQ ID NO 226
<211> LENGTH: 10
<212> TYPE: PRT
<213> ORGANISM: artificial
<220> FEATURE:
<223> OTHER INFORMATION: L2 fragment

<400> SEQUENCE: 226

Asp Ile Ile Pro Lys Val Glu His Asn Thr
1               5                   10

<210> SEQ ID NO 227
<211> LENGTH: 10
<212> TYPE: PRT
<213> ORGANISM: artificial
<220> FEATURE:
<223> OTHER INFORMATION: L2 fragment

<400> SEQUENCE: 227

Asp Val Ile Pro Lys Val Glu Gln Asn Thr
1               5                   10

<210> SEQ ID NO 228
<211> LENGTH: 10
<212> TYPE: PRT
<213> ORGANISM: artificial
<220> FEATURE:
<223> OTHER INFORMATION: L2 fragment

<400> SEQUENCE: 228

Asp Val Ile Pro Lys Val Glu His Asn Thr
1               5                   10

<210> SEQ ID NO 229
<211> LENGTH: 10
<212> TYPE: PRT
<213> ORGANISM: artificial
<220> FEATURE:
<223> OTHER INFORMATION: L2 fragment

<400> SEQUENCE: 229

Asp Val Ile Asn Lys Val Glu His Thr Thr
1               5                   10

<210> SEQ ID NO 230
<211> LENGTH: 10
<212> TYPE: PRT
<213> ORGANISM: artificial
<220> FEATURE:
<223> OTHER INFORMATION: L2 fragment

<400> SEQUENCE: 230

Asp Val Arg Asn Lys Val Glu Gly Thr Thr
1               5                   10
```

```
<210> SEQ ID NO 231
<211> LENGTH: 10
<212> TYPE: PRT
<213> ORGANISM: artificial
<220> FEATURE:
<223> OTHER INFORMATION: L2 fragment

<400> SEQUENCE: 231

Asp Val Lys Asn Lys Val Glu Ala Asp Thr
1               5                   10

<210> SEQ ID NO 232
<211> LENGTH: 10
<212> TYPE: PRT
<213> ORGANISM: artificial
<220> FEATURE:
<223> OTHER INFORMATION: L2 fragment

<400> SEQUENCE: 232

Asp Val Lys Asn Lys Val Glu Ala Asn Thr
1               5                   10

<210> SEQ ID NO 233
<211> LENGTH: 10
<212> TYPE: PRT
<213> ORGANISM: artificial
<220> FEATURE:
<223> OTHER INFORMATION: L2 fragment

<400> SEQUENCE: 233

Asp Val Lys Asn Lys Val Glu Asn Asn Thr
1               5                   10

<210> SEQ ID NO 234
<211> LENGTH: 10
<212> TYPE: PRT
<213> ORGANISM: artificial
<220> FEATURE:
<223> OTHER INFORMATION: L2 fragment

<400> SEQUENCE: 234

Asp Val Lys Asn Lys Val Glu Gln Thr Thr
1               5                   10

<210> SEQ ID NO 235
<211> LENGTH: 10
<212> TYPE: PRT
<213> ORGANISM: artificial
<220> FEATURE:
<223> OTHER INFORMATION: L2 fragment

<400> SEQUENCE: 235

Asp Val Lys Asn Lys Phe Glu Asn Ser Thr
1               5                   10

<210> SEQ ID NO 236
<211> LENGTH: 10
<212> TYPE: PRT
<213> ORGANISM: artificial
<220> FEATURE:
<223> OTHER INFORMATION: L2 fragment

<400> SEQUENCE: 236

Asp Val Gln Asn Lys Phe Glu Gly Asn Thr
1               5                   10
```

```
<210> SEQ ID NO 237
<211> LENGTH: 10
<212> TYPE: PRT
<213> ORGANISM: artificial
<220> FEATURE:
<223> OTHER INFORMATION: L2 fragment

<400> SEQUENCE: 237

Asp Ile Gln Asn Lys Ile Glu Gln Thr Thr
1               5                   10

<210> SEQ ID NO 238
<211> LENGTH: 10
<212> TYPE: PRT
<213> ORGANISM: artificial
<220> FEATURE:
<223> OTHER INFORMATION: L2 fragment

<400> SEQUENCE: 238

Asp Val Ile Lys Arg Tyr Glu Gln Thr Thr
1               5                   10

<210> SEQ ID NO 239
<211> LENGTH: 9
<212> TYPE: PRT
<213> ORGANISM: artificial
<220> FEATURE:
<223> OTHER INFORMATION: L2 fragment

<400> SEQUENCE: 239

Val Ile Asn Lys Val Glu Gln Thr Thr
1               5

<210> SEQ ID NO 240
<211> LENGTH: 9
<212> TYPE: PRT
<213> ORGANISM: artificial
<220> FEATURE:
<223> OTHER INFORMATION: L2 fragment

<400> SEQUENCE: 240

Val Ile Asn Lys Val Glu Gln Ser Thr
1               5

<210> SEQ ID NO 241
<211> LENGTH: 9
<212> TYPE: PRT
<213> ORGANISM: artificial
<220> FEATURE:
<223> OTHER INFORMATION: L2 fragment

<400> SEQUENCE: 241

Val Ile Asn Lys Val Glu Gln Lys Thr
1               5

<210> SEQ ID NO 242
<211> LENGTH: 9
<212> TYPE: PRT
<213> ORGANISM: artificial
<220> FEATURE:
<223> OTHER INFORMATION: L2 fragment

<400> SEQUENCE: 242

Val Leu Asn Lys Val Glu Gln Thr Thr
1               5

<210> SEQ ID NO 243
```

```
<211> LENGTH: 9
<212> TYPE: PRT
<213> ORGANISM: artificial
<220> FEATURE:
<223> OTHER INFORMATION: L2 fragment

<400> SEQUENCE: 243

Val Val Asn Lys Val Glu Gln Thr Thr
1               5

<210> SEQ ID NO 244
<211> LENGTH: 9
<212> TYPE: PRT
<213> ORGANISM: artificial
<220> FEATURE:
<223> OTHER INFORMATION: L2 fragment

<400> SEQUENCE: 244

Val Ile Asn Lys Val Glu Ser Thr Thr
1               5

<210> SEQ ID NO 245
<211> LENGTH: 9
<212> TYPE: PRT
<213> ORGANISM: artificial
<220> FEATURE:
<223> OTHER INFORMATION: L2 fragment

<400> SEQUENCE: 245

Val Ile Asn Lys Val Glu Gln Asn Thr
1               5

<210> SEQ ID NO 246
<211> LENGTH: 9
<212> TYPE: PRT
<213> ORGANISM: artificial
<220> FEATURE:
<223> OTHER INFORMATION: L2 fragment

<400> SEQUENCE: 246

Val Val Pro Lys Val Glu Gly Asp Thr
1               5

<210> SEQ ID NO 247
<211> LENGTH: 9
<212> TYPE: PRT
<213> ORGANISM: artificial
<220> FEATURE:
<223> OTHER INFORMATION: L2 fragment

<400> SEQUENCE: 247

Val Ile Pro Lys Val Glu Gly Asp Thr
1               5

<210> SEQ ID NO 248
<211> LENGTH: 9
<212> TYPE: PRT
<213> ORGANISM: artificial
<220> FEATURE:
<223> OTHER INFORMATION: L2 fragment

<400> SEQUENCE: 248

Ile Ile Pro Arg Val Glu Gln Asn Thr
1               5

<210> SEQ ID NO 249
<211> LENGTH: 9
```

<212> TYPE: PRT
<213> ORGANISM: artificial
<220> FEATURE:
<223> OTHER INFORMATION: L2 fragment

<400> SEQUENCE: 249

Ile Ile Pro Arg Leu Glu Gln Asn Thr
1 5

<210> SEQ ID NO 250
<211> LENGTH: 9
<212> TYPE: PRT
<213> ORGANISM: artificial
<220> FEATURE:
<223> OTHER INFORMATION: L2 fragment

<400> SEQUENCE: 250

Ile Ile Pro Arg Val Glu Gln Asp Thr
1 5

<210> SEQ ID NO 251
<211> LENGTH: 9
<212> TYPE: PRT
<213> ORGANISM: artificial
<220> FEATURE:
<223> OTHER INFORMATION: L2 fragment

<400> SEQUENCE: 251

Val Ile Pro Lys Val Glu Gly Thr Thr
1 5

<210> SEQ ID NO 252
<211> LENGTH: 9
<212> TYPE: PRT
<213> ORGANISM: artificial
<220> FEATURE:
<223> OTHER INFORMATION: L2 fragment

<400> SEQUENCE: 252

Ile Ile Pro Lys Val Glu Gln Lys Thr
1 5

<210> SEQ ID NO 253
<211> LENGTH: 9
<212> TYPE: PRT
<213> ORGANISM: artificial
<220> FEATURE:
<223> OTHER INFORMATION: L2 fragment

<400> SEQUENCE: 253

Val Ile Pro Lys Val Glu Gly Ser Thr
1 5

<210> SEQ ID NO 254
<211> LENGTH: 9
<212> TYPE: PRT
<213> ORGANISM: artificial
<220> FEATURE:
<223> OTHER INFORMATION: L2 fragment

<400> SEQUENCE: 254

Ile Ile Pro Lys Val Glu His Asn Thr
1 5

<210> SEQ ID NO 255
<211> LENGTH: 9
<212> TYPE: PRT

```
<213> ORGANISM: artificial
<220> FEATURE:
<223> OTHER INFORMATION: L2 fragment

<400> SEQUENCE: 255

Val Ile Pro Lys Val Gl

```
<220> FEATURE:
<223> OTHER INFORMATION: L2 fragment

<400> SEQUENCE: 261

Val Lys Asn Lys Val Glu Asn Asn Thr
1               5

<210> SEQ ID NO 262
<211> LENGTH: 9
<212> TYPE: PRT
<213> ORGANISM: artificial
<220> FEATURE:
<223> OTHER INFORMATION: L2 fragment

<400> SEQUENCE: 262

Val Lys Asn Lys Val Glu Gln Thr Thr
1               5

<210> SEQ ID NO 263
<211> LENGTH: 9
<212> TYPE: PRT
<213> ORGANISM: artificial
<220> FEATURE:
<223> OTHER INFORMATION: L2 fragment

<400> SEQUENCE: 263

Val Lys Asn Lys Phe Glu Asn Ser Thr
1               5

<210> SEQ ID NO 264
<211> LENGTH: 9
<212> TYPE: PRT
<213> ORGANISM: artificial
<220> FEATURE:
<223> OTHER INFORMATION: L2 fragment

<400> SEQUENCE: 264

Val Gln Asn Lys Phe Glu Gly Asn Thr
1               5

<210> SEQ ID NO 265
<211> LENGTH: 9
<212> TYPE: PRT
<213> ORGANISM: artificial
<220> FEATURE:
<223> OTHER INFORMATION: L2 fragment

<400> SEQUENCE: 265

Ile Gln Asn Lys Ile Glu Gln Thr Thr
1               5

<210> SEQ ID NO 266
<211> LENGTH: 9
<212> TYPE: PRT
<213> ORGANISM: artificial
<220> FEATURE:
<223> OTHER INFORMATION: L2 fragment

<400> SEQUENCE: 266

Val Ile Lys Arg Tyr Glu Gln Thr Thr
1               5

<210> SEQ ID NO 267
<211> LENGTH: 8
<212> TYPE: PRT
<213> ORGANISM: artificial
<220> FEATURE:
```

```
<223> OTHER INFORMATION: L2 fragment

<400> SEQUENCE: 267

Ile Asn Lys Val Glu Gln Thr Thr
1               5

<210> SEQ ID NO 268
<211> LENGTH: 8
<212> TYPE: PRT
<213> ORGANISM: artificial
<220> FEATURE:
<223> OTHER INFORMATION: L2 fragment

<400> SEQUENCE: 268

Ile Asn Lys Val Glu Gln Thr Thr
1               5

<210> SEQ ID NO 269
<211> LENGTH: 8
<212> TYPE: PRT
<213> ORGANISM: artificial
<220> FEATURE:
<223> OTHER INFORMATION: L2 fragment

<400> SEQUENCE: 269

Ile Asn Lys Val Glu Gln Lys Thr
1               5

<210> SEQ ID NO 270
<211> LENGTH: 8
<212> TYPE: PRT
<213> ORGANISM: artificial
<220> FEATURE:
<223> OTHER INFORMATION: L2 fragment

<400> SEQUENCE: 270

Leu Asn Lys Val Glu Gln Thr Thr
1               5

<210> SEQ ID NO 271
<211> LENGTH: 8
<212> TYPE: PRT
<213> ORGANISM: artificial
<220> FEATURE:
<223> OTHER INFORMATION: L2 fragment

<400> SEQUENCE: 271

Val Asn Lys Val Glu Gln Thr Thr
1               5

<210> SEQ ID NO 272
<211> LENGTH: 8
<212> TYPE: PRT
<213> ORGANISM: artificial
<220> FEATURE:
<223> OTHER INFORMATION: L2 fragment

<400> SEQUENCE: 272

Ile Asn Lys Val Glu Ser Thr Thr
1               5

<210> SEQ ID NO 273
<211> LENGTH: 8
<212> TYPE: PRT
<213> ORGANISM: artificial
<220> FEATURE:
<223> OTHER INFORMATION: L2 fragment
```

```
<400> SEQUENCE: 273

Ile Asn Lys Val Glu Gln Asn Thr
1               5

<210> SEQ ID NO 274
<211> LENGTH: 8
<212> TYPE: PRT
<213> ORGANISM: artificial
<220> FEATURE:
<223> OTHER INFORMATION: L2 fragment

<400> SEQUENCE: 274

Val Pro Lys Val Glu Gly Asp Thr
1               5

<210> SEQ ID NO 275
<211> LENGTH: 8
<212> TYPE: PRT
<213> ORGANISM: artificial
<220> FEATURE:
<223> OTHER INFORMATION: L2 fragment

<400> SEQUENCE: 275

Ile Pro Lys Val Glu Gly Asp Thr
1               5

<210> SEQ ID NO 276
<211> LENGTH: 8
<212> TYPE: PRT
<213> ORGANISM: artificial
<220> FEATURE:
<223> OTHER INFORMATION: L2 fragment

<400> SEQUENCE: 276

Ile Pro Arg Val Glu Gln Asn Thr
1               5

<210> SEQ ID NO 277
<211> LENGTH: 8
<212> TYPE: PRT
<213> ORGANISM: artificial
<220> FEATURE:
<223> OTHER INFORMATION: L2 fragment

<400> SEQUENCE: 277

Ile Pro Arg Leu Glu Gln Asn Thr
1               5

<210> SEQ ID NO 278
<211> LENGTH: 8
<212> TYPE: PRT
<213> ORGANISM: artificial
<220> FEATURE:
<223> OTHER INFORMATION: L2 fragment

<400> SEQUENCE: 278

Ile Pro Arg Val Glu Gln Asp Thr
1               5

<210> SEQ ID NO 279
<211> LENGTH: 8
<212> TYPE: PRT
<213> ORGANISM: artificial
<220> FEATURE:
<223> OTHER INFORMATION: L2 fragment
```

```
<400> SEQUENCE: 279

Ile Pro Lys Val Glu Gly Thr Thr
1               5

<210> SEQ ID NO 280
<211> LENGTH: 8
<212> TYPE: PRT
<213> ORGANISM: artificial
<220> FEATURE:
<223> OTHER INFORMATION: L2 fragment

<400> SEQUENCE: 280

Ile Pro Lys Val Glu His Lys Thr
1               5

<210> SEQ ID NO 281
<211> LENGTH: 8
<212> TYPE: PRT
<213> ORGANISM: artificial
<220> FEATURE:
<223> OTHER INFORMATION: L2 fragment

<400> SEQUENCE: 281

Ile Pro Lys Val Glu Gly Ser Thr
1               5

<210> SEQ ID NO 282
<211> LENGTH: 8
<212> TYPE: PRT
<213> ORGANISM: artificial
<220> FEATURE:
<223> OTHER INFORMATION: L2 fragment

<400> SEQUENCE: 282

Ile Pro Lys Val Glu His Asn Thr
1               5

<210> SEQ ID NO 283
<211> LENGTH: 8
<212> TYPE: PRT
<213> ORGANISM: artificial
<220> FEATURE:
<223> OTHER INFORMATION: L2 fragment

<400> SEQUENCE: 283

Ile Pro Lys Val Glu Gln Asn Thr
1               5

<210> SEQ ID NO 284
<211> LENGTH: 8
<212> TYPE: PRT
<213> ORGANISM: artificial
<220> FEATURE:
<223> OTHER INFORMATION: L2 fragment

<400> SEQUENCE: 284

Ile Asn Lys Val Glu His Thr Thr
1               5

<210> SEQ ID NO 285
<211> LENGTH: 8
<212> TYPE: PRT
<213> ORGANISM: artificial
<220> FEATURE:
<223> OTHER INFORMATION: L2 fragment

<400> SEQUENCE: 285
```

Arg Asn Lys Val Glu Gly Thr Thr
1               5

<210> SEQ ID NO 286
<211> LENGTH: 8
<212> TYPE: PRT
<213> ORGANISM: artificial
<220> FEATURE:
<223> OTHER INFORMATION: L2 fragment

<400> SEQUENCE: 286

Lys Asn Lys Val Glu Ala Asp Thr
1               5

<210> SEQ ID NO 287
<211> LENGTH: 8
<212> TYPE: PRT
<213> ORGANISM: artificial
<220> FEATURE:
<223> OTHER INFORMATION: L2 fragment

<400> SEQUENCE: 287

Lys Asn Lys Val Glu Ala Asn Thr
1               5

<210> SEQ ID NO 288
<211> LENGTH: 8
<212> TYPE: PRT
<213> ORGANISM: artificial
<220> FEATURE:
<223> OTHER INFORMATION: L2 fragment

<400> SEQUENCE: 288

Lys Asn Lys Val Glu Asn Asn Thr
1               5

<210> SEQ ID NO 289
<211> LENGTH: 8
<212> TYPE: PRT
<213> ORGANISM: artificial
<220> FEATURE:
<223> OTHER INFORMATION: L2 fragment

<400> SEQUENCE: 289

Lys Asn Lys Val Glu Gln Thr Thr
1               5

<210> SEQ ID NO 290
<211> LENGTH: 8
<212> TYPE: PRT
<213> ORGANISM: artificial
<220> FEATURE:
<223> OTHER INFORMATION: L2 fragment

<400> SEQUENCE: 290

Lys Asn Lys Phe Glu Asn Ser Thr
1               5

<210> SEQ ID NO 291
<211> LENGTH: 8
<212> TYPE: PRT
<213> ORGANISM: artificial
<220> FEATURE:
<223> OTHER INFORMATION: L2 fragment

<400> SEQUENCE: 291

```
Lys Asn Lys Phe Glu Asn Ser Thr
1               5

<210> SEQ ID NO 292
<211> LENGTH: 8
<212> TYPE: PRT
<213> ORGANISM: artificial
<220> FEATURE:
<223> OTHER INFORMATION: L2 fragment

<400> SEQUENCE: 292

Gln Asn Lys Ile Glu Gln Thr Thr
1               5

<210> SEQ ID NO 293
<211> LENGTH: 8
<212> TYPE: PRT
<213> ORGANISM: artificial
<220> FEATURE:
<223> OTHER INFORMATION: L2 fragment

<400> SEQUENCE: 293

Ile Lys Arg Tyr Glu Gln Thr Thr
1               5

<210> SEQ ID NO 294
<211> LENGTH: 9
<212> TYPE: PRT
<213> ORGANISM: artificial
<220> FEATURE:
<223> OTHER INFORMATION: L2 fragment

<400> SEQUENCE: 294

Thr Gly Tyr Ile Pro Leu Gln Thr Arg
1               5

<210> SEQ ID NO 295
<211> LENGTH: 9
<212> TYPE: PRT
<213> ORGANISM: artificial
<220> FEATURE:
<223> OTHER INFORMATION: L2 fragment

<400> SEQUENCE: 295

Thr Gly Tyr Val Pro Leu Gly Ser Thr
1               5

<210> SEQ ID NO 296
<211> LENGTH: 9
<212> TYPE: PRT
<213> ORGANISM: artificial
<220> FEATURE:
<223> OTHER INFORMATION: L2 fragment

<400> SEQUENCE: 296

Thr Gly Tyr Val Pro Leu Gly Asn Thr
1               5

<210> SEQ ID NO 297
<211> LENGTH: 9
<212> TYPE: PRT
<213> ORGANISM: artificial
<220> FEATURE:
<223> OTHER INFORMATION: L2 fragment

<400> SEQUENCE: 297

Thr Gly Tyr Val Pro Leu Ser Thr Gly
```

<210> SEQ ID NO 298
<211> LENGTH: 9
<212> TYPE: PRT
<213> ORGANISM: artificial
<220> FEATURE:
<223> OTHER INFORMATION: L2 fragment

<400> SEQUENCE: 298

Thr Gly Tyr Ile Pro Leu Gln Ser Thr
1               5

<210> SEQ ID NO 299
<211> LENGTH: 9
<212> TYPE: PRT
<213> ORGANISM: artificial
<220> FEATURE:
<223> OTHER INFORMATION: L2 fragment

<400> SEQUENCE: 299

Thr Gly Tyr Val Pro Val Gly Ser Thr
1               5

<210> SEQ ID NO 300
<211> LENGTH: 9
<212> TYPE: PRT
<213> ORGANISM: artificial
<220> FEATURE:
<223> OTHER INFORMATION: L2 fragment

<400> SEQUENCE: 300

Thr Gly Tyr Val Pro Leu Gln Thr Ser
1               5

<210> SEQ ID NO 301
<211> LENGTH: 9
<212> TYPE: PRT
<213> ORGANISM: artificial
<220> FEATURE:
<223> OTHER INFORMATION: L2 fragment

<400> SEQUENCE: 301

Thr Gly Tyr Val Pro Leu Thr Thr Gly
1               5

<210> SEQ ID NO 302
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 302

Arg Gly Cys Lys Gln Xaa Gly Thr Cys Pro Pro Asp Val Ile Asn Lys
1               5                   10                  15

Val Glu Gln

<210> SEQ ID NO 303
<211> LENGTH: 19
<212> TYPE: PRT
<213> ORGANISM: artificial
<220> FEATURE:

<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 303

Arg Gly Cys Lys Ala Xaa Asn Thr Cys Pro Pro Asp Val Ile Asn Lys
1               5                   10                  15

Val Glu Gln

<210> SEQ ID NO 304
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represent Gly or Ala

<400> SEQUENCE: 304

Arg Gly Cys Lys Ala Xaa Gly Thr Cys Pro Pro Asp Val Ile Asn Lys
1               5                   10                  15

Val Glu Gln

<210> SEQ ID NO 305
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 305

Gln Ser Cys Lys Ala Xaa Gly Thr Cys Pro Pro Asp Val Leu Asn Lys
1               5                   10                  15

Val Glu Gln

<210> SEQ ID NO 306
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 306

Gln Ser Cys Lys Ala Xaa Gly Thr Cys Pro Pro Asp Val Val Asn Lys
1               5                   10                  15

Val Glu Gln

<210> SEQ ID NO 307
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE

```
<222> LOCATION: (6)..(6)
<223> OTHER INFORMATION: Xaa represents Gly or Ala

<400> SEQUENCE: 307

Gln Thr Cys Lys Gln Xaa Gly Thr Cys Pro Pro Asp Val Ile Asn Lys
1               5                   10                  15

Val Glu Gln

<210> SEQ ID NO 308
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 308

Gln Thr Cys Lys Gln Xaa Gly Thr Cys Pro Pro Asp Val Ile Asn Lys
1               5                   10                  15

Val Glu Gln

<210> SEQ ID NO 309
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 309

Arg Thr Cys Lys Gln Xaa Gly Thr Cys Pro Pro Asp Val Ile Asn Lys
1               5                   10                  15

Val Glu Ser

<210> SEQ ID NO 310
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 310

Arg Thr Cys Lys Gln Xaa Gly Thr Cys Pro Pro Asp Val Ile Asn Lys
1               5                   10                  15

Val Glu Gln

<210> SEQ ID NO 311
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala
```

```
<400> SEQUENCE: 311

Lys Gly Cys Lys Ala Xaa Gly Thr Cys Pro Pro Asp Val Ile Asn Lys
1               5                   10                  15

Val Glu Gln

<210> SEQ ID NO 312
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 312

Arg Thr Cys Lys Gln Xaa Gly Thr Cys Pro Pro Asp Val Val Pro Lys
1               5                   10                  15

Val Glu Gly

<210> SEQ ID NO 313
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 313

Arg Thr Cys Lys Gln Xaa Gly Thr Cys Pro Pro Asp Val Ile Pro Lys
1               5                   10                  15

Val Glu Gly

<210> SEQ ID NO 314
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 314

Arg Thr Cys Lys Val Xaa Gly Thr Cys Pro Ala Asp Val Val Pro Lys
1               5                   10                  15

Val Glu Gly

<210> SEQ ID NO 315
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 315

Arg Thr Cys Lys Ala Xaa Gly Thr Arg Pro Ala Asp Val Ile Pro Lys
```

```
1               5                   10                  15
Val Glu Gly

<210> SEQ ID NO 316
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 316

Ser Thr Cys Lys Ala Xaa Gly Thr Cys Pro Pro Asp Val Ile Pro Lys
1               5                   10                  15

Leu Glu Gly

<210> SEQ ID NO 317
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 317

Arg Thr Cys Lys Gln Xaa Gly Thr Cys Pro Pro Asp Ile Ile Pro Arg
1               5                   10                  15

Leu Glu Gln

<210> SEQ ID NO 318
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 318

Arg Thr Cys Lys Gln Xaa Gly Thr Cys Pro Pro Asp Ile Ile Pro Arg
1               5                   10                  15

Val Glu Gln

<210> SEQ ID NO 319
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 319

Lys Thr Cys Lys Val Xaa Gly Thr Cys Pro Pro Asp Val Ile Pro Lys
1               5                   10                  15

Val Glu Gly
```

```
<210> SEQ ID NO 320
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 320

Lys Thr Cys Lys Ala Xaa Gly Thr Cys Pro Pro Asp Val Ile Pro Lys
 1               5                  10                  15

Val Glu Gly

<210> SEQ ID NO 321
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 321

Ser Thr Cys Lys Ala Xaa Gly Thr Cys Pro Pro Asp Val Ile Pro Lys
 1               5                  10                  15

Val Glu Gly

<210> SEQ ID NO 322
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 322

Arg Thr Cys Lys Ala Xaa Gly Thr Cys Pro Pro Asp Val Ile Pro Lys
 1               5                  10                  15

Val Glu Gly

<210> SEQ ID NO 323
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 323

Ser Thr Cys Lys Ala Xaa Gly Thr Cys Pro Ala Asp Val Ile Pro Lys
 1               5                  10                  15

Val Glu Gly

<210> SEQ ID NO 324
```

```
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 324

Lys Thr Cys Lys Leu Xaa Gly Thr Cys Pro Glu Asp Val Ile Asn Lys
1               5                   10                  15

Val Glu Gln

<210> SEQ ID NO 325
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 325

Lys Thr Cys Lys Gln Xaa Gly Thr Cys Pro Pro Asp Ile Ile Pro Lys
1               5                   10                  15

Ile Glu Gly

<210> SEQ ID NO 326
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 326

Lys Thr Cys Lys Gln Xaa Gly Thr Cys Pro Pro Asp Ile Val Pro Lys
1               5                   10                  15

Val Glu Gly

<210> SEQ ID NO 327
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 327

Ser Thr Cys Lys Gln Xaa Gly Thr Cys Pro Pro Asp Ile Ile Pro Arg
1               5                   10                  15

Val Glu Gln

<210> SEQ ID NO 328
<211> LENGTH: 19
<212> TYPE: PRT
<213> ORGANISM: artificial
```

```
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 328

Lys Thr Cys Lys Gln Xaa Gly Thr Cys Pro Pro Asp Val Ile Pro Lys
1               5                   10                  15

Val Glu Gly

<210> SEQ ID NO 329
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 329

Gln Thr Cys Lys Ala Xaa Gly Thr Cys Pro Ser Asp Ile Ile Pro Lys
1               5                   10                  15

Val Glu His

<210> SEQ ID NO 330
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 330

Gln Thr Cys Lys Ala Xaa Gly Thr Cys Pro Pro Asp Val Ile Pro Lys
1               5                   10                  15

Val Glu Gln

<210> SEQ ID NO 331
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 331

Gln Thr Cys Lys Leu Xaa Gly Thr Cys Pro Pro Asp Val Ile Pro Lys
1               5                   10                  15

Val Glu His

<210> SEQ ID NO 332
<211> LENGTH: 19
<212> TYPE: PRT
<213> ORGANISM: artificial
<220> FEATURE:
<223> OTHER INFORMATION: L2 fragment
<220> FEATURE:
```

-continued

```
<221> NAME/KEY: MISC_FEATURE
<222> LOCATION: (6)..(6)
<223> OTHER INFORMATION: Xaa represents Gly or Ala

<400> SEQUENCE: 332

Gln Thr Cys Lys Ala Xaa Gly Thr Cys Pro Ser Asp Val Ile Asn Lys
1               5                   10                  15

Val Glu His

<210> SEQ ID NO 333
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represenst Gly or Ala

<400> SEQUENCE: 333

Lys Gln Cys Gln Leu Xaa Ala Asp Cys Pro Pro Asp Val Arg Asn Lys
1               5                   10                  15

Val Glu Gly

<210> SEQ ID NO 334
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 334

Ala Lys Cys Gln Leu Xaa Gly Asn Cys Leu Pro Asp Val Lys Asn Lys
1               5                   10                  15

Val Glu Ala

<210> SEQ ID NO 335
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 335

Ala Lys Cys Gln Leu Xaa Gly Asp Cys Leu Pro Asp Val Lys Asn Lys
1               5                   10                  15

Val Glu Ala

<210> SEQ ID NO 336
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala
```

<400> SEQUENCE: 336

Arg His Cys Ala Leu Xaa Gly Thr Cys Pro Asp Asp Val Lys Asn Lys
1               5                   10                  15

Val Glu Asn

<210> SEQ ID NO 337
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 337

Lys His Cys Ala Gly Xaa Gly Thr Cys Pro Glu Asp Val Lys Asn Lys
1               5                   10                  15

Val Glu Gln

<210> SEQ ID NO 338
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 338

Lys Thr Cys Leu Gln Xaa Gly Asp Cys Ile Pro Asp Val Lys Asn Lys
1               5                   10                  15

Phe Glu Asn

<210> SEQ ID NO 339
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 339

Arg Ser Cys Leu Gln Xaa Gly Asp Cys Ile Pro Asp Val Gln Asn Lys
1               5                   10                  15

Phe Glu Gly

<210> SEQ ID NO 340
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 340

-continued

Gln Thr Cys Lys Ala Xaa Gly Thr Cys Pro Pro Asp Val Ile Pro Lys
1               5                   10                  15

Val Glu Gly

<210> SEQ ID NO 341
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 341

Lys Thr Cys Lys Gln Xaa Gly Thr Cys Pro Pro Asp Val Val Pro Lys
1               5                   10                  15

Val Glu Gly

<210> SEQ ID NO 342
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 342

Arg Thr Cys Lys Gln Xaa Gly Thr Cys Pro Pro Asp Val Ile Asn Lys
1               5                   10                  15

Val Glu Gly

<210> SEQ ID NO 343
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 343

Lys Thr Cys Lys Gln Xaa Gly Thr Cys Pro Ser Asp Val Ile Asn Lys
1               5                   10                  15

Val Glu Gly

<210> SEQ ID NO 344
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 344

Lys Thr Cys Lys Leu Xaa Gly Thr Cys Pro Glu Asp Val Val Asn Lys
1               5                   10                  15

Ile Glu Gln

<210> SEQ ID NO 345
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 345

Arg Thr Cys Lys Gln Xaa Gly Thr Cys Pro Pro Asp Val Val Asp Lys
1               5                   10                  15

Val Glu Gly

<210> SEQ ID NO 346
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 346

Ser Thr Cys Lys Ala Xaa Gly Thr Cys Pro Pro Asp Val Val Asn Lys
1               5                   10                  15

Val Glu Gly

<210> SEQ ID NO 347
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 347

Pro Thr Cys Lys Ile Xaa Gly Asn Cys Pro Ala Asp Ile Gln Asn Lys
1               5                   10                  15

Phe Glu Asn

<210> SEQ ID NO 348
<211> LENGTH: 19
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 348

Pro Ala Cys Lys Ile Xaa Asn Thr Cys Pro Pro Asp Ile Ile Asn Lys
1               5                   10                  15

Tyr Glu Asn

```
<210> SEQ ID NO 349
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 349

Arg Gly Cys Lys Gln Xaa Gly Thr Cys Pro Pro Asp
1               5                   10

<210> SEQ ID NO 350
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 350

Arg Gly Cys Lys Ala Xaa Asn Thr Cys Pro Pro Asp
1               5                   10

<210> SEQ ID NO 351
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represent Gly or Ala

<400> SEQUENCE: 351

Arg Gly Cys Lys Ala Xaa Gly Thr Cys Pro Pro Asp
1               5                   10

<210> SEQ ID NO 352
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 352

Gln Ser Cys Lys Ala Xaa Gly Thr Cys Pro Pro Asp
1               5                   10

<210> SEQ ID NO 353
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala
```

<400> SEQUENCE: 353

Gln Thr Cys Lys Gln Xaa Gly Thr Cys Pro Pro Asp
1               5                   10

<210> SEQ ID NO 354
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 354

Arg Thr Cys Lys Gln Xaa Gly Thr Cys Pro Pro Asp
1               5                   10

<210> SEQ ID NO 355
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represent Gly or Ala

<400> SEQUENCE: 355

Lys Gly Cys Lys Ala Xaa Gly Thr Cys Pro Pro Asp
1               5                   10

<210> SEQ ID NO 356
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 356

Pro Thr Cys Lys Ala Xaa Gly Thr Cys Pro Pro Asp
1               5                   10

<210> SEQ ID NO 357
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 357

Arg Thr Cys Lys Val Xaa Gly Thr Cys Pro Ala Asp
1               5                   10

<210> SEQ ID NO 358
<211> LENGTH: 12
<212> TYPE: PRT
<213> ORGANISM: artificial
<220> FEATURE:

```
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 358

Arg Thr Cys Lys Ala Xaa Gly Thr Arg Pro Ala Asp
1               5                   10

<210> SEQ ID NO 359
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 359

Lys Thr Cys Lys Val Xaa Gly Thr Cys Pro Pro Asp
1               5                   10

<210> SEQ ID NO 360
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 360

Lys Thr Cys Lys Ala Xaa Gly Thr Cys Pro Pro Asp
1               5                   10

<210> SEQ ID NO 361
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 361

Arg Thr Cys Lys Ala Xaa Gly Thr Cys Pro Pro Asp
1               5                   10

<210> SEQ ID NO 362
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 362

Ser Thr Cys Lys Ala Xaa Gly Thr Arg Pro Pro Asp
1               5                   10
```

<210> SEQ ID NO 363
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 363

Ser Thr Cys Lys Ala Xaa Gly Thr Cys Pro Ala Asp
1               5                   10

<210> SEQ ID NO 364
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 364

Lys Thr Cys Lys Leu Xaa Gly Thr Cys Pro Glu Asp
1               5                   10

<210> SEQ ID NO 365
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 365

Ala Thr Cys Lys Gln Xaa Gly Thr Cys Pro Pro Asp
1               5                   10

<210> SEQ ID NO 366
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 366

Ser Thr Cys Lys Gln Xaa Gly Thr Cys Pro Pro Asp
1               5                   10

<210> SEQ ID NO 367
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 367

Gln Thr Cys Lys Ala Xaa Gly Thr Cys Pro Ser Asp
1               5                   10

<210> SEQ ID NO 368
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 368

Gln Thr Cys Lys Leu Xaa Gly Thr Cys Pro Pro Asp
1               5                   10

<210> SEQ ID NO 369
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 369

Lys Gln Cys Gln Leu Xaa Ala Asp Cys Pro Pro Asp
1               5                   10

<210> SEQ ID NO 370
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 370

Ala Lys Cys Gln Leu Xaa Gly Asn Cys Leu Pro Asp
1               5                   10

<210> SEQ ID NO 371
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 371

Ala Lys Cys Gln Leu Xaa Gly Asp Cys Leu Pro Asp
1               5                   10

<210> SEQ ID NO 372
<211> LENGTH: 12
<212> TYPE: PRT
<213> ORGANISM: artificial

```
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 372

Arg His Cys Ala Leu Xaa Gly Thr Cys Pro Asp Asp
1               5                   10

<210> SEQ ID NO 373
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 373

Lys His Cys Ala Gly Xaa Gly Thr Cys Pro Glu Asp
1               5                   10

<210> SEQ ID NO 374
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 374

Lys Thr Cys Leu Gln Xaa Gly Asp Cys Ile Pro Asp
1               5                   10

<210> SEQ ID NO 375
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 375

Arg Ser Cys Leu Gln Xaa Gly Asp Cys Ile Pro Asp
1               5                   10

<210> SEQ ID NO 376
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 376

Gln Thr Cys Lys Ala Xaa Gly Thr Cys Pro Pro Asp
1               5                   10
```

<210> SEQ ID NO 377
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 377

Lys Thr Cys Lys Gln Xaa Gly Thr Cys Pro Glu Asp
1               5                   10

<210> SEQ ID NO 378
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 378

Lys Thr Cys Lys Gln Xaa Gly Thr Cys Pro Ser Asp
1               5                   10

<210> SEQ ID NO 379
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 379

Lys Thr Cys Lys Gln Xaa Gly Thr Cys Pro Ser Asp
1               5                   10

<210> SEQ ID NO 380
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)
<223> OTHER INFORMATION: Xaa represents Gly or Ala

<400> SEQUENCE: 380

Pro Thr Cys Lys Ile Xaa Gly Asn Cys Pro Ala Asp
1               5                   10

<210> SEQ ID NO 381
<211> LENGTH: 12
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (6)..(6)

<223> OTHER INFORMATION: Xaa represents Gly or Ala

<400> SEQUENCE: 381

Pro Ala Cys Lys Ile Xaa Asn Thr Cys Pro Pro Asp
1               5                   10

<210> SEQ ID NO 382
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 382

Gly Cys Lys Gln Xaa Gly Thr Cys Pro Pro Asp
1               5                   10

<210> SEQ ID NO 383
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 383

Gly Cys Lys Ala Xaa Asn Thr Cys Pro Pro Asp
1               5                   10

<210> SEQ ID NO 384
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 384

Ala Cys Lys Ala Xaa Gly Thr Cys Pro Pro Asp
1               5                   10

<210> SEQ ID NO 385
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 385

Ser Cys Lys Ala Xaa Gly Thr Cys Pro Pro Asp
1               5                   10

<210> SEQ ID NO 386
<211> LENGTH: 11
<212> TYPE: PRT

```
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 386

Lys Cys Lys Ala Xaa Gly Thr Cys Ile Pro Asp
1               5                   10

<210> SEQ ID NO 387
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 387

Gly Cys Lys Ala Xaa Gly Thr Cys Pro Pro Asp
1               5                   10

<210> SEQ ID NO 388
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 388

Lys Cys Lys Ala Xaa Gly Thr Cys Pro Pro Asp
1               5                   10

<210> SEQ ID NO 389
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 389

Thr Cys Lys Val Xaa Gly Thr Cys Pro Ala Asp
1               5                   10

<210> SEQ ID NO 390
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 390

Thr Cys Lys Ala Xaa Gly Thr Arg Pro Ala Asp
```

```
1               5                   10
```

<210> SEQ ID NO 391
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 391

```
Thr Cys Lys Val Xaa Gly Thr Cys Pro Pro Asp
1               5                   10
```

<210> SEQ ID NO 392
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 392

```
Ser Cys Lys Leu Xaa Gly Thr Cys Pro Pro Asp
1               5                   10
```

<210> SEQ ID NO 393
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 393

```
Ser Cys Lys Gln Xaa Gly Thr Cys Pro Ser Asp
1               5                   10
```

<210> SEQ ID NO 394
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 394

```
Thr Cys Lys Ala Xaa Gly Thr Cys Pro Ala Asp
1               5                   10
```

<210> SEQ ID NO 395
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE

```
<222> LOCATION: (5)..(5)
<223> OTHER INFORMATION: Xaa represents Gly or Ala

<400> SEQUENCE: 395

Thr Cys Lys Leu Xaa Gly Thr Cys Pro Glu Asp
1               5                   10

<210> SEQ ID NO 396
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 396

Thr Cys Lys Ala Xaa Gly Thr Cys Pro Ser Asp
1               5                   10

<210> SEQ ID NO 397
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 397

Thr Cys Lys Leu Xaa Gly Thr Cys Pro Pro Asp
1               5                   10

<210> SEQ ID NO 398
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 398

Gln Cys Gln Leu Xaa Ala Asp Cys Pro Pro Asp
1               5                   10

<210> SEQ ID NO 399
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 399

Lys Cys Gln Leu Xaa Gly Asn Cys Leu Pro Asp
1               5                   10

<210> SEQ ID NO 400
<211> LENGTH: 11
```

<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 400

Lys Cys Gln Leu Xaa G

```
Thr Cys Leu Gln Xaa Gly Asp Cys Ile Pro Asp
1               5                   10
```

<210> SEQ ID NO 405
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 405

```
Thr Cys Lys Ala Xaa Gly Thr Cys Pro Pro Asp
1               5                   10
```

<210> SEQ ID NO 406
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 406

```
Thr Cys Lys Gln Xaa Gly Thr Cys Pro Ser Asp
1               5                   10
```

<210> SEQ ID NO 407
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 407

```
Thr Cys Lys Ile Xaa Gly Asn Cys Pro Ala Asp
1               5                   10
```

<210> SEQ ID NO 408
<211> LENGTH: 11
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 408

```
Thr Cys Lys Ile Xaa Gly Asn Cys Pro Ala Asp
1               5                   10
```

<210> SEQ ID NO 409
<211> LENGTH: 10
<212> TYPE: PRT
<213> ORGANISM: artificial
<220> FEATURE:
<223> OTHER INFORMATION: L2 fragment
<220> FEATURE:

```
<221> NAME/KEY: MISC_FEATURE
<222> LOCATION: (4)..(4)
<223> OTHER INFORMATION: Xaa represent Gly or Ala

<400> SEQUENCE: 409

Cys Lys Gln Xaa Gly Thr Cys Pro Asp Asp
1               5                   10

<210> SEQ ID NO 410
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 410

Cys Lys Ala Xaa Asn Thr Cys Pro Pro Asp
1               5                   10

<210> SEQ ID NO 411
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 411

Cys Leu Ala Xaa Gly Thr Cys Pro Ala Asp
1               5                   10

<210> SEQ ID NO 412
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 412

Cys Leu Ala Xaa Gly Thr Cys Pro Pro Asp
1               5                   10

<210> SEQ ID NO 413
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 413

Cys Lys Leu Xaa Gly Thr Cys Pro Ala Asp
1               5                   10

<210> SEQ ID NO 414
```

```
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 414

Cys Lys Val Xaa Gly Thr Cys Pro Ala Asp
1               5                   10

<210> SEQ ID NO 415
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 415

Cys Lys Ala Xaa Gly Thr Arg Pro Ala Asp
1               5                   10

<210> SEQ ID NO 416
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 416

Cys Lys Ala Xaa Gly Thr Arg Pro Ala Asp
1               5                   10

<210> SEQ ID NO 417
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 417

Cys Lys Ala Xaa Gly Thr Cys Pro Ala Asp
1               5                   10

<210> SEQ ID NO 418
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 418
```

```
Cys Lys Leu Xaa Gly Thr Cys Pro Glu Asp
1               5                   10

<210> SEQ ID NO 419
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: L2 fragment

<400> SEQUENCE: 419

Cys Lys Ala Xaa Gly Thr Cys Pro Ser Asp
1               5                   10

<210> SEQ ID NO 420
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 420

Cys Lys Leu Xaa Gly Thr Cys Pro Pro Asp
1               5                   10

<210> SEQ ID NO 421
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 421

Cys Gln Leu Xaa Ala Asp Cys Pro Pro Asp
1               5                   10

<210> SEQ ID NO 422
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 422

Cys Gln Leu Xaa Gly Asn Cys Leu Pro Asp
1               5                   10

<210> SEQ ID NO 423
<211> LENGTH: 10
<212> TYPE: PRT
<213> ORGANISM: artificial
<220> FEATURE:
<223> OTHER INFORMATION: L2 fragment
```

```
<220> FEATURE:
<221> NAME/KEY: MISC_FEATURE
<222> LOCATION: (4)..(4)
<223> OTHER INFORMATION: Xaa represents Gly or Ala

<400> SEQUENCE: 423

Cys Gln Leu Xaa Gly Asp Cys Leu Pro Asp
1               5                   10

<210> SEQ ID NO 424
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 424

Cys Ala Leu Xaa Gly Thr Cys Pro Asp Asp
1               5                   10

<210> SEQ ID NO 425
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 425

Cys Ala Gly Xaa Gly Thr Cys Pro Glu Asp
1               5                   10

<210> SEQ ID NO 426
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 426

Cys Leu Gln Xaa Gly Asp Cys Ile Pro Asp
1               5                   10

<210> SEQ ID NO 427
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 427

Cys Lys Ala Xaa Gly Thr Cys Pro Pro Asp
1               5                   10
```

```
<210> SEQ ID NO 428
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 428

Cys Lys Gln Xaa Gly Thr Cys Pro Ser Asp
1               5                   10

<210> SEQ ID NO 429
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 429

Cys Lys Ile Xaa Gly Asn Cys Pro Ala Asp
1               5                   10

<210> SEQ ID NO 430
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 430

Cys Lys Ile Xaa Asn Thr Cys Pro Pro Asp
1               5                   10

<210> SEQ ID NO 431
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala
<220> FEATURE:
<221> NAME/KEY: MISC_FEATURE
<222> LOCATION: (5)..(5)
<223> OTHER INFORMATION: Xaa represents Gly or Ala

<400> SEQUENCE: 431

Gly Cys Lys Gln Xaa Gly Thr Cys Pro Pro
1               5                   10

<210> SEQ ID NO 432
<211> LENGTH: 10
<212> TYPE: PRT
<213> ORGANISM: artificial
<220> FEATURE:
<223> OTHER INFORMATION: L2 fragment
<220> FEATURE:
```

```
<221> NAME/KEY: MISC_FEATURE
<222> LOCATION: (5)..(5)
<223> OTHER INFORMATION: Xaa represents Gly or Ala

<400> SEQUENCE: 432

Gly Cys Lys Ala Xaa Asn Thr Cys Pro Pro
1               5                   10

<210> SEQ ID NO 433
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 433

Gly Cys Lys Ala Xaa Gly Thr Cys Pro Pro
1               5                   10

<210> SEQ ID NO 434
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 434

Ser Cys Lys Ala Xaa Gly Thr Cys Pro Pro
1               5                   10

<210> SEQ ID NO 435
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 435

Thr Cys Lys Gln Xaa Gly Thr Cys Pro Pro
1               5                   10

<210> SEQ ID NO 436
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 436

Gly Cys Lys Ala Xaa Gly Thr Cys Pro Pro
1               5                   10

<210> SEQ ID NO 437
```

```
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 437

Thr Cys Lys Gln Xaa Gly Thr Cys Pro Pro
1               5                   10

<210> SEQ ID NO 438
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 438

Thr Cys Lys Val Xaa Gly Thr Cys Pro Ala
1               5                   10

<210> SEQ ID NO 439
<211> LENGTH: 10
<212> TYPE: PRT
<213> ORGANISM: artificial
<220> FEATURE:
<223> OTHER INFORMATION: Xaa represents Gly or Ala
<220> FEATURE:
<221> NAME/KEY: misc_feature
<222> LOCATION: (5)..(5)
<223> OTHER INFORMATION: Xaa can be any naturally occurring amino acid

<400> SEQUENCE: 439

Thr Cys Lys Ala Xaa Gly Thr Arg Pro Ala
1               5                   10

<210> SEQ ID NO 440
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 440

Thr Cys Lys Val Xaa Gly Thr Cys Pro Pro
1               5                   10

<210> SEQ ID NO 441
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 441
```

Thr Cys Lys Ala Xaa Gly Thr Cys Pro Pro
1               5                   10

<210> SEQ ID NO 442
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 442

Thr Cys Lys Ala Xaa Gly Thr Cys Pro Pro
1               5                   10

<210> SEQ ID NO 443
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 443

Thr Cys Lys Ala Xaa Gly Thr Cys Pro Ala
1               5                   10

<210> SEQ ID NO 444
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 444

Thr Cys Lys Leu Xaa Gly Thr Cys Pro Glu
1               5                   10

<210> SEQ ID NO 445
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 445

Thr Cys Lys Ala Xaa Gly Thr Cys Pro Ser
1               5                   10

<210> SEQ ID NO 446
<211> LENGTH: 10
<212> TYPE: PRT
<213> ORGANISM: artificial
<220> FEATURE:
<223> OTHER INFORMATION: L2 fragment

```
<220> FEATURE:
<221> NAME/KEY: MISC_FEATURE
<222> LOCATION: (5)..(5)
<223> OTHER INFORMATION: Xaa represents Gly or Ala

<400> SEQUENCE: 446

Thr Cys Lys Leu Xaa Gly Thr Cys Pro Pro
1               5                   10

<210> SEQ ID NO 447
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 447

Gln Cys Gln Leu Xaa Ala Asp Cys Pro Pro
1               5                   10

<210> SEQ ID NO 448
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 448

Lys Cys Gln Leu Xaa Gly Asn Cys Leu Pro
1               5                   10

<210> SEQ ID NO 449
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 449

Lys Cys Gln Leu Xaa Gly Asp Cys Leu Pro
1               5                   10

<210> SEQ ID NO 450
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 450

His Cys Ala Leu Xaa Gly Thr Cys Pro Asp
1               5                   10
```

```
<210> SEQ ID NO 451
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 451

His Cys Ala Gly Xaa Gly Thr Cys Pro Glu
1               5                   10

<210> SEQ ID NO 452
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 452

Thr Cys Leu Gln Xaa Gly Asp Cys Ile Pro
1               5                   10

<210> SEQ ID NO 453
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 453

Ser Cys Leu Gln Xaa Gly Asp Cys Ile Pro
1               5                   10

<210> SEQ ID NO 454
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 454

Thr Cys Lys Ala Xaa Gly Thr Cys Pro Pro
1               5                   10

<210> SEQ ID NO 455
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala
```

<400> SEQUENCE: 455

Thr Cys Lys Gln Xaa Gly Thr Cys Pro Ser
1               5                   10

<210> SEQ ID NO 456
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 456

Thr Cys Lys Ile Xaa Gly Asn Cys Pro Ala
1               5                   10

<210> SEQ ID NO 457
<211> LENGTH: 10
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (5)..(5)
<223> OTHER INFORMATION: Xaa represents Gly or Ala

<400> SEQUENCE: 457

Ala Cys Lys Ile Xaa Asn Thr Cys Pro Pro
1               5                   10

<210> SEQ ID NO 458
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 458

Cys Lys Gln Xaa Gly Thr Cys Pro Pro
1               5

<210> SEQ ID NO 459
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 459

Cys Lys Ala Xaa Asn Thr Cys Pro Pro
1               5

<210> SEQ ID NO 460
<211> LENGTH: 9
<212> TYPE: PRT
<213> ORGANISM: artificial
<220> FEATURE:

<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 460

Cys Lys Ala Xaa Gly Thr Cys Pro Pro
1               5

<210> SEQ ID NO 461
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 461

Cys Lys Ala Xaa Gly Thr Cys Pro Pro
1               5

<210> SEQ ID NO 462
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 462

Cys Lys Gln Xaa Gly Thr Cys Pro Pro
1               5

<210> SEQ ID NO 463
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 463

Cys Lys Val Xaa Gly Thr Cys Pro Ala
1               5

<210> SEQ ID NO 464
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 464

Cys Lys Ala Xaa Gly Thr Arg Pro Ala
1               5

```
<210> SEQ ID NO 465
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 465

Cys Lys Val Xaa Gly Thr Cys Pro Pro
1               5

<210> SEQ ID NO 466
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 466

Cys Lys Ala Xaa Gly Thr Cys Pro Ala
1               5

<210> SEQ ID NO 467
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 467

Cys Lys Leu Xaa Gly Thr Cys Pro Glu
1               5

<210> SEQ ID NO 468
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 468

Cys Lys Ala Xaa Gly Thr Cys Pro Ser
1               5

<210> SEQ ID NO 469
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala
```

-continued

<400> SEQUENCE: 469

Cys Lys Leu Xaa Gly Thr Cys Pro Pro
1               5

<210> SEQ ID NO 470
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 470

Cys Gln Leu Xaa Ala Asp Cys Pro Pro
1               5

<210> SEQ ID NO 471
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 471

Cys Gln Leu Xaa Gly Asn Cys Leu Pro
1               5

<210> SEQ ID NO 472
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 472

Cys Gln Leu Xaa Gly Asp Cys Leu Pro
1               5

<210> SEQ ID NO 473
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 473

Cys Ala Leu Xaa Gly Thr Cys Pro Asp
1               5

<210> SEQ ID NO 474
<211> LENGTH: 9
<212> TYPE: PRT
<213> ORGANISM: artificial

```
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 474

Cys Ala Gly Xaa Gly Thr Cys Pro Glu
1               5

<210> SEQ ID NO 475
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 475

Cys Leu Gln Xaa Gly Asp Cys Ile Pro
1               5

<210> SEQ ID NO 476
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 476

Cys Lys Ala Xaa Gly Thr Cys Pro Pro
1               5

<210> SEQ ID NO 477
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 477

Cys Lys Gln Xaa Gly Thr Cys Pro Ser
1               5

<210> SEQ ID NO 478
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 478

Cys Lys Ile Xaa Gly Asn Cys Pro Ala
1               5
```

<210> SEQ ID NO 479
<211> LENGTH: 9
<212> TYPE: PRT
<213> ORGANISM: artificial
<220> FEATURE:
<223> OTHER INFORMATION: L2 fragment
<220> FEATURE:
<221> NAME/KEY: MISC_FEATURE
<222> LOCATION: (4)..(4)
<223> OTHER INFORMATION: Xaa represents Gly or Ala

<400> SEQUENCE: 479

Cys Lys Ile Xaa Asn Thr Cys Pro Pro
1               5

<210> SEQ ID NO 480
<211> LENGTH: 6
<212> TYPE: PRT
<213> ORGANISM: artificial
<220> FEATURE:
<223> OTHER INFORMATION: loop site of FN3

<400> SEQUENCE: 480

Pro Ala Val Thr Val Arg
1               5

<210> SEQ ID NO 481
<211> LENGTH: 9
<212> TYPE: PRT
<213> ORGANISM: artificial
<220> FEATURE:
<223> OTHER INFORMATION: loop site of FN3

<400> SEQUENCE: 481

Gly Arg Gly Asp Ser Pro Ala Ser Ser
1               5

<210> SEQ ID NO 482
<211> LENGTH: 7
<212> TYPE: PRT
<213> ORGANISM: artificial
<220> FEATURE:
<223> OTHER INFORMATION: loop site of bilin-binding protein

<400> SEQUENCE: 482

Pro Asn Ser Val Glu Lys Tyr
1               5

<210> SEQ ID NO 483
<211> LENGTH: 5
<212> TYPE: PRT
<213> ORGANISM: artificial
<220> FEATURE:
<223> OTHER INFORMATION: loop site of bilin-binding protein

<400> SEQUENCE: 483

Ile His Gly Lys Glu
1               5

<210> SEQ ID NO 484
<211> LENGTH: 7
<212> TYPE: PRT
<213> ORGANISM: artificial
<220> FEATURE:
<223> OTHER INFORMATION: loop-site of bilin-binding protein

<400> SEQUENCE: 484

Thr Tyr Gly Gly Val Thr Lys
1               5

<210> SEQ ID NO 485
<211> LENGTH: 5
<212> TYPE: PRT
<213> ORGANISM: artificial
<220> FEATURE:
<223> OTHER INFORMATION: loop-site

<400> SEQUENCE: 485

Tyr Lys Gly Gln Pro
1               5

<210> SEQ ID NO 486
<211> LENGTH: 19
<212> TYPE: PRT
<213> ORGANISM: Human papillomavirus type 18

<400> SEQUENCE: 486

Lys Thr Cys Lys Gln Ser Gly Thr Cys Pro Ser Asp Val Val Asn Lys
1               5                   10                  15

Val Glu Gly

<210> SEQ ID NO 487
<211> LENGTH: 19
<212> TYPE: PRT
<213> ORGANISM: Human papillomavirus type 31

<400> SEQUENCE: 487

Gln Thr Cys Lys Ala Ala Gly Thr Cys Pro Ser Asp Val Ile Pro Lys
1               5                   10                  15

Ile Glu His

<210> SEQ ID NO 488
<211> LENGTH: 19
<212> TYPE: PRT
<213> ORGANISM: Human papillomavirus type 68

<400> SEQUENCE: 488

Lys Thr Cys Lys Gln Ser Gly Thr Cys Pro Pro Asp Val Ile Asp Lys
1               5                   10                  15

Val Glu Gly

<210> SEQ ID NO 489
<211> LENGTH: 19
<212> TYPE: PRT
<213> ORGANISM: Human Paillomavirus Type 82

<400> SEQUENCE: 489

Ser Thr Cys Lys Ala Ala Gly Thr Cys Pro Pro Asp Val Ile Pro Lys
1               5                   10                  15

Val Lys Gly

<210> SEQ ID NO 490
<211> LENGTH: 12
<212> TYPE: PRT
<213> ORGANISM: Human papillomavirus type 18

<400> SEQUENCE: 490

Lys Thr Cys Lys Gln Ser Gly Thr Cys Pro Ser Asp
1               5                   10

<210> SEQ ID NO 491
<211> LENGTH: 195
<212> TYPE: PRT
<213> ORGANISM: Artificial Sequence
<220> FEATURE:
<223> OTHER INFORMATION: (SEQ ID NO:2)x3+ (SEQ ID NO: 487)x3 +(SEQ ID
    NO:77)x3 with tripeptide (GGP) linkers

<400> SEQUENCE: 491

```
Lys Thr Cys Lys Gln Ala Gly Thr Cys Pro Pro Asp Ile Ile Pro Lys
1               5                   10                  15

Val Glu Gly Gly Gly Pro Lys Thr Cys Lys Gln Ala Gly Thr Cys Pro
            20                  25                  30

Pro Asp Ile Ile Pro Lys Val Glu Gly Gly Gly Pro Lys Thr Cys Lys
        35                  40                  45

Gln Ala Gly Thr Cys Pro Pro Asp Ile Ile Pro Lys Val Glu Gly Gly
    50                  55                  60

Gly Pro Gln Thr Cys Lys Ala Ala Gly Thr Cys Pro Ser Asp Val Ile
65                  70                  75                  80

Pro Lys Ile Glu His Gly Gly Pro Gln Thr Cys Lys Ala Ala Gly Thr
                85                  90                  95

Cys Pro Ser Asp Val Ile Pro Lys Ile Glu His Gly Gly Pro Gln Thr
            100                 105                 110

Cys Lys Ala Ala Gly Thr Cys Pro Ser Asp Val Ile Pro Lys Ile Glu
        115                 120                 125

His Gly Gly Pro Ser Thr Cys Lys Ala Ala Gly Thr Cys Pro Pro Asp
    130                 135                 140

Val Val Asn Lys Val Glu Gly Gly Pro Ser Thr Cys Lys Ala Ala
145                 150                 155                 160

Gly Thr Cys Pro Pro Asp Val Val Asn Lys Val Glu Gly Gly Pro
                165                 170                 175

Ser Thr Cys Lys Ala Ala Gly Thr Cys Pro Pro Asp Val Val Asn Lys
            180                 185                 190

Val Glu Gly
        195
```

<210> SEQ ID NO 492
<211> LENGTH: 195
<212> TYPE: PRT
<213> ORGANISM: Artificial Sequence
<220> FEATURE:
<223> OTHER INFORMATION: ((SEQ ID NO:2)+ (SEQ ID NO:487) +(SEQ ID
    NO:77))x3 with tripeptide (GGP) linkers

<400> SEQUENCE: 492

```
Lys Thr Cys Lys Gln Ala Gly Thr Cys Pro Pro Asp Ile Ile Pro Lys
1               5                   10                  15

Val Glu Gly Gly Gly Pro Gln Thr Cys Lys Ala Ala Gly Thr Cys Pro
            20                  25                  30

Ser Asp Val Ile Pro Lys Ile Glu His Gly Gly Pro Ser Thr Cys Lys
        35                  40                  45

Ala Ala Gly Thr Cys Pro Pro Asp Val Val Asn Lys Val Glu Gly Gly
    50                  55                  60

Gly Pro Lys Thr Cys Lys Gln Ala Gly Thr Cys Pro Pro Asp Ile Ile
65                  70                  75                  80

Pro Lys Val Glu Gly Gly Gly Pro Gln Thr Cys Lys Ala Ala Gly Thr
                85                  90                  95
```

```
Cys Pro Ser Asp Val Ile Pro Lys Ile Glu His Gly Gly Pro Ser Thr
                100                 105                 110

Cys Lys Ala Ala Gly Thr Cys Pro Pro Asp Val Val Asn Lys Val Glu
            115                 120                 125

Gly Gly Gly Pro Lys Thr Cys Lys Gln Ala Gly Thr Cys Pro Pro Asp
130                 135                 140

Ile Ile Pro Lys Val Glu Gly Gly Pro Gln Thr Cys Lys Ala Ala
145                 150                 155                 160

Gly Thr Cys Pro Ser Asp Val Ile Pro Lys Ile Glu His Gly Gly Pro
                165                 170                 175

Ser Thr Cys Lys Ala Ala Gly Thr Cys Pro Pro Asp Val Val Asn Lys
            180                 185                 190

Val Glu Gly
        195

<210> SEQ ID NO 493
<211> LENGTH: 100
<212> TYPE: PRT
<213> ORGANISM: Pyrococcus furiosus

<400> SEQUENCE: 493

Met Ile Ile Glu Tyr Asp Gly Glu Ile Asp Phe Thr Lys Gly Arg Val
1               5                   10                  15

Val Leu Trp Phe Ser Ile Pro Gly Cys Gly Pro Cys Arg Leu Val Glu
            20                  25                  30

Arg Phe Met Thr Glu Leu Ser Gly Tyr Phe Glu Asp Ile Gln Ile Val
        35                  40                  45

His Ile Asn Ala Gly Lys Trp Lys Asn Ile Val Asp Lys Phe Asn Ile
    50                  55                  60

Leu Asn Val Pro Thr Leu Val Tyr Leu Lys Asp Gly Arg Glu Val Gly
65                  70                  75                  80

Arg Gln Asn Leu Ile Arg Ser Lys Glu Glu Ile Leu Lys Lys Leu Lys
                85                  90                  95

Glu Leu Gln Glu
            100

<210> SEQ ID NO 494
<211> LENGTH: 101
<212> TYPE: PRT
<213> ORGANISM: Thermococcus kodakarensis

<400> SEQUENCE: 494

Met Ile Val Glu Tyr Asp Glu Asn Val Asp Phe Thr Lys Gly Lys Ala
1               5                   10                  15

Val Leu Trp Phe Ser Ile Pro Gly Cys Gly Pro Cys Arg Leu Val Glu
            20                  25                  30

Ala Phe Met Lys Glu Leu Ser Glu Glu Phe Gly Glu Ile Ala Ile Val
        35                  40                  45

His Val Asn Ala Glu Lys Trp Ser Gly Leu Val Glu Gly Phe Arg Ile
    50                  55                  60

Leu Asn Val Pro Thr Leu Val Tyr Leu Lys Asp Gly Lys Glu Val Ala
65                  70                  75                  80

Arg Gln Asn Leu Ile Arg Gly Lys Gly Glu Val Leu Ile Lys Phe Glu
                85                  90                  95

Glu Pro Arg Glu Leu
            100
```

<210> SEQ ID NO 495
<211> LENGTH: 105
<212> TYPE: PRT
<213> ORGANISM: Thermococcus onnurineus

<400> SEQUENCE: 495

Met Ile Arg Glu Phe Asp Gly Asp Phe Gly Lys Val Glu Arg Ala Lys
1               5                   10                  15

Tyr Ala Leu Leu Trp Phe Ser Ser Pro Gly Cys Gly Pro Cys Arg Met
            20                  25                  30

Ile Glu Pro Phe Met His Glu Leu Ser Glu Glu Tyr Lys Glu Val Glu
        35                  40                  45

Phe Trp Glu Val Asp Val Glu Lys His Leu Pro Leu Ala Glu Lys Phe
50                  55                  60

Asp Val Met Asn Val Pro Thr Leu Ile Tyr Leu Lys Glu Gly Asn Glu
65                  70                  75                  80

Ile Ala Arg Gln Asn Leu Val Arg Lys Glu Glu Val Glu Glu Lys
                85                  90                  95

Leu Met Met Leu Leu Gly Ser Asp Ser
            100                 105

<210> SEQ ID NO 496
<211> LENGTH: 100
<212> TYPE: PRT
<213> ORGANISM: Thermococcus sibiricus

<400> SEQUENCE: 496

Met Ile His Glu Tyr Asp Gly Lys Ile Asp Phe Asn Arg Gly Lys Val
1               5                   10                  15

Val Leu Trp Phe Ser Ile Gln Gly Cys Gly Pro Cys Arg Leu Val Glu
            20                  25                  30

Ser Phe Met Glu Glu Val Ser Glu Glu Phe Ser Glu Ile Arg Phe Ile
        35                  40                  45

His Val Gly Ala Glu Lys Trp Ser Asn Ile Val Lys Arg Phe Glu Val
50                  55                  60

Leu Asn Val Pro Thr Leu Val Tyr Leu Lys Asp Gly Lys Glu Val Ala
65                  70                  75                  80

Arg Gln Asn Leu Ile Arg Ser Lys Glu Glu Val Leu Ala Lys Ile Glu
                85                  90                  95

Glu Leu His Glu
            100

<210> SEQ ID NO 497
<211> LENGTH: 253
<212> TYPE: PRT
<213> ORGANISM: Artificial Sequence
<220> FEATURE:
<223> OTHER INFORMATION: Dimer of Escherichia coli thioredoxin variants

<400> SEQUENCE: 497

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
            35                  40                  45

Glu Tyr Gln Gly Lys Leu Thr Val Ala Lys Leu Asn Ile Asp Gln Asn

```
                    50                  55                  60
Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Gly Gly
            100                 105                 110

Gly Ser Glu Gly Gly Gly Ser Glu Gly Gly Gly Ser Glu Gly Gly Gly
            115                 120                 125

Ser Glu Gly Gly Gly Ser Glu Gly Gly Gly Ser Glu Gly Gly Gly Met
130                 135                 140

Ser Asp Lys Ile Ile His Leu Thr Asp Asp Ser Phe Asp Thr Asp Val
145                 150                 155                 160

Leu Lys Ala Asp Gly Ala Ile Leu Val Asp Phe Trp Ala Glu Trp Cys
                165                 170                 175

Gly Pro Gly Cys Lys Met Ile Ala Pro Ile Leu Asp Glu Ile Ala Asp
            180                 185                 190

Glu Tyr Gln Gly Lys Leu Thr Val Ala Lys Leu Asn Ile Asp Gln Asn
            195                 200                 205

Pro Gly Thr Ala Pro Lys Tyr Gly Ile Arg Gly Ile Pro Thr Leu Leu
210                 215                 220

Leu Phe Lys Asn Gly Glu Val Ala Ala Thr Lys Val Gly Ala Leu Ser
225                 230                 235                 240

Lys Gly Gln Leu Lys Glu Phe Leu Asp Ala Asn Leu Ala
                245                 250

<210> SEQ ID NO 498
<211> LENGTH: 396
<212> TYPE: PRT
<213> ORGANISM: Artificial
<220> FEATURE:
<223> OTHER INFORMATION: Trimer of Escherichia coli thioredoxin variants

<400> SEQUENCE: 498

Met Ser Asp Lys Ile Ile His Leu Thr Asp Asp Ser Phe Asp Thr Asp
  1               5                  10                  15

Val Leu Lys Ala Asp Gly Ala Ile Leu Val Asp Phe Trp Ala Glu Trp
                 20                  25                  30

Cys Gly Pro Gly Cys Lys Met Ile Ala Pro Ile Leu Asp Glu Ile Ala Asp
             35                  40                  45

Glu Tyr Gln Gly Lys Leu Thr Val Ala Lys Leu Asn Ile Asp Gln Asn
 50                  55                  60

Pro Gly Thr Ala Pro Lys Tyr Gly Ile Arg Gly Ile Pro Thr Leu Leu
 65                  70                  75                  80

Leu Phe Lys Asn Gly Glu Val Ala Ala Thr Lys Val Gly Ala Leu Ser
                 85                  90                  95

Lys Gly Gln Leu Lys Glu Phe Leu Asp Ala Asn Leu Ala Gly Gly Gly
            100                 105                 110

Gly Ser Glu Gly Gly Gly Ser Glu Gly Gly Gly Ser Glu Gly Gly Gly
            115                 120                 125

Ser Glu Gly Gly Gly Ser Glu Gly Gly Gly Ser Glu Gly Gly Gly Met
130                 135                 140

Ser Asp Lys Ile Ile His Leu Thr Asp Asp Ser Phe Asp Thr Asp Val
145                 150                 155                 160

Leu Lys Ala Asp Gly Ala Ile Leu Val Asp Phe Trp Ala Glu Trp Cys
```

-continued

```
                165                 170                 175
Gly Pro Gly Cys Lys Met Ile Ala Pro Ile Leu Asp Glu Ile Ala Asp
            180                 185                 190

Glu Tyr Gln Gly Lys Leu Thr Val Ala Lys Leu Asn Ile Asp Gln Asn
            195                 200                 205

Pro Gly Thr Ala Pro Lys Tyr Gly Ile Arg Gly Ile Pro Thr Leu Leu
            210                 215                 220

Leu Phe Lys Asn Gly Glu Val Ala Ala Thr Lys Val Gly Ala Leu Ser
225                 230                 235                 240

Lys Gly Gln Leu Lys Glu Phe Leu Asp Ala Asn Leu Ala Gly Gly Gly
                245                 250                 255

Gly Ser Glu Gly Gly Gly Ser Glu Gly Gly Gly Ser Glu Gly Gly Gly
            260                 265                 270

Ser Glu Gly Gly Gly Ser Glu Gly Gly Gly Ser Glu Gly Gly Gly Met
            275                 280                 285

Ser Asp Lys Ile Ile His Leu Thr Asp Asp Ser Phe Asp Thr Asp Val
            290                 295                 300

Leu Lys Ala Asp Gly Ala Ile Leu Val Asp Phe Trp Ala Glu Trp Cys
305                 310                 315                 320

Leu Ser Cys Lys Met Ile Ala Pro Ile Leu Asp Glu Ile Ala Asp Glu
                325                 330                 335

Tyr Gln Gly Lys Leu Thr Val Ala Lys Leu Asn Ile Asp Gln Asn Pro
            340                 345                 350

Gly Thr Ala Pro Lys Tyr Gly Ile Arg Gly Ile Pro Thr Leu Leu Leu
            355                 360                 365

Phe Lys Asn Gly Glu Val Ala Ala Thr Lys Val Gly Ala Leu Ser Lys
    370                 375                 380

Gly Gln Leu Lys Glu Phe Leu Asp Ala Asn Leu Ala
385                 390                 395
```

IMMUNOGENIC POLYPEPTIDES COMPRISING A SCAFFOLD POLYPEPTIDE AND A L2 POLYPEPTIDE OR A FRAGMENT THEREOF

The present invention relates to an immunogenic polypeptide comprising a) a scaffold polypeptide, and b) a L2 polypeptide or a fragment of said L2 polypeptide, wherein said scaffold polypeptide constrains the structure of said L2 polypeptide, or of the fragment of said L2 polypeptide. Moreover, the present invention relates to a vaccine comprising said immunogenic polypeptide. The present invention is also concerned with a method for producing an antibody against human papillomavirus. Also encompassed by the present invention is an antibody obtained by carrying out the said method.

Cervical cancer is women's second most frequent cancer worldwide. Clinical and molecular studies have shown that certain types of human papillomavirus (HPV), referred to as high-risk types, are the etiological agents of this disease. Two anti-HPV vaccines for the prophylaxis of cervical cancer have been licensed recently by Merck (Gardasil™) and GlaxoSmithKline (Cervarix™) (Schmiedeskamp et al, (2006) Human papillomavirus vaccines. Ann Pharmacother, 40, 1344-1352). Both vaccines rely on the major capsid protein L1 in the form of virus-like particles (VLPs) as antigen (Roden et al., (2006) How will HPV vaccines affect cervical cancer? Nat Rev Cancer, 6, 753-763); they protect against the HPV types from which the L1-VLPs were derived, yet are largely ineffective against all but the most closely related HPV types. The two most prominent high-risk HPV types, 16 and 18, are the major targets of both vaccines, although there is evidence for partial cross-protection against HPV types 31 and 45 (reviewed by Muller and Gissmann, (2007) A long way: history of the prophylactic papillomavirus vaccine. Dis Markers, 23, 331-336; Huh and Roden, (2008) The future of vaccines for cervical cancer. Gynecol Oncol, 109, S48-56). The limited cross-protective capacity of L1-based vaccines, which is the main reason for the continuing effort toward the development of improved vaccination strategies, likely reflects the HPV type specificity of L1 neutralizing epitopes (Giroglou et al., (2001) Immunological analyses of human papillomavirus capsids. Vaccine, 19, 1783-1793).

Antibodies against the minor capsid protein L2 also neutralize HPV infection and are often capable to cross-neutralize various non-cognate virions, although with varying efficiencies (Kondo et al. 2007, Neutralization of HPV16, 18, 31, and 58 pseudovirions with antisera induced by immunizing rabbits with synthetic peptides representing segments of the HPV16 minor capsid protein L2 surface region. Virology, 358, 266-272; Gambhira, R., (2007) A protective and broadly cross-neutralizing epitope of human papillomavirus L2. J Virol, 81, 13927-13931). The N-terminal region of L2 interacts with an as yet unidentified secondary receptor on the surface of target cells (Yang et al. (2003) Cell surface-binding motifs of L2 that facilitate papillomavirus infection. J Virol, 77, 3531-3541) and this interaction can be blocked by anti-L2 antibodies. The precise identity of the L2 region involved in HPV-cell surface interaction is still a matter of debate. This was initially proposed as the region comprised of amino acids (aa) 108-120, and antibodies targeting this particular L2 region were indeed shown to block viral infection in vitro albeit at low titers (Kawana et al. (2001) Nasal immunization of mice with peptide having a cross-neutralization epitope on minor capsid protein L2 of human papillomavirus type 16 elicit systemic and mucosal antibodies. Vaccine, 19, 1496-1502; Kawana et al. (2001b) Human papillomavirus type 16 minor capsid protein L2 N-terminal region containing a common neutralization epitope binds to the cell surface and enters the cytoplasm. J Virol, 75, 2331-2336). Subsequent experiments identified additional neutralizing epitopes in the aa 1-88 region (Pastrana et al. (2005) Cross-neutralization of cutaneous and mucosal Papillomavirus types with anti-sera to the amino terminus of L2. Virology, 337, 365-372) as well as in more extended N-terminal regions comprised of aa 11-200 and aa 18-144 (Kondo loc. cit). Perhaps the most prominent of these N-terminal epitopes is the one located between aa 17-36. This was identified as the target of an HPV16 neutralizing and protective monoclonal antibody (RG-1) as well as the major determinant of the neutralizing activity found in sera from rabbits and humans immunized with extended versions of L2 (aa 1-88, 11-200 or the full-length protein) (Gambhira, 2007, loc cit.). Since it had been found that mutation of L2 amino acids 18 and 19 or of amino acids 20 and 21 disrupted both L2 binding to the cell surface and viral infection (Yang, R., et al. (2003). Cell surface-binding motifs of L2 that facilitate papillomavirus infection. J. Virol. 77:3531-3541), it was concluded that the epitope recognized by the RG-1 antibody overlaps the surface-binding motif of HPV16 L2.

Besides the lack of precise knowledge on the most relevant (cross) neutralizing epitope(s), a major problem with the use of L2 as a tool for HPV prophylaxis is the poor immunogenicity of the L2 protein and peptides thereof, as compared to L1-VLPs. A substantial increase in immunogenicity has been reported lately via chemical coupling of the HPV16 L2 peptide (17-36) to a broadly recognized T helper epitope and to the Toll-like receptor ligand dipalmitoyl S-glyceryl cysteine (Alphs et al. (2008) Protection against heterologous human papillomavirus challenge by a synthetic lipopeptide vaccine containing a broadly cross-neutralizing epitope of L2. Proc Natl Acad Sci USA, 105, 5850-5855). Alternatively, L2 peptides have been fused to Adenovirus surface proteins (WO 2008/140474) or to other HPV proteins to increase immunogenicity (WO 2002/070004, de Jong et al. (2002), Enhancement of human papillomavirus (HPV) type 16 E6 and E7-specific T-cell immunity in healthy volunteers through vaccination with TA-CIN, an HPV16 L2E7E6 fusion protein vaccine, Vaccine, 20(29-30):3456-3464).

A recently developed alternative strategy for increasing peptide immunogenicity relies on the use of thioredoxin (Trx) as a scaffold protein with the ability to constrain the structure of single-copy as well as multimeric (tandemly repeated) peptide epitopes inserted within its surface-exposed active site loop (Moretto et al. (2007) Conformation-sensitive antibodies against Alzheimer amyloid-beta by immunization with a thioredoxin-constrained B-cell epitope peptide. J Biol Chem, 282, 11436-11445).

Thus, the L1 polypeptide is highly immunogenic and antibodies against it show only a limited cross-protective capacity, whereas antibodies against the L2 polypeptide are capable of cross-neutralizing various HPV genotypes. The L2 polypeptide, however has only limited immunogenicity.

Therefore, immunogenic polypeptides that are highly immunogenic and allow for a cross-neutralization of various HPV genotypes without the drawbacks as referred to above are highly required.

The technical problem underlying the present invention can be seen as the provision of means and methods for complying with the aforementioned needs.

The technical problem is solved by the embodiments characterized in the claims and herein below.

Accordingly, the present invention relates to an immunogenic polypeptide comprising a) a scaffold polypeptide, and
b) a L2 polypeptide having an amino acid sequence as shown in SEQ ID NO:1, or a fragment of said L2 polypeptide,
wherein said scaffold polypeptide constrains the structure of said L2 polypeptide, or of the fragment of said L2 polypeptide.

The term "polypeptide" as used herein relates to a polymer comprising amino acids linked together by peptide bonds. The term "immunogenic polypeptide" is understood by the skilled person. Immunogenic polypeptides, preferably, elicit protective immune response in a host, preferably, in a human. The immunogenic polypeptide in the context of the present invention, preferably, shall allow for establishing or improving immunity to infection with various HPV genotypes. Preferably, the immunogenic polypeptide according to the present invention allows for establishing or improving immunity to infection with human papillomavirus genotypes 16, 18, 31, 45 and 58. Preferably, the said polypeptide also allows for establishing or improving immunity to infection with human papillomavirus genotypes 6, 52, 2, 27, 57 and/or 11. Immunogenic polypeptides are preferred reagents for vaccine compositions.

The term "L2 polypeptide", preferably, refers to the N-terminal region of the full-length L2 polypeptide of HPV16 (human papillomavirus 16). The full-length L2 is one of the two capsid proteins of HPV16 and is frequently also referred to as minor capsid protein. Together with the major capsid protein, L1, the full-length L2 polypeptide forms viral capsids. The L2 polypeptide in the context of the present invention, preferably, comprises the N-terminal amino acids 1 to 120 of the HPV16 L2 polypeptide as shown in SEQ ID NO:1.

The term "fragment" as used herein, preferably, refers to a sub-polypeptide of the L2 polypeptide (as shown in SEQ ID NO:1). Preferably, said fragment comprises at least 7, at least 10, at least 12, at least 15, or at least 20 consecutive amino acid residues of said L2 polypeptide. Preferred fragments of the L2 polypeptide have an amino acid sequence as shown in SEQ ID NO:2 (KTCKQAGTCPPDIIPKVEG), as shown in SEQ ID NO:3 (KTCKQAGTCPPD), as shown in SEQ ID NO:4 (TCKQAGTCPPD), as shown in SEQ ID NO:5 (CKQAGTCPPD), as shown in SEQ ID NO:6 (TCKQAGTCPP), as shown in SEQ ID NO:7 (CKQAGTCPP), as shown in SEQ ID NO:8 (DIIPKVEGKT), as shown in SEQ ID NO:9 (TGYIPLGTR).

The most preferred fragments in the context of the present invention are fragments having a sequence as shown in SEQ ID NO:2 (KTCKQAGTCPPDIIPKVEG, amino acids 20 to 38 of the L2 polypeptide as shown in SEQ ID NO:1)), or as shown in SEQ ID NO:5 (CKQAGTCPPD, amino acids 22 to 31 of the L2 polypeptide as shown in SEQ ID NO:1).

Preferably, the terms "polypeptide" "L2 polypeptide" and "fragment of the L2 polypeptide", respectively, shall also encompass variants of said polypeptide, L2 polypeptide or variants of said fragment of said L2 polypeptide, respectively. Such variants have essentially the same immunological properties as the specific polypeptides, respectively. In particular, they share the same immunological properties if they are detectable by the same specific assays referred to in this specification, e.g., by ELISA assays using polyclonal or monoclonal antibodies specifically recognizing the said polypeptides, respectively. Moreover, it is to be understood that a variant as referred to in accordance with the present invention shall have an amino acid sequence which differs due to at least one amino acid substitution, deletion and/or addition wherein the amino acid sequence of the variant is still, preferably, at least 65%, 70%, 75%, 80%, 85%, 90%, 92%, 95%, 97%, 98%, or 99% identical with the amino acid sequence of the specific polypeptide. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Further included are variants which differ due to posttranslational modifications such as phosphorylation or myristoylation.

As mentioned above, in a preferred embodiment of the present invention the fragment of the L2 polypeptide comprised by the scaffold polypeptide of the immunogenic polypeptide has a sequence as shown in SEQ ID NO:2 (KTCKQAGTCPPDIIPKVEG), or as shown in SEQ ID NO:3 (KTCKQAGTCPPD), or as shown in SEQ ID NO:4 (TCKQAGTCPPD), or as shown in SEQ ID NO:5 (CKQAGTCPPD), or as shown in SEQ ID NO:6 (TCKQAGTCPP), or a sequence as shown in SEQ ID NO:7 (CKQAGTCPP), or a sequence as shown in SEQ ID NO:31 (IIPKVEGKT), or a sequence as shown in SEQ ID NO:32 (IPKVEGKT). Since it has been shown in the context of the present invention that the Alanine (A) residue comprised by the aforementioned fragments can be replaced with other amino acid residues (particularly, with a Glycine (G) residue) without significantly affecting the immunogenicity of the polypeptide according to the invention as well as the neutralizing capacity of the antibodies against the said immunogenic polypeptide (see Examples), variants of the aforementioned fragments preferably have the amino acid sequence as shown in SEQ ID NO:10 (KTCKQXGTCPPDIIPKVEG), or as shown in SEQ ID NO:11 (KTCKQXGTCPPD), or as shown in SEQ ID NO:12 (TCKQXGTCPPD), or as shown in SEQ ID NO:13 (CKQXGTCPPD), or as shown in SEQ ID NO:14 (TCKQXGTCPP), or a sequence as shown in SEQ ID NO:15 (CKQXGTCPP). Preferably, X represents a Glycine (G) or an Alanine (A) residue. Moreover, experiments with the aforementioned fragments of the L2 polypeptide have shown that the most crucial amino acid residues for immunogenicity and for the generation of cross-neutralizing antibodies were amino acid residues 22 to 24 (CKQ) and 26 to 31 (GTCPPD)

of the L2 polypeptide as shown in SEQ ID NO:1 (see Examples). Accordingly, the most preferred variant of a fragment of the L2 polypeptide has a sequence as shown in SEQ ID NO: 13), CKQXGTCPPD).

In one preferred embodiment of the present invention, the immunogenic polypeptide comprises a multimer of the L2 polypeptide or a fragment thereof (or a variant of said L2 polypeptide or a variant of any fragment thereof). Thus, the immunogenic polypeptide shall comprise more than one L2 polypeptide or more than one fragment of the L2 polypeptide. It is particularly envisaged that the immunogenic polypeptide comprises more than one fragment of the L2 polypeptide (or variants thereof). Preferably, the immunogenic polypeptide comprises multimers of 2 to 15 fragments of the L2 polypeptide, and more preferably multimers of 3 to 9 (and, thus, of 3, 4, 5, 6, 7, 8 or 9) fragments of the L2 polypeptide. Most preferably, said immunogenic polypeptide comprises multimers of three or four fragments of the L2 polypeptide. Preferably, said fragments are directly linked together. More preferably, said fragments are linked via a linker peptide (for an explanation of the term "linker peptide", see herein below). Preferably, if the immunogenic polypeptide comprises more than one fragment of the L2 polypeptide, the fragments shall have the same or essentially the same sequence. However, it is also contemplated that the multimer comprises various fragments (or variants thereof) of the L2 polypeptide.

Other preferred L2 fragments (or variants thereof) are selected from the group consisting of SEQ ID NO: 33 to SEQ ID NO:479. SEQ ID NO:33 to SEQ ID NO:479 are also shown in Table 1. The sequences as shown in SEQ ID NO:33 to SEQ ID NO:79 and in SEQ ID NO:486 to SEQ ID NO:489 are variants of the L2 fragment KTCKQAGTCPPDIIPKVEG as shown in SEQ ID NO:2; the sequences as shown in SEQ ID NO:80 to SEQ ID NO:112 and in SEQ ID NO: 490 are variants of the L2 fragment KTCKQAGTCPPD as shown in SEQ ID NO:3; the sequences as shown in SEQ ID NO:113 to SEQ ID NO:139 are variants of the L2 fragment TCKQAGTCPPD as shown in SEQ ID NO:4; the sequences as shown in SEQ ID NO:140 to SEQ ID NO:161 are variants of the L2 fragment CKQAGTCPPD as shown in SEQ ID NO:5; the sequences as shown in SEQ ID NO:162 to SEQ ID NO:188 are variants of the L2 fragment TCKQAGTCPP as shown in SEQ ID NO:6; the sequences as shown in SEQ ID NO:189 to SEQ ID NO:210 are variants of the L2 fragment CKQAGTCPP as shown in SEQ ID NO:7; the sequences as shown in SEQ ID NO:211 to SEQ ID NO:238 are variants of the L2 fragment DIIPKVEGKT as shown in SEQ ID NO:8; the sequences as shown in SEQ ID NO:239 to SEQ ID NO:266 are variants of the L2 fragment IIPKVEGKT as shown in SEQ ID NO:31; the sequences as shown in SEQ ID NO:267 to SEQ ID NO:293 are variants of the L2 fragment IPKVEGKT as shown in SEQ ID NO:32; the sequences as shown in SEQ ID NO:294 to SEQ ID NO:301 are variants of the L2 fragment TGYIPLGTR as shown in SEQ ID NO:9; the sequences as shown in SEQ ID NO:302 to SEQ ID NO:348 are variants of the L2 fragment KTCKQXGTCPPDIIP-KVEG as shown in SEQ ID NO:10; the sequences as shown in SEQ ID NO:349 to SEQ ID NO:381 are variants of the L2 fragment KTCKQXGTCPPD as shown in SEQ ID NO:11; the sequences as shown in SEQ ID NO: 382 to SEQ ID NO: 408 are variants of the L2 fragment TCKQXGTCPPD as shown in SEQ ID NO:12; the sequences as shown in SEQ ID NO: 409 to SEQ ID NO: 430 are variants of the L2 fragment CKQXGTCPPD as shown in SEQ ID NO:13; the sequences as shown in SEQ ID NO: 431 to SEQ ID NO: 457 are variants of the L2 fragment TCKQXGTCPP as shown in SEQ ID NO:14; the sequences as shown in SEQ ID NO:458 to SEQ ID NO:479 are variants of the L2 fragment CKQXGTCPP as shown in SEQ ID NO:15.

As mentioned above, the immunogenic polypeptide shall also comprise a linker peptide or more than one linker peptide. Said linker peptide, preferably, shall prevent the formation of junctional epitopes. Preferably, the linker peptide is positioned at the C- and/or N-Terminus of the L2 polypeptide, or of the fragment (or of the variant thereof). If the immunogenic polypeptide comprises more than one fragment of the L2 polypeptide (or more than one variant of said fragment), it is particularly contemplated that the immunogenic polypeptide comprises a linker peptide between the various fragments (or variants thereof). For example, SEQ ID NO:21 shows a multimer of L2 fragments with a GGP-linker (SEQ ID NO:16) inserted between any one of the L2 fragments.

Preferably, said linker has a length of 1 to 5 amino acids. The person skilled in the art knows how to select suitable linker peptides. Preferably, said 1 to 5 amino acids comprised by said linker peptide are selected from the group consisting of Glycine (G), Proline (P) or Serine (S). A particularly preferred linker peptide comprises the amino acid sequence GGP (SEQ ID NO: 16). However, also other linkers can be used such as GPGP (SEQ ID NO: 17), GPGPG (SEQ ID NO: 18), or SGSG (SEQ ID NO: 19). Preferably, said linker peptide is positioned at the junction of the scaffold polypeptide and the fragment of the L2 polypeptide and/or at the junction of two L2 fragments (or variants thereof). Thus, said linker peptide can be positioned either N-terminally or C-terminally from the L2 fragment (or variant thereof) or both.

A preferred multimer of a fragment of the L2 polypeptide comprised by the immunogenic polypeptide according to the invention has an amino acid sequence such as the one shown in SEQ ID NO: 20, or in SEQ ID NO: 21, or a sequence as shown in SEQ ID NO: 22. Other preferred multimers are multimers comprising combinations of different homooligomers of fragments of the L2 polypeptide (e.g. a trimer of SEQ ID NO:2 linked to a trimer of SEQ ID NO:487 linked to a trimer of SEQ ID NO:487). More preferably, the L2 polypeptides comprised in said multimers are separated by linker sequences, see e.g. SEQ ID NO: 491. Also preferred are repeats of heterooligomers of fragments of the L2 polypeptide. A heterooligomer comprises e.g. SEQ ID NO:2 linked to SEQ ID NO:487 linked to SEQ ID NO:77, the corresponding multimer comprising e.g. said heterooligomer repeated three times. More preferably, the L2 polypeptides comprised in said multimers are separated by linker sequences, see e.g. SEQ ID NO:492.

The L2 polypeptide, or fragment thereof (or the variant of said L2 polypeptide or of the fragment thereof, or the corresponding multimers, see elsewhere herein) shall be comprised by a scaffold polypeptide which constrains the structure of the L2 polypeptide, or the fragment thereof (or the respective variants).

The term "constraining" as used herein, preferably, means that the L2 polypeptide, or the fragment thereof (or the respective variants) that is comprised by the scaffold protein is present in a conformation that mimics its natural conformation. Preferably, said L2 polypeptide, or the fragment thereof (or the respective variant) is kept by the scaffold polypeptide in a fixed conformation, when constrained.

Any scaffold polypeptide being capable of constraining the structure of said L2 polypeptide, or of the fragment of said L2 polypeptide, preferably, can be used for the production of the immunogenic polypeptide according to the invention.

Preferably, the scaffold polypeptide is selected from the group consisting of thioredoxin, capsid polypeptides of adeno-associated viruses (e.g. AAV2, GenBank Accession No., NC_001401.2, GI:110645916; AAV8 GenBank Accession No., NC_006261.1, GI:51949963; AAV7 GenBank Accession No., NC_006260.1, GI:51949960), the tenth type III module of fibronectin (FN3, GenBank Accession No. 1TTF_A; GI:157834026, with insertion of the L2 polypeptide, fragment or variant thereof within the exposed PAVTVR (SEQ ID NO: 480) or GRGDSPASS (SEQ ID NO: 481) loop sites), lipocalins (particularly, the bilin-binding protein from *Pieris brassicae*, GenBank Accession No. CAA54063.1, GI:434995, with insertion of the L2 polypeptide, fragment or variant thereof within the PNSVEKY (SEQ ID NO: 482), IHGKE (SEQ ID NO: 483), TYGGVTK (SEQ ID NO: 484) and/or YDEDKKGH loop sites), a catalytically inactive version of *Staphylococcus* nuclease (e.g., GenBank Accession No. 2SNS_A, 2SNS_A GI:157836360, with peptide insertion within the YKGQP (SEQ ID NO: 485) loop site); an alpha-amylase inhibitor, preferably tendamistat (GenBank Accession No. CAA00655.1, GI:413044, with peptide insertion within the EDD and/or IGSHG loop sites); or stefin A (GenBank Accession No. P01040.1, GI:118177, with insertion of the L2 polypeptide, fragment or variant thereof within the KSL loop site).

In one preferred embodiment of the present invention, however, the scaffold protein is a thioredoxin polypeptide or a variant thereof.

Thioredoxin polypeptides are the major cellular disulfide redox components and serve as electron donors for enzymes such as ribonucleotide reductases, thioredoxin peroxidases and methionine sulfoxide reductases. Thioredoxins have an alpha/beta structure with two disulfide bondable cysteine residues. Thioredoxins are ubiquitous polypeptides and were shown to be present in most organisms (for a review see Arnér and Holmgren, Physiological functions of thioredoxin and thioredoxin reductase, European Journal of Biochemistry, Volume 267 Issue 20, Pages 6102-6109). The thioredoxin polypeptide in the context of the present invention may be derived from any organism. Preferably, the thioredoxin polypeptide comprises the so called thioredoxin display site CGPC (SEQ ID NO: 23). The thioredoxin display site, also known as thioredoxin motif or as dithio/disulfide active site, is a highly conserved motif amongst thioredoxin polypeptides.

Preferably, said thioredoxin polypeptide is selected from the group consisting of prokaryotic and eukaryotic thioredoxin polypeptides, or any other thioredoxin or thioredoxin-like protein, or proteins harbouring a thioredoxin (TRX) Pfam domain, bearing the conserved CGPC (SEQ ID NO: 23), or a CGXC, or a CXXC sequence motif (e.g., gi|40253454; gi|77456671; gi|31543902). More preferably, said thioredoxin polypeptide is selected from the group consisting of bacterial, animal and plant thioredoxin polypeptides Even more preferably, the thioredoxin polypeptide is a *Escherichia coli* thioredoxin as shown in SEQ ID NO: 24 (which shows 100% identity with the thioredoxin polypeptide of *Salmonella typhi*), or the homologous thioredoxin polypeptides from *Salmonella enterica* (SEQ ID NO: 25), mouse (SEQ ID NO: 26), rabbit (SEQ ID NO: 27), human (SEQ ID NO: 28), or any other thioredoxin or thioredoxin-like protein as shown in SEQ ID NO: 17. Also included are oligomers of said thioredoxin polypeptides, i.e. fusion polypeptides comprising at least two copies of thioredoxin polypeptides, e.g. dimers or trimers, wherein the C-terminus of one copy of a thioredoxin polypeptide is linked to the N-terminus of the following copy of a thioredoxin polypeptide. Preferably, at least one of the thioredoxin polypeptides comprises at least one L2 peptide inserted within the display site. More preferably, in said oligomers the thioredoxin polypeptides are separated by linker peptides, see e.g. SEQ ID NO:497 and SEQ ID NO: 498.

Preferably, the L2 polypeptide, or the fragment of said L2 polypeptide (or multimer or fragment thereof) is positioned within the so called "display site" of thioredoxin. Thus, the said L2 polypeptide or fragment thereof, preferably is positioned between the C and the G, or between the G and the P, or between the P and the C residues of the display site sequence CGPC (SEQ ID NO: 23) of the thioredoxin polypeptide. Also contemplated by the present invention is positioning the L2 polypeptide or fragment thereof adjacent to the display site, preferably, between any pair of amino acid residues located up to 20, up to 10, or up to 5 amino acid residues upstream or downstream from the display site.

The term "thioredoxin polypeptide" also includes variants of the thioredoxin polypeptide. The explanations of the term "variant" made elsewhere applies mutatis mutandis.

In a preferred embodiment the thioredoxin polypeptide is selected from the group consisting of a) a polypeptide having a sequence as shown in SEQ ID No: 24, SEQ ID No: 25, SEQ ID No: 26, SEQ ID No: 27, or SEQ ID No: 28 (or any other thioredoxin polypeptide as recited herein); and b) a variant polypeptide having a sequence at least 70% identical to the sequence shown in SEQ ID No: 24, SEQ ID No: 25, SEQ ID No: 26, SEQ ID No: 27, or SEQ ID No: 28 (or any other thioredoxin polypeptide as recited herein), wherein said polypeptide constrains the structure of the L2 polypeptide, or which constrains the structure of a fragment of said L2 polypeptide (or of a variant thereof).

As set forth above the thioredoxin polypeptide in the context of the present invention, preferably, shall comprise the thioredoxin display site.

In another preferred embodiment the thioredoxin polypeptide is derived from a thermophile bacterium. The use of a thioredoxin polypeptide from a thermophile bacterium allows for storage of the immunogenic polypeptides, e.g., at room temperature (instead of storing said polypeptide, e.g., at 4° C. or at even lower temperatures). Storing the immunogenic polypeptide, e.g., at 20° C. is, particularly, advantageous if said polypeptide is used as a vaccine since it allows the distribution of the polypeptide even in regions where cooling systems are not available.

Thermophile bacteria are known to grow at elevated temperatures (>50° C.), particularly in and/or around geothermal vents in marine or aquatic environments. A variety of termophile bacteria is known in the art. Preferred thermophile bacteria in the context of the present invention are Archaebacteria, particularly Methanosaeta thermophila, Archaeoglobus fulgidus, Metallosphaera sedula, Sulfolobus solfataricus, Sulfolobus tokodaii, Sulfolobus acidocaldarius, Metallosphaera sedula, Thermofilum pendens, Picrophilus torridus, Caldivirga maquilingensis. The amino acid sequence of thioredoxin polypeptides of a variety of thermophile bacteria is well known in the art. Preferred thiorexodin polypeptides derived from thermophile bacteria have an amino acid sequence as shown in GenBank-Accession Numbers Methanosaeta thermophila (gi|116754023, YP_843141; gi|116754438, YP_843556); Archaeoglobus fulgidus (gi|11498883, NP_070112; gi|11499727, NP_070969); Metallosphaera sedula (gi|146304377, YP_001191693; gi|146303559, YP_001190875); Sulfolobus solfataricus (gi|15897303, NP_341908; gi|15899007, NP_343612); Sulfolobus tokodaii (gi|15922449, NP_378118; gi|15921676, NP_377345); Sulfolobus acidocaldarius (gi|70605894, YP_254764.1; gi|70607552, YP_256422.1; gi|70607229, YP_256099); Thermofilum pendens (gi|119720035, YP_920530); Picrophilus torridus (gi|48477193, YP_022899); Caldivirga maquilingensis (gi|159040636, YP_001539888). Also included are thioredoxin polypeptides from Pyrococcus furiosus (SEQ ID NO: 493), Thermococcus kodakarensis (SEQ ID NO: 494), Thermococcus onnurineus (SEQ ID NO: 495), and Thermococcus sibiricus (SEQ ID NO: 496).

In a preferred embodiment the immunogenic polypeptide further comprises a polypeptide that further stimulates (enhances) immunogenicity of said immunogenic polypeptides. Such polypeptides stimulating immunogenicity are well known in the art. Preferred stimulating polypeptides are C4 bp (Complement component 4 binding protein) and MDC/CCL22 (Macrophage-Derived Chemokine_CC motif_ligand 22. It is to be understood that the immunogenic polypeptide and the stimulating polypeptide are fused in frame. Preferably, the stimulating polypeptide is fused to the N- or C-terminus of to the immunogenic polypeptide Preferably, the immunogenic polypeptide according to the invention is a polypeptide having an amino acid sequence as shown in SEQ ID NO: 29, or SEQ ID NO: 30.

The immunogenic polypeptide as shown in SEQ ID NO:29 comprises a multimer of 3 of the L2 fragment having a sequence as shown in SEQ ID NO:2, said fragments being connected by a linker peptide having a sequence as shown in SEQ ID NO:16.

The immunogenic polypeptide as shown in SEQ ID NO:30 comprises a multimer of 9 of the L2 fragment having a sequence as shown in SEQ ID NO:2, said fragments being connected by a linker peptide having a sequence as shown in SEQ ID NO:16.

The sequences as shown in SEQ ID NO: 29, and SEQ ID NO: 30 comprise two hexahistidine-tags for purification of said polypeptides. It is to be understood that these tag do not contribute to the immunogenicity of said polypeptide and, thus, can be omitted.

Advantageously, it was shown in the studies underlying the present invention that an immunogenic polypeptide comprising a scaffold polypeptide and a L2 polypeptide or a fragment thereof, wherein said scaffold protein constrains the structure of said polypeptide or of said fragment, confers strong immunogenicity and induces strong neutralizing responses against HPV16 as well as strong cross-neutralizing responses against other HPV genotypes such as HPV18, HPV31, HPV45 and HPV58. Particularly, it was shown that a thioredoxin polypeptide that comprises within its display site the L2 polypeptide or a fragment has a strong immunogenicity and allows for strong neutralizing as well as cross-neutralizing responses (see Examples). The immunogenicity and (cross-) neutralizing response was further enhanced when multimers of the L2 polypeptides or fragments thereof were inserted within the display site of the thioredoxin polypeptide (see Examples).

The immunogenic polypeptide according to the present invention is of advantage over prior art polypeptides, since the polypeptides as disclosed in prior art have a low immunogenicity or only induce strong but not cross-neutralizing responses. For example, L2 based peptides that are disclosed in the art are poorly immunogenic whereas L1 based peptides have a limited cross-protective capacity. Thus, the immunogenic polypeptide according to the present invention allows for the production of vaccines against a broad range of HPV genotypes, particularly high-risk HPV genotypes.

Moreover, the present invention relates to a polynucleotide encoding the immunogenic polypeptide according to the present invention.

The polynucleotides of the present invention may contain further nucleic acid sequences as well. Specifically, the polynucleotides of the present invention may encode fusion proteins wherein one partner of the fusion protein is a polypeptide being encoded by a nucleic acid sequence recited above. Such fusion proteins may comprise as additional part peptide sequences for monitoring expression (e.g., green, yellow, blue or red fluorescent proteins, alkaline phosphatase and the like) or so called "tags" which may serve as a detectable marker or as an auxiliary measure for purification purposes. Tags for the different purposes are well known in the art and comprise FLAG-tags, 6-histidine-tags, MYC-tags and the like.

The term "polynucleotide" as used herein refers to a linear or circular nucleic acid molecule. It encompasses DNA as well as RNA molecules. The polynucleotide of the present invention shall be provided, preferably, either as an isolated polynucleotide (i.e. isolated from its natural context) or in genetically modified form. The term encompasses single as well as double stranded polynucleotides. Moreover, comprised are also chemically modified polynucleotides including naturally occurring modified polynucleotides such as glycosylated or methylated polynucleotides or artificially modified derivatives such as biotinylated polynucleotides. The polynucleotide of the present invention is characterized in that it shall encode a polypeptide as referred to above. The polynucleotide, preferably, has a specific nucleotide sequence as mentioned above. Moreover, due to the degeneracy of the genetic code, polynucleotides are encompassed which encode a specific amino acid sequence as recited above.

Moreover, the term "polynucleotide" as used in accordance with the present invention further encompasses variants of the aforementioned specific polynucleotides. Said variants may represent orthologs, paralogs or other homologs of the polynucleotide of the present invention. The polynucleotide variants, preferably, comprise a nucleic acid sequence characterized in that the sequence can be derived from the aforementioned specific nucleic acid sequences by at least one nucleotide substitution, addition and/or deletion whereby the variant nucleic acid sequence shall still encode a polypeptide having the activity as specified above (constraining the L2 polypeptide or a fragment thereof). Variants also encompass polynucleotides comprising a nucleic acid sequence which is capable of hybridizing to the aforementioned specific nucleic acid sequences, preferably, under stringent hybridization conditions. These stringent conditions are known to the skilled worker and can be found in Current Protocols in Molecular Biology, John Wiley & Sons, N.Y. (1989), 6.3.1-6.3.6. A preferred example for stringent hybridization conditions are hybridization conditions in 6× sodium chloride/sodium citrate (=SSC) at approximately 45° C., followed by one or more wash steps in 0.2×SSC, 0.1% SDS at 50 to 65° C. The skilled worker knows that these hybridization conditions differ depending on the type of nucleic acid and, for example when organic solvents are present, with regard to the temperature and concentration of the buffer. For example, under "standard hybridization conditions" the temperature differs depending on the type of nucleic acid between 42° C. and 58° C. in aqueous buffer with a concentration of 0.1 to 5×SSC (pH 7.2). If an organic solvent is present in the above mentioned buffer, for example 50% formamide, the temperature under standard conditions is approximately 42° C. The hybridization conditions for DNA:DNA hybrids are preferably for example 0.1×SSC and 20° C. to 45° C., preferably between 30° C. and 45° C. The hybridization conditions for DNA:RNA hybrids are preferably, for example, 0.1×SSC and 30° C. to 55° C., preferably between 45° C. and 55° C. The above mentioned hybridization temperatures are determined for example for a nucleic acid with approximately 100 bp (=base pairs) in length and a G+C content of 50% in the absence of formamide. The skilled worker knows how to determine the hybridization conditions required by referring to textbooks such as the textbook mentioned above, or the following textbooks: Sambrook et al., "Molecular Cloning", Cold Spring Harbor Laboratory, 1989; Hames and Higgins (Ed.) 1985, "Nucleic Acids Hybridization: A Practical Approach", IRL Press at Oxford University Press, Oxford; Brown (Ed.) 1991, "Essential Molecular Biology: A Practical Approach", IRL Press at Oxford University Press, Oxford. Alternatively, polynucleotide variants are obtainable by PCR-based techniques such as mixed oligonucleotide primer-based amplification of DNA, i.e. using degenerated primers against conserved domains of the polypeptides of the present invention. Conserved domains of the polypeptide of the present invention may be identified by a sequence comparison of the nucleic acid sequence of the polynucleotide or the amino acid sequence of the polypeptide of the present invention with sequences of other members of the enzyme families referred to in accordance with this invention. Oligonucleotides suitable as PCR primers as well as suitable PCR conditions are described in the accompanying Examples. As a template, DNA or cDNA from bacteria, fungi, plants or animals may be used. Further, variants include polynucleotides comprising nucleic acid sequences which are at least 70%, at least 75%, at least 80%, at least 85%, at least 90%, at least 95%, at least 98% or at least 99% identical to the specific nucleic acid sequences. Moreover, also encompassed are polynucleotides which comprise nucleic acid sequences encoding amino acid sequences which are at least 70%, at least 75%, at least 80%, at least 85%, at least 90%, at least 95%, at least 98% or at least 99% identical to the specific amino acid sequences referred to herein. The percent identity values are, preferably, calculated over the entire amino acid or nucleotide sequence region. A series of programs based on a variety of algorithms is available to the skilled worker for comparing different sequences. In this context, the algorithms of Needleman and Wunsch or Smith and Waterman give particularly reliable results. To carry out the sequence alignments, the program PileUp (Higgins 1989, CABIOS, 5 1989: 151-153) or the programs Gap and BestFit (Needleman 1970, J. Mol. Biol. 48; 443-453 and Smith 198, Adv. Appl. Math. 2: 482-489), which are part of the GCG software packet from Genetics Computer Group, 575 Science Drive, Madison, Wis., USA 53711, version 1991, are to be used. The sequence identity values recited above in percent (%) are to be determined, preferably, using the program GAP over the entire sequence region with the following settings: Gap Weight: 50, Length Weight: 3, Average Match: 10.000 and Average Mismatch: 0.000, which, unless otherwise specified, shall always be used as standard settings for sequence alignments.

Moreover, the present invention relates to a vaccine comprising the immunogenic polypeptide according to the invention.

The term "vaccine" as used herein, preferably, relates to a composition which—when administered to an animal, preferably a human—elicits an immune response against various HPV genotypes. Thus, administering said vaccine would stimulate the immune system and establish or improve immunity to infection with various HPV genotypes. Preferably, the vaccine according to the present invention allows for establishing or improving immunity to infection with human papillomavirus genotypes 16, 18, 31, 45 and 58. Preferably, the vaccine according to the present invention also allows for establishing or improving immunity to infection with human papillomavirus genotypes 6, 52, 2, 27, 57 and/or 11. It is to be understood that the vaccine according to the present invention may comprise further components.

A preferred further component is an adjuvant. Adjuvants are compounds which may not elicit an immune response when administered to the host alone but which may further enhance the immune response of the host when administered together with the immunogenic polypeptides. It is known in the art that adjuvants may act as surfactants which promote concentration of immunogenic polypeptides over a large surface area, or may have immunostimulatory properties.

Preferred adjuvants in the context of the present invention are muramyl dipeptide, saponins such as QS21 and Quil A, monophosphoryl lipid A, mineral oil/surfactant mixtures (e.g., Montanide), aluminum hydroxide, aluminum phosphate, hydroxyapatite, complete and/or incomplete Freund's adjuvant, or cytokines such as interleukins, macrophage derived chemokines, complement binding proteins and tumor necrosis factor (either free or fused to the scaffold protein), and human use-approved live microbial carriers such as the live attenuated *Salmonella enterica* serovar Typhimurium strain.

Moreover the present invention relates to the use of the immunogenic polypeptide according the invention for the preparation of a vaccine for immunization of a subject against infection with HPV.

Preferably, said subject is an animal, more preferably, said subject is a vertebrate, even more preferably, said subject is a mammal and, most preferably, said subject is a human. Preferably, the immunization of said subject, establishes or improves immunity of said subject to various HPV genotypes as referred to elsewhere herein. It is to be understood that the immunogenic polypeptide according to the invention or vaccine according to the invention has to be administered to said subject for immunization. Said administration can be done by any method deemed appropriate such as oral or parentcral administration.

Moreover, the present invention relates to a method for producing an antibody against the immunogenic polypeptide according to the invention, comprising the following steps:

a) providing the immunogenic polypeptide according to the invention;

b) immunizing a host with said immunogenic polypeptide, and c) harvesting the antibody against said immunogenic polypeptide.

Preferably, the host will be sacrificed after the method has been carried out. It is to be understood that such a method is not deemed to be a method of treatment of the human or animal body.

The "host" in the context may be any host deemed appropriate. Preferably, the host is a non-human host. Preferred host for the production of monoclonal antibodies is a mouse or a rabbit. A host for the production of polyclonal antibodies is preferably selected from the group consisting of rabbits, mice, chickens, goats, guinea pigs, hamsters, horses, rats, and sheep.

Antibodies against the immunogenic polypeptide according to the present invention can be prepared by well known methods using said immunogenic polypeptide as an antigen. Preferably, the produced antibody is a polyclonal antibody. More preferably, said antibody is a monoclonal antibody.

Most preferably, said monoclonal antibody is produced by the hybridoma cell line which has been deposited with the German Collection of Microorganisms and Cell Cultures (DSMZ), Braunschweig, Germany on Nov. 27, 2008 under deposit number DSM ACC2983 according to the Budapest Treaty, or a fragment thereof (preferably, F(ab)$_2$, F(ab')2, Fab, F (ab'), Dab, Fv, sFv, scFv, or Fc fragments), or said monoclonal antibody produced by the hybridoma cell line which has been deposited with the German Collection of Microorganisms and Cell Cultures (DSMZ), Braunschweig, Germany on Nov. 27, 2008 under deposit number DSM ACC2984 according to the Budapest Treaty, or a fragment thereof (preferably, F(ab)2, F(ab')2, Fab, F (ab'), Dab, Fv, sFv, scFv, or Fc fragments). The monoclonal antibody produced by the hybridoma cell line which has been deposited with the German Collection of Microorganisms and Cell Cultures (DSMZ), Braunschweig, Germany on Nov. 27, 2008 under deposit number DSM ACC2983 is herein also referred to as K4L2(20-38)4.1B. The monoclonal antibody produced by the hybridoma cell line which has been deposited with the German Collection of Microorganisms and Cell Cultures (DSMZ), Braunschweig, Germany on Nov. 27, 2008 under deposit number DSM ACC2984 is herein also referred to as K18L2(20-38)XIII.5G.

It is also contemplated by the present invention that the antibody is a single chain antibody, a recombinant, human or humanized antibody or primatized, chimerized or a fragment of the antibody according to the present invention.

Also comprised by the aforementioned method of the present invention is the production of a synthetic antibody, an antibody fragment, such as F(ab)$_2$, F(ab')2, Fab, F (ab'), Dab, Fv, sFv, scFv, or Fc fragments etc., or a chemically modified derivative of any of these. The antibody may belong to any immunoglobulin class, including IgM, IgG, IgD, IgE, IgA, or subclasses of IgG (such as IgG1, IgG2, IgG2, IgG2a, IgG2b, IgG3 or IgGM).

How to produce and harvest the aforementioned antibodies and fragments is well known in the art. Antibodies or fragments thereof can be obtained by using methods which are described, e.g., in Harlow and Lane "Antibodies, A Laboratory Manual", CSH Press, Cold Spring Harbor, 1988. Monoclonal antibodies can be prepared by the techniques originally described in Köhler and Milstein, Nature 256 (1975), 495, and Galfré, Meth. Enzymol. 73 (1981), 3, which comprise the fusion of mouse myeloma cells to spleen cells derived from immunized mammals. It is also contemplated that monoclonal antibodies are produced by fusing myeloma cells with the B-cells from rabbits that have been immunized with the desired antigen.

It is to be understood that the antibody produced by the aforementioned method shall specifically bind the immunogenic polypeptide according to the invention. Specific binding can be tested by various well known techniques. Preferably, the antibody produced by the aforementioned method shall specifically bind the L2 polypeptide or fragment thereof. More preferably, said antibody shall specifically bind the L2 polypeptide or fragment thereof, when comprised by the immunogenic polypeptide according to the present invention (linked to the scaffold polypeptide), and thus when being present in a constrained structure. Thus, the antibody according to the present invention shall not specifically bind the parts of the immunogenic polypeptide that are derived from the scaffold polypeptide.

The aforementioned method of the present invention, preferably, allows for the production of an antibody against human papillomavirus. Preferably, said antibody binds the L2 polypeptide or fragments thereof of various HPV genotypes. Preferably, said antibody binds the L2 polypeptide or fragment thereof of HPV genotypes 16, 18, 31, 45 and 58. Preferably, the said antibody also binds the L2 polypeptide or fragments thereof of HPV genotypes 52, 2, 27, 57 and/or 11.

The present invention relates also to an antibody obtainable/produced by the aforementioned method of the present invention.

Said antibody of the present invention, preferably is a polyclonal antibody and, more preferably, a monoclonal antibody.

Most preferably, the antibody according to the present invention is the monoclonal antibody K4L2(20-38)4.1B (see Examples) produced by the hybridoma cell line which has been deposited with the German Collection of Microorganisms and Cell Cultures (DSMZ), Braunschweig, Germany on Nov. 27, 2008 under deposit number DSM ACC2983 according to the Budapest Treaty, or a fragment thereof (preferably, F(ab)$_2$, F(ab')2, Fab, F (ab'), Dab, Fv, sFv, scFv, or Fc fragments), or the antibody according to the present invention is the monoclonal antibody K18L2(20-38)XIII.5G (see Examples), which has been deposited with the German Collection of Microorganisms and Cell Cultures (DSMZ), Braunschweig, Germany on Nov. 27, 2008 under deposit number DSM ACC2984 according to the Budapest Treaty, or a fragment thereof (preferably, F(ab)$_2$, F(ab')2, Fab, F (ab'), Dab, Fv, sFv, scFv, or Fc fragments).

The antibodies according to the present invention can be used, for example, for the immunoprecipitation and immunolocalization of the immunogenic polypeptides of the present invention as well as for monitoring the presence of said variant polypeptides; for example, for the diagnosis of HPV infection, particularly for diagnosing infection with HPV genotypes 16, 18, 31, 45 and/or 58. Preferably, said diagnosis is done by determining the amount (or presence) of the L2 polypeptide in a biological sample from a subject suspected to be infected with HPV genotype 16, 18, 31, 45 and/or 58 (e.g. in a Pap smear). The presence of the L2 polypeptide (or increased amounts of the L2 polypeptide compared with a reference amount, e.g. the amount of said polypeptide in a sample from a subject not infected with HPV) indicates infection with HPV, whereas the absence of the L2 polypeptide (or decreased amounts of the L2 polypeptide compared with a reference amount, e.g. the amount of said polypeptide in a sample of a subject not infected with HPV) indicates that said subject is not infected with HPV.

Moreover, the antibodies according to the present invention can be used for the preparation of a pharmaceutical composition for passive immunization against various HPV genotypes, particularly against HPV genotypes 16, 18, 31, 45 and/or 58. For passive immunization, the antibody according to the present invention is administered to a subject in order to protect said subject against infection with various HPV genotypes and/or to treat an existing HPV infection, particularly infection with HPV genotypes 16, 18, 31, 45 or 58.

Also, the antibody of the present invention can be used for the production of anti-idiotypic antibodies. An "anti-idiotypic antibody" in the context of the present invention is an antibody that specifically binds to the idiotypic region of the antibody according to the present invention, or a fragment thereof. The idiotypic region of the antibody according to the present invention (or a fragment thereof) is, preferably, the unique part of its variable region that specifically binds to the immunogenic polypeptide according to the present invention. Preferably, the anti-idiotypic antibody is a monoclonal antibody.

Anti-idiotypic antibodies as well as methods for their production are well known in the art, see, e.g., US20080127359, or U.S. Pat. No. 5,792,455; Dalgleish: An anti-idiotype vaccine for AIDS based on the HIV receptor. Ann Ist Super Sanita. 1991; 27(1):27-31, or Attanasio, Int Rev Immunol. 1990; 7(1):109-19.

Preferably, said anti-idiotypic antibodies are produced by a) providing an antibody according to the present invention (preferably, a monoclonal antibody according to the invention, more preferably, K4L2(20-38)4.1B, or a fragment thereof, or K18L2(20-38)XIII.5G, or a fragment thereof), b) immunizing a host with said antibody, and c) harvesting the resulting anti-idiotypic antibody.

Accordingly, the present invention also relates to a method for producing anti-idiotypic antibodies by carrying out the aforementioned steps a) and b).

Moreover, the present invention relates to the use of the hybridoma cell line which has been deposited with the German Collection of Microorganisms and Cell Cultures (DSMZ), Braunschweig, Germany on Nov. 27, 2008 under deposit number DSM ACC2983, and to the use of the hybridoma cell line which has been deposited with the German Collection of Microorganisms and Cell Cultures (DSMZ), Braunschweig, Germany on Nov. 27, 2008 under deposit number DSM ACC2984 for the production of a monoclonal antibody that specifically binds the L2 peptide (as described herein).

Finally, the present invention also relates to the hybridoma cell line which has been deposited with the German Collection of Microorganisms and Cell Cultures (DSMZ), Braunschweig, Germany on Nov. 27, 2008 under deposit number DSM ACC2983 or under deposit number DSM ACC2984 according to the Budapest Treaty.

All references cited in this specification are herewith incorporated by reference with respect to their entire disclosure content and the disclosure content specifically mentioned in this specification.

The Figures show:

FIG. 1. Trx-L2 Peptides.

(A) Schematic representation of the HPV16 L2 peptides examined in this study. L2 aa 1-120 1x (1x SEQ ID NO:1+1x SEQ ID NO:24, thus the L2 polypeptide having a sequence as shown in SEQ ID NO1 inserted within the display site of the thioredoxin polypeptide having a sequence as shown in SEQ ID NO:24), 2x (SEQ ID NO:1 (2x)+SEQ ID NO:16(1x)+SEQ ID NO:24, thus two fragments of the L2 polypeptide, said fragments having a sequence as shown in SEQ ID NO:2, said fragments linked via one linker peptide having a sequence as shown in SEQ ID NO:16, inserted within the display site of the thioredoxin polypeptide having a sequence as shown in SEQ ID NO:24), 3x (SEQ ID NO:1 (3x)+SEQ ID NO:16(2x)+SEQ ID NO:24); L2 aa 20-38 1x (SEQ IS NO:2+SEQ ID NO:24), 3x (SEQ ID NO:29), 9x (SEQ ID NO:30), 15x (SEQ IS NO:2 (15x)+SEQ ID NO:16 (14x)+SEQ ID NO:24); L2 aa 28-42 1x, 4x, 8x; L2 aa 56-75 1x, 4×; L2 aa 64-81 1x, 4x, 8x; L2 aa 95-115 1x, 4x, 8x. (B) Representative example of the expression analysis of pTrx-L2(20-38)n constructs with varying L2 peptide insert multiplicity (n). SDS-PAGE of total bacterial lysates from different clones ordered according to the multiplicity of their L2(20-38) peptide inserts; the peptide insert multiplicity (n) of the various fusion proteins and the migration positions of molecular mass markers are indicated on the right hand side and on the left hand side, respectively. (C) Representative examples of purified Trx-L2(20-38)n fusion proteins used for mice immunization (1) L2 aa 20-38 1x (SEQ IS NO:2+SEQ ID NO:24), 3x (SEQ ID NO:29), 9x (SEQ ID NO:30), 15x (SEQ IS NO:2 (15x)+SEQ ID NO:16 (14x)+SEQ ID NO:24). (D) Comparison of the immune responses elicited by the HPV16 L2(20-38) peptide chemically conjugated to KLH and by the same peptide grafted to Trx, both administered (100 μg/dose) with the same CFA/IFA immunization protocol described in 'Materials and methods'. ELISA data, obtained using GST-L2 as target antigen and expressed as A405 values, are presented as dot plots. The L2 binding activity of individual sera as well as the mean binding activity of each group (horizontal bars) are shown; KLH and Trx indicate the unconjugated carrier proteins utilized as negative controls. Please note that the numbers correspond to the amino acid positions of the L2 polypeptide as shown in SEQ ID NO:1. E.g., "L2(20-38)" stands for a fragment of the L2 polypeptide as shown in SEQ ID NO:1 comprising amino acids 20 to 28 of said polypeptide.

FIG. 2. Antibody Titers of Mice Vaccinated with the Trx-L2 Peptide Fusions.

GST-L2 ELISA was used to determine the antibody titers of sera from mice immunized three times with the indicated Trx-L2(peptide)n fusions, for group L2 aa 20-38 1x (SEQ IS NO:2+SEQ ID NO:24), 3x (SEQ ID NO:29), 9x (SEQ ID NO:30), 15x (SEQ IS NO:2 (15x)+SEQ ID NO:16 (14x)+SEQ ID NO:24) and group Trx-L2 L2 aa 1-120 1x (1x SEQ ID NO:1+1x SEQ ID NO:24), 2x (SEQ ID NO:1 (2x)+SEQ ID NO:16(1x)+SEQ ID NO:24), 3x (SEQ ID NO:1 (3x)+SEQ ID NO:16(2x)+SEQ ID NO:24); L2 aa 28-42 1x, 4x, 8x; L2 aa 56-75 1x, 4x; L2 aa 64-81 1x, 4x, 8x; L2 aa 95-115 1x, 4x, 8x (100 μg each, corresponding to 1.7-4.3 nmol of protein, depending on the size of the peptide insert; n values are shown on the x-axis) administered with the CFA/IFA immunization protocol described in 'Materials and methods'. Sera from mice immunized with the Trx protein scaffold only (not shown) were used as negative controls and were assayed in parallel in each set of ELISAs. Binding titers are given as the reciprocal of the maximum antisera dilutions that yielded A405 values higher than the mean absorbance plus four standard deviations of sera from mice immunized with the Trx scaffold only. Data are presented as log 10 dot-plots of the titers; horizontal bars represent the geometric mean of the titers for each of the indicated subgroups of Trx-L2 antisera. The P values in each panel indicate the statistical significance of the differences between the immune responses induced by monopeptide and multipeptide Trx-L2 fusions in each group.

FIG. 3. Neutralization of HPV 16 Infection by Trx-L2 Peptide Antisera.

Serial dilutions of antisera raised against the monopeptide and multipeptide Trx-L2 fusions shown in FIG. 2 were analyzed for their capacity to block infection of 293TT cells by HPV16 pseudovirions using secreted alkaline phosphatase (SEAP) activity as readout. Neutralization efficiency was determined relative to that of mock-treated (0% neutralization) and HPV16 L1-specific mAb-treated (100% neutralization) controls, which were run in parallel in each assay (see 'Materials and methods' for details). Data for the monopeptide and the aggregated multipeptide forms of each Trx-L2 immunogen L2 aa 20-38 1x (SEQ IS NO:2+SEQ ID NO:24), 3x (SEQ ID NO:29), 9x (SEQ ID NO:30), 15x (SEQ IS NO:2 (15x)+SEQ ID NO:16 (14x)+SEQ ID NO:24); L2 aa 28-421×, 4×, 8x; L2 aa 56-751×, 4×; L2 aa 64-81 1x, 4x, 8x and L2 aa 95-1151×, 4×, 8x are expressed as the reciprocal of the maximum dilution causing ≥70% neutralization. The geometric means of the titers and the 95% confidence intervals for each group of anti-Trx-L2 peptide antisera plus the anti-Trx-L2(1-120) 1x (1x SEQ ID NO:1+1x SEQ ID NO:24), 2x (SEQ ID NO:1 (2x)+SEQ ID NO:16(1x)+SEQ ID NO:24), 3x (SEQ ID NO:1 (3x)+SEQ ID NO:16(2x)+SEQ ID NO:24) reference are represented on a log scale.

Figure 4:
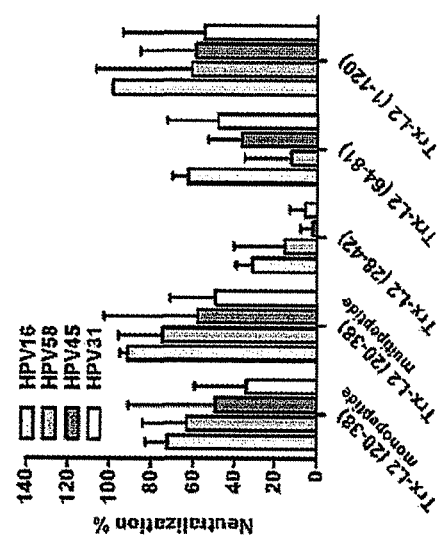

FIG. 4. Cross-Neutralization of HPV 31, 45, and 58 Pseudovirions.

The crossneutralization activities of the indicated subset of Trx-L2 peptide antisera were assayed at a fixed 1:200 dilution against three heterologous pseudovirions (HPV 31, 45 and 58) plus the cognate HPV16 type. Mock-treated 293TT cells and cells treated with type-specific neutralizing antibodies served as negative and positive controls, respectively (see FIG. 3) legend and 'Materials and methods' for details). Cumulative monopeptide and multipeptide data are presented for each immunogen except Trx-L2 aa 20-38 1x (SEQ IS NO:2+SEQ ID NO:24), 3x (SEQ ID NO:29), 9x (SEQ ID NO:30), 15x (SEQ IS NO:2 (15x)+SEQ ID NO:16 (14x)+ SEQ ID NO:24), the only one for which a trend toward a peptide multiplicity-dependent increase in cross-neutralization activity was observed; they are represented as the mean plus SD of the neutralization values for the various Trx-L2 peptide antisera relative to those obtained with HPV type-specific antibodies.

Figure 5:
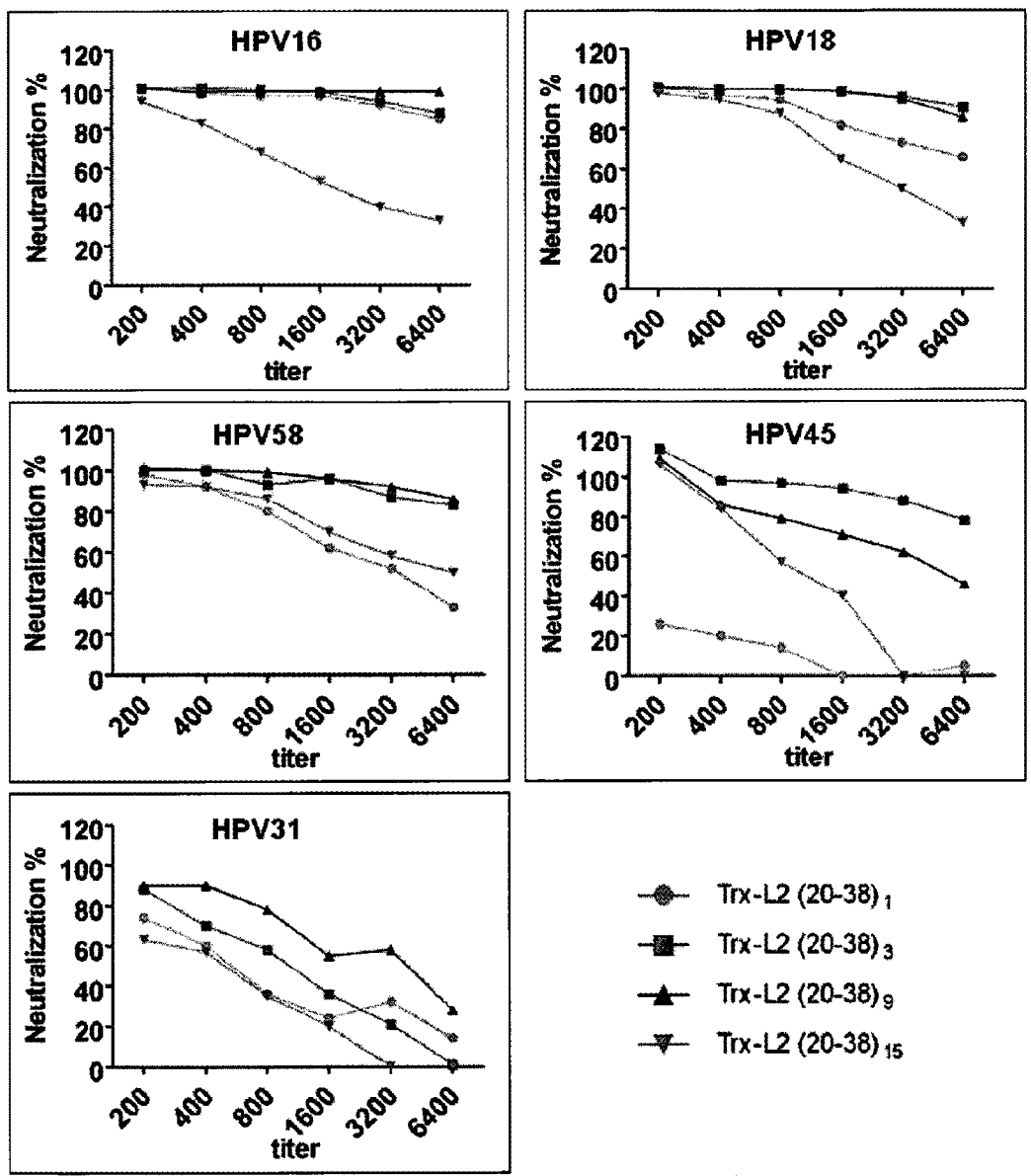

FIG. 5. Neutralization of Homologous and Heterologous Pseudovirions by Trx-L2(20-38)n Antisera.

Figure 3:
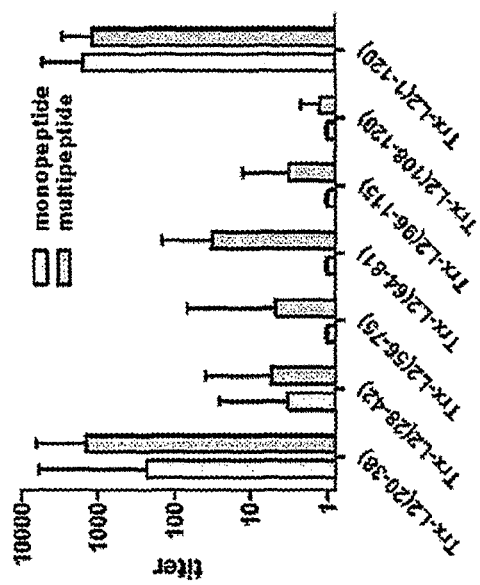

The strongest HPV 16 neutralizing antisera from each group of Trx-L2(20-38)n antigens (n=1, 3, 9, 15) 1x (SEQ IS NO:2+SEQ ID NO:24), 3x (SEQ ID NO:29), 9x (SEQ ID NO:30), 15x (SEQ IS NO:2 (15x)+SEQ ID NO:16 (14x)+ SEQ ID NO:24) were titrated against homologous (HPV16) and heterologous (HPV18, 31, 45, 58) pseudovirions (see 'Materials and methods' and FIG. 3 legend for details).

FIG. 6. Sequence Comparison of the L2(20-38) Region of the Examined HPV Types. Multiple sequence alignment was performed with CLUSTAL W [30]; amino acids identical to those of the cognate HPV16 type are indicated with dots. Conservative and non-conservative substitutions are shown in standard and in bold characters, respectively; non-conservative substitutions occurring in only one of the five examined HPV types are boxed.

FIG. 7. Neutralizing Titers of Supernatants of Monoclonal Antibodies Against the aa 20-31 from HPV16 L2 Protein IgG concentration in supernatants was adjusted to 0.6 µg/ml, titer was defined as the last dilution that can protect 70% of pseudovirions infection. There are not big differences in the neutralization capacity of antibodies #4 (K4L2(20-38) 4.1B) and #18 (K18L2(20-38)XIII.5G) except for the neutralization of HPV31. Antibody #18 can neutralize the infection although with low titer, but, antibody #4 is unable to neutralize the infection even at low dilution factor. Antibody #8 and #1 can neutralize only HPV16. Antibody #1 can neutralize HPV 16 with high titer.

Figure 8:
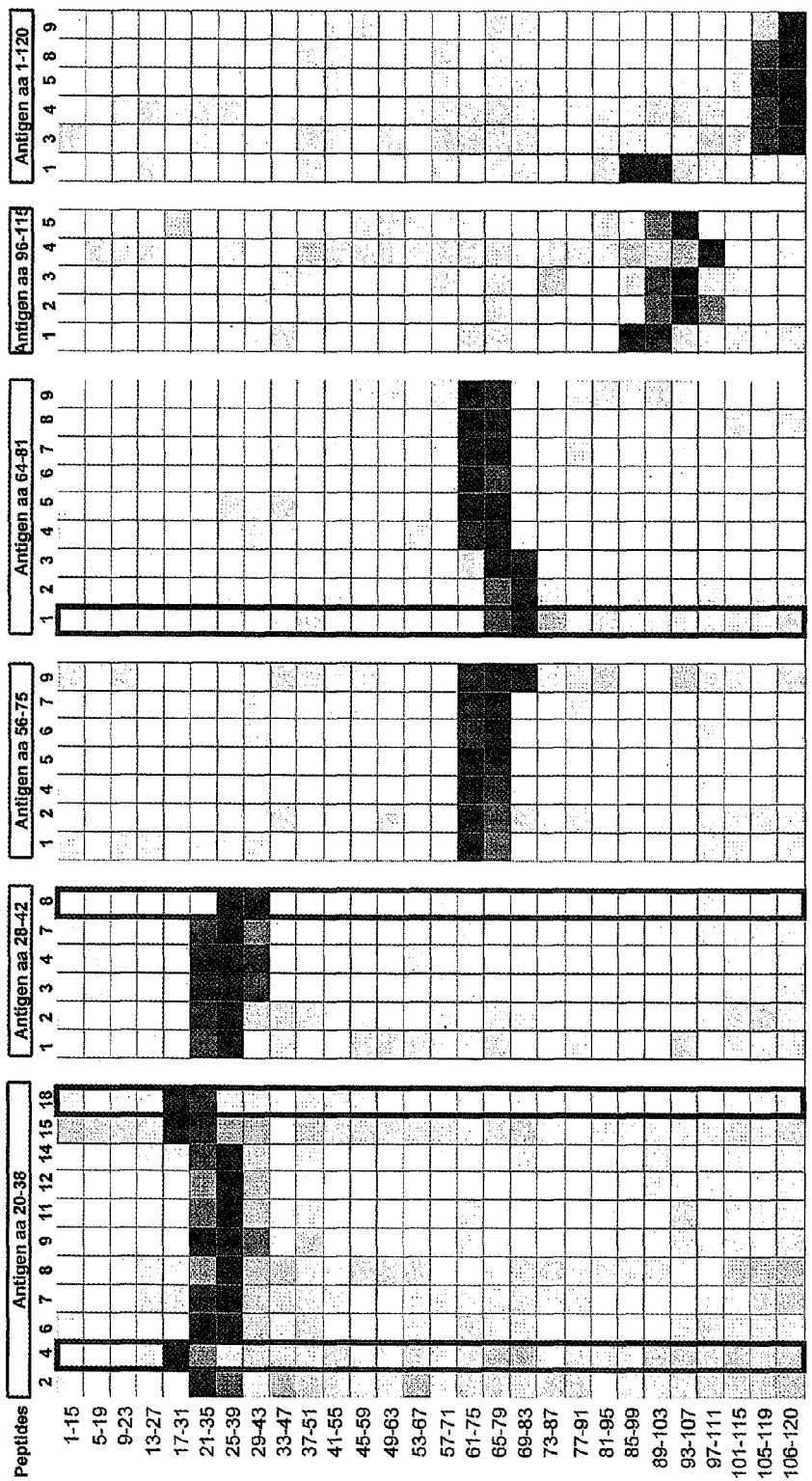

FIG. 8. Identification of Epitopes Recognized by Neutralizing (Boxed) and Non-Neutralizing Antibodies The different monoclonal antibodies raised against different regions of the HPV 16 N-terminus were tested for their reactivity with a set of overlapping peptides (amino acids 1-15, 5-19, 106-120) in ELISA. All four neutralizing antibodies show a distinct pattern in binding the peptides, different to the pattern of the non-neutralizing antibodies. The two cross-neutralizing antibodies (K4L2(20-38)4.1B) and #18 (K18L2 (20-38)XIII.5G) are directed against region 20-38. Antibody #15, which shows a similar binding pattern compared to #18, has an about 30 fold lower affinity to its target which explains its failure to neutralize HPV pseudovirions.

Figure 9:
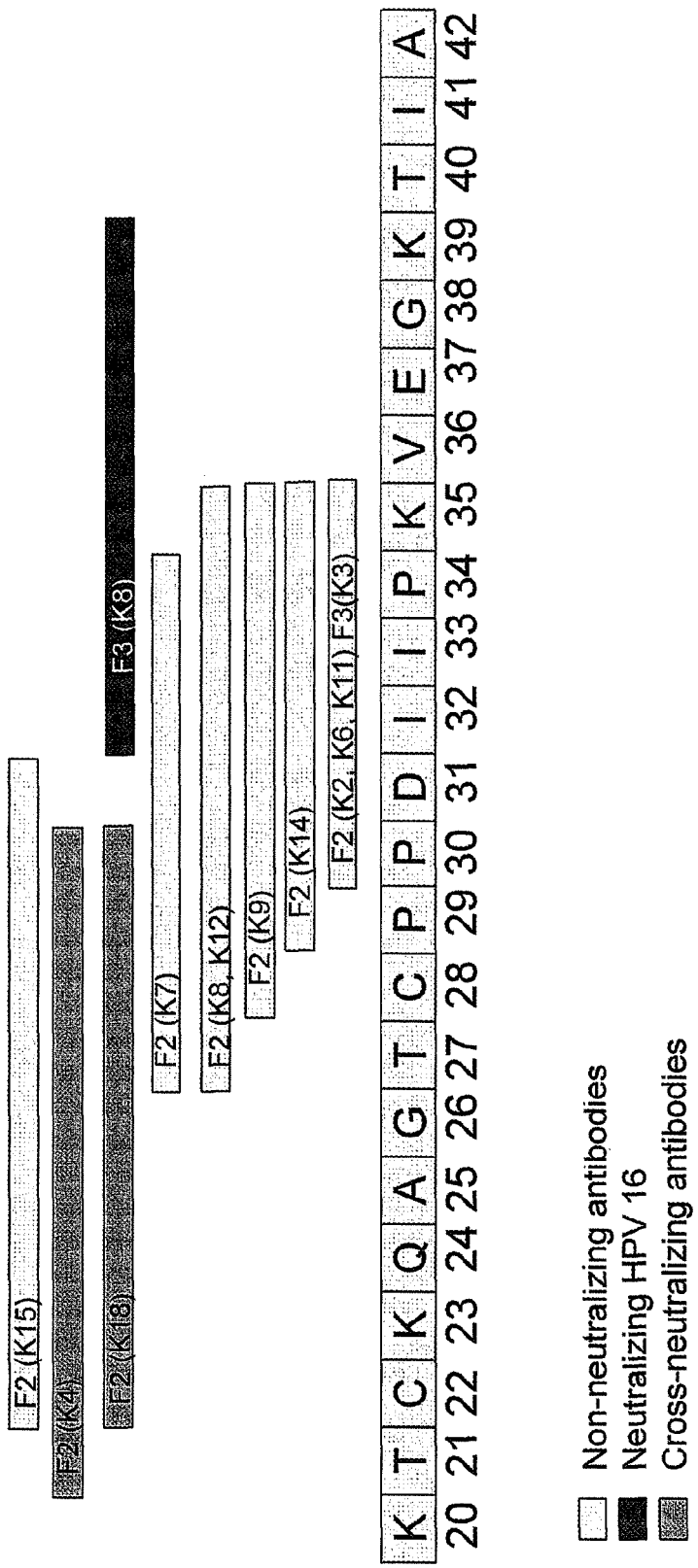

FIG. 9. Epitopes for Non-Neutralizing, Neutralizing and Cross-Neutralizing Antibodies (K4L2(20-38)4.1B and K18L2(20-38)XIII.5G) within Region 20-42 of HPV 16 L2.

Scheme with the recognition patron of all mAbs isolated against the region 20-42. Cross-neutralizing antibodies Mab K4L2(20-38)4.1B recognize the sequence aa 21-30 SEQ ID NO:4 and K18L2(20-38)XIII.5G recognize the sequence aa 22-30 SEQ ID NO:5. Neutralizing antibody anti HPV16 K8L2(28-42)12.4B recognize the sequence aa 32-39 SEQ ID NO:31.

Figure 10A:
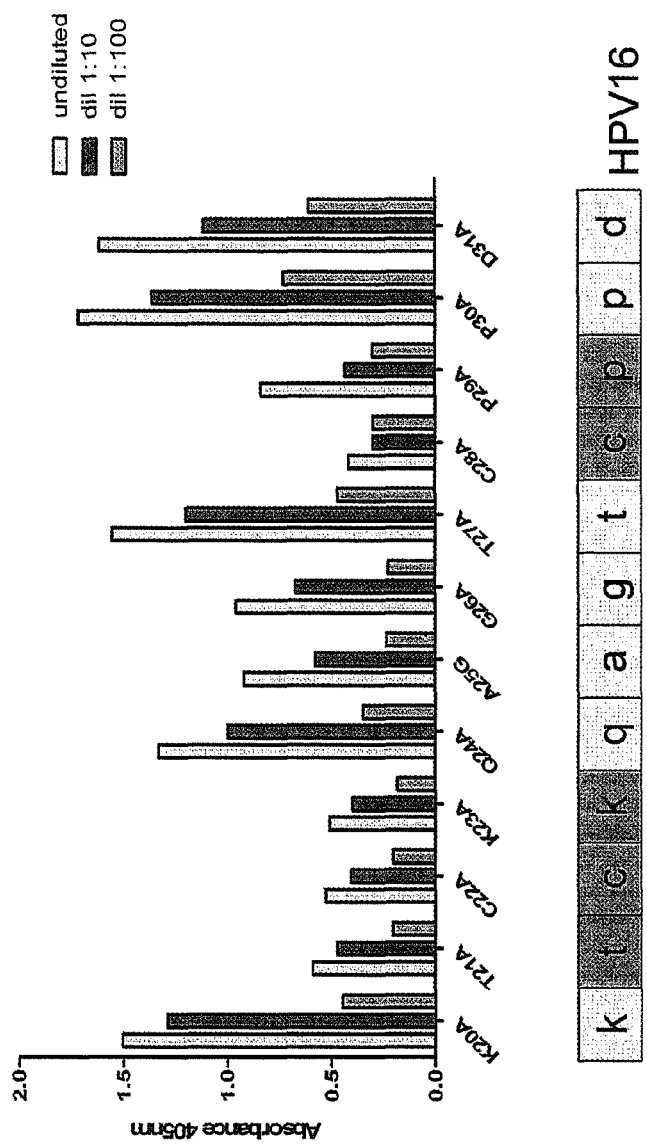
Figure 10B:
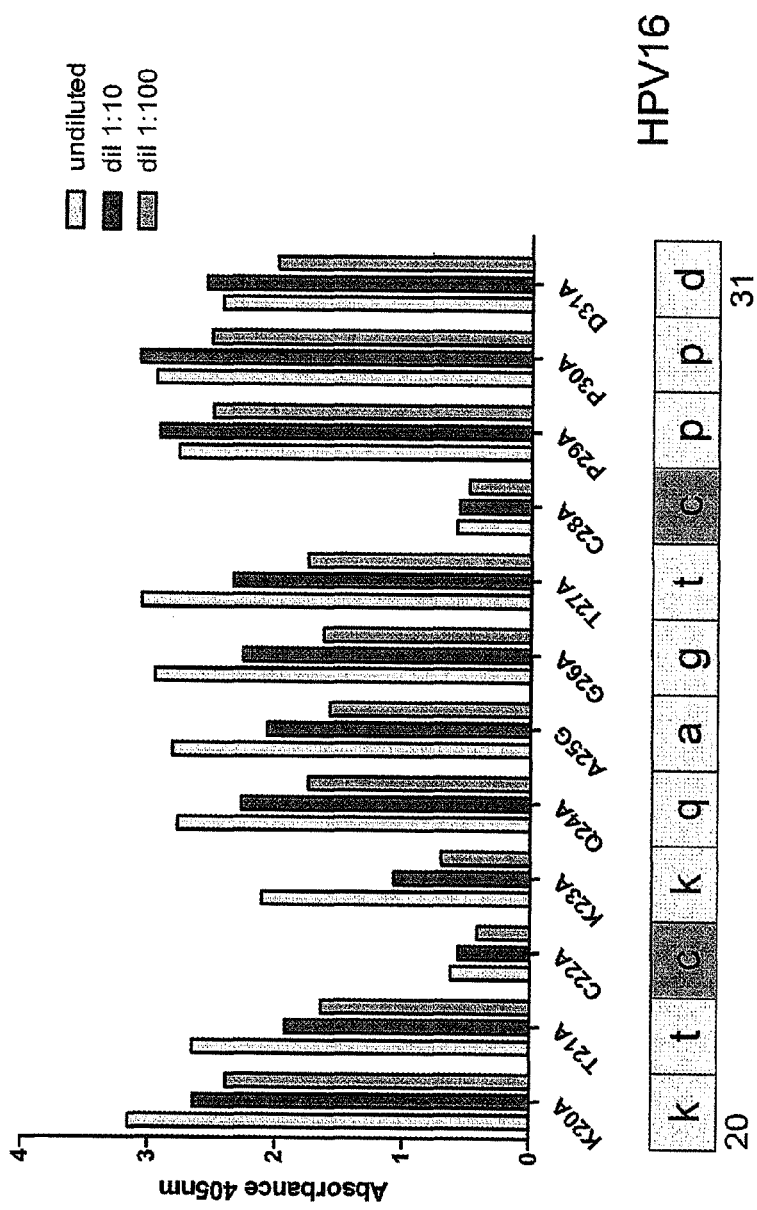

FIG. 10. Epitope Mapping for the Two Neutralizing Antibodies (K4L2(20-38)4.1B) and #18 (K18L2(20-38) XIII.5G).

To determine the amino acids required for binding of the two antibodies K4 (A9 and K18 (B) an peptide-alanine scan was performed. Antibody #4 the five amino acids xTCKxxxx-CPxx are essential for binding while for K8 only the two cysteine residues are crucial for binding, although the remainder residues might contribute to the binding.

Figure 11:
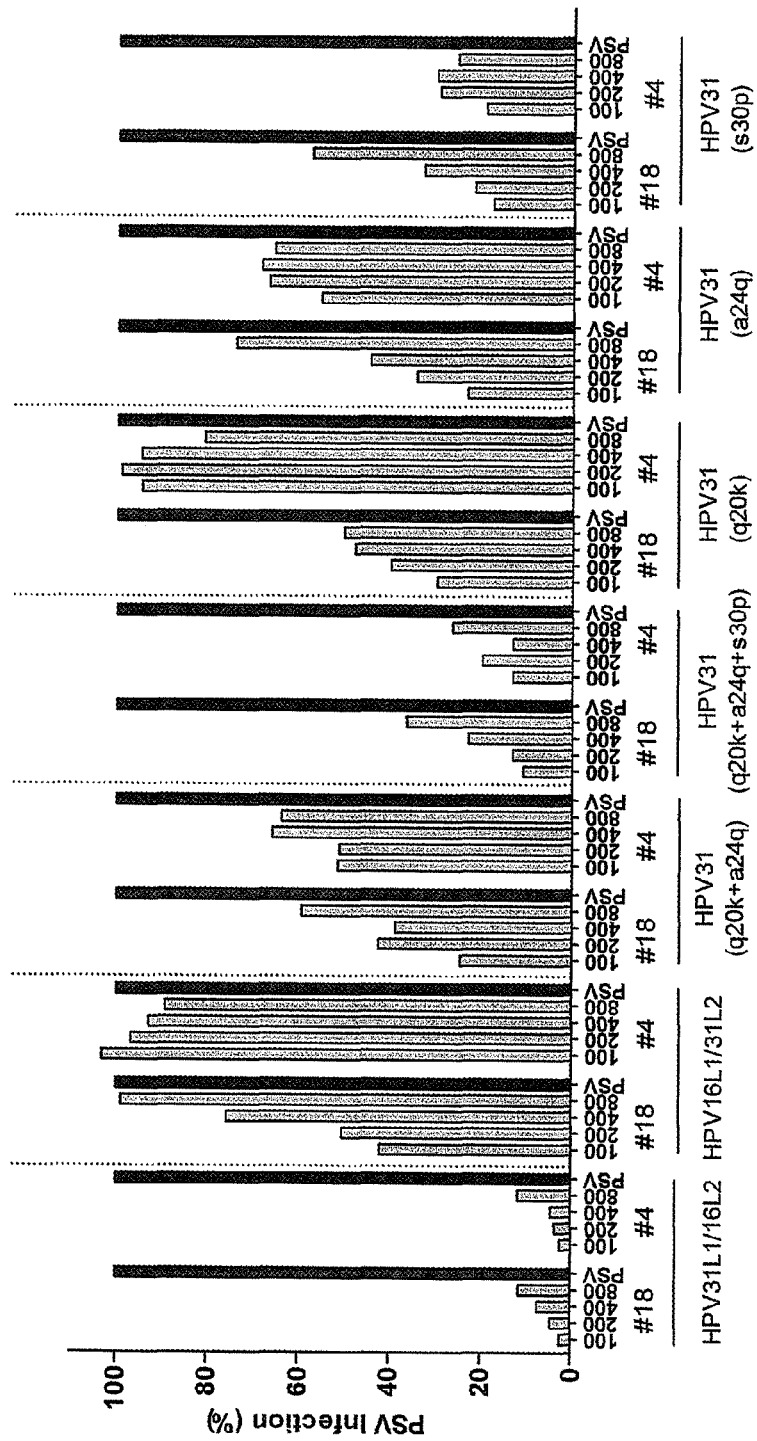

FIG. 11. Neutralization Assay of HPV 16 and HPV 31 Pseudovirions with Modified L2 Proteins.

To determine why antibodies #4 (K4L2(20-38)4.1B) and #18 (K18L2(20-38)XIII.5G) have different abilities to neutralize HPV 31 we tested hybrid particles composed of HPV 16 L1 HPV 31 L2 and vice versa. In addition, the corresponding epitope in HPV 31 recognized by K4 and K18 was modified. Results indicate that the ability of (K4L2(20-38)4.1B) and #18 (K18L2(20-38)XIII.5G) antibodies to neutralize depends on the epitope sequence as HPV 31 L1/16L2 pseudovirions can be neutralized by both antibodies. Altering serine at position 30 into proline restores the ability to neutralize HPV 31 pseudovirions indicating that this residue is important in binding the antibodies.

EXAMPLES

Example 1

Monopeptide (1x SEQ ID NO:2) and multipeptide ((SEQ ID NO:2 (3x)+SEQ ID NO:16(2x)) or 3x (SEQ ID NO:2 (3x)+SEQ ID NO:16(2x)) immunogenic peptides are inserted within the display site of the thioredoxin polypeptide having a sequence as shown in SEQ ID NO: 493 to SEQ ID NO: 496. Fusion proteins are produced in *E. coli* cells, purified from cell extracts and used for immunization.

TABLE 1

List of L2 peptide immunogens (and variants thereof)

| | |
|---|---|
| SEQ ID NO: 33 | RGCKQAGTCPPPDVINKVEQ |
| SEQ ID NO: 34 | RGCKASNTCPPPDVINKVEQ |
| SEQ ID NO: 35 | RGCKAAGTCPPPDVINKVEQ |
| SEQ ID NO: 36 | QSCKAAGTCPPPDVLNKVEQ |
| SEQ ID NO: 37 | QSCKAAGTCPPPDVVNKVEQ |
| SEQ ID NO: 38 | QTCKQAGTCPPPDVVNKVEQ |
| SEQ ID NO: 39 | QTCKQAGTCPPPDVVNKVEQ |
| SEQ ID NO: 40 | RTCKQAGTCPPPDVINKVES |
| SEQ ID NO: 41 | RTCKQAGTCPPPDVINKVEQ |
| SEQ ID NO: 42 | KGCKASGTCPPPDVINKVEQ |
| SEQ ID NO: 43 | RTCKQSGTCPPPDVVPKVEG |
| SEQ ID NO: 44 | RTCKQAGTCPPPDVIPKVEG |
| SEQ ID NO: 45 | RTCKVTGTCPADVVPKVEG |
| SEQ ID NO: 46 | RTCKATGTRPADVIPKVEG |

TABLE 1-continued

List of L2 peptide immunogens (and variants thereof)

| | |
|---|---|
| SEQ ID NO: 47 | RTCKQSGTCPPDIIPRVEQ |
| SEQ ID NO: 48 | RTCKQAGTCPPDIIPRLEQ |
| SEQ ID NO: 49 | RTCKQAGTCPPDIIPRVEQ |
| SEQ ID NO: 50 | KTCKVAGTCPPDVIPKVEG |
| SEQ ID NO: 51 | KTCKAAGTCPPDVIPKVEG |
| SEQ ID NO: 52 | RTCKAAGTCPPDVIPKVEG |
| SEQ ID NO: 53 | RTCKASGTCPPDVIPKVEG |
| SEQ ID NO: 54 | STCKAAGTCPADVIPKVEG |
| SEQ ID NO: 55 | KTCKLSGTCPEDVINKVEQ |
| SEQ ID NO: 56 | KTCKQSGTCPPDIIPKVEG |
| SEQ ID NO: 57 | KTCKQAGTCPPDIVPKVEG |
| SEQ ID NO: 58 | QTCKASGTCPPDVIPKVEG |
| SEQ ID NO: 59 | KTCKQAGTCPPDVIPKVEG |
| SEQ ID NO: 60 | QTCKAAGTCPSDIIPKVEH |
| SEQ ID NO: 61 | QTCKASGTCPPDVIPKVEQ |
| SEQ ID NO: 62 | QTCKLTGTCPPDVIPKVEH |
| SEQ ID NO: 63 | QTCKAAGTCPSDVINKVEH |
| SEQ ID NO: 64 | KQCQLGADCPPDVRNKVEG |
| SEQ ID NO: 65 | AKCQLSGNCLPDVKNKVEA |
| SEQ ID NO: 66 | AKCQLSGDCLPDVKNKVEA |
| SEQ ID NO: 67 | RHCALSGTCPDDVKNKVEN |
| SEQ ID NO: 68 | KHCAGSGTCPEDVKNKVEQ |
| SEQ ID NO: 69 | KTCLQGGDCIPDVKNKFEN |
| SEQ ID NO: 70 | RSCLQGGDCIPDVQNKFEG |
| SEQ ID NO: 71 | QTCKATGTCPPDVIPKVEG |
| SEQ ID NO: 72 | KTCKQSGTCPPDVVPKVEG |
| SEQ ID NO: 73 | RTCKQSGTCPPDVINKVEG |
| SEQ ID NO: 74 | KTCKQAGTCPSDVINKVEG |
| SEQ ID NO: 75 | KTCKLSGTCPEDVVNKIEQ |
| SEQ ID NO: 76 | RTCKQSGTCPPDVVDKVEG |
| SEQ ID NO: 77 | STCKAAGTCPPDVVNKVEG |
| SEQ ID NO: 78 | PTCKIAGNCPADIQNKFEN |
| SEQ ID NO: 79 | PACKISNTCPPDIINKYEN |
| SEQ ID NO: 80 | RGCKQAGTCPPD |
| SEQ ID NO: 81 | RGCKASNTCPPD |
| SEQ ID NO: 82 | RGCKAAGTCPPD |
| SEQ ID NO: 83 | QSCKAAGTCPPD |
| SEQ ID NO: 84 | QTCKQAGTCPPD |
| SEQ ID NO: 85 | RTCKQAGTCPPD |
| SEQ ID NO: 86 | KGCKASGTCPPD |
| SEQ ID NO: 87 | RTCKQSGTCPPD |
| SEQ ID NO: 88 | RTCKVTGTCPAD |
| SEQ ID NO: 89 | RTCKATGTRPAD |
| SEQ ID NO: 90 | KTCKVAGTCPPD |
| SEQ ID NO: 91 | KTCKVAGTCPPD |
| SEQ ID NO: 92 | RTCKAAGTCPPD |
| SEQ ID NO: 93 | RTCKASGTCPPD |
| SEQ ID NO: 94 | STCKAAGTCPAD |
| SEQ ID NO: 95 | KTCKLSGTCPED |
| SEQ ID NO: 96 | KTCKQAGTCPED |
| SEQ ID NO: 97 | QTCKASGTCPPD |
| SEQ ID NO: 98 | QTCKAAGTCPSD |
| SEQ ID NO: 99 | QTCKLTGTCPPD |
| SEQ ID NO: 100 | KQCQLGADCPPD |
| SEQ ID NO: 101 | AKCQLSGNCLPD |
| SEQ ID NO: 102 | AKCQLSGDCLPD |
| SEQ ID NO: 103 | RHCALSGTCPDD |
| SEQ ID NO: 104 | KHCAGSGTCPED |
| SEQ ID NO: 105 | KTCLQGGDCIPD |
| SEQ ID NO: 106 | RSCLQGGDCIPD |
| SEQ ID NO: 107 | QTCKATGTCPPD |
| SEQ ID NO: 108 | KTCKQSGTCPPD |
| SEQ ID NO: 109 | KTCKQAGTCPSD |
| SEQ ID NO: 110 | STCKAAGTCPPD |
| SEQ ID NO: 111 | PTCKIAGNCPAD |
| SEQ ID NO: 112 | PACKISNTCPPD |
| SEQ ID NO: 113 | GCKQAGTCPPD |
| SEQ ID NO: 114 | GCKASNTCPPD |
| SEQ ID NO: 115 | GCKAAGTCPPD |
| SEQ ID NO: 116 | SCKAAGTCPPD |
| SEQ ID NO: 117 | TCKQSGTCPSD |
| SEQ ID NO: 118 | GCKASGTCPPD |
| SEQ ID NO: 119 | TCKQSGTCPPD |
| SEQ ID NO: 120 | TCKVTGTCPAD |
| SEQ ID NO: 121 | TCKATGTRPAD |
| SEQ ID NO: 122 | TCKVAGTCPPD |
| SEQ ID NO: 123 | TCKAAGTCPPD |

TABLE 1-continued

| List of L2 peptide immunogens (and variants thereof) | |
|---|---|
| SEQ ID NO: 124 | TCKASGTCPPD |
| SEQ ID NO: 125 | TCKAAGTCPAD |
| SEQ ID NO: 126 | TCKLSGTCPED |
| SEQ ID NO: 127 | TCKAAGTCPSD |
| SEQ ID NO: 128 | TCKLTGTCPPD |
| SEQ ID NO: 129 | QCQLGADCPPD |
| SEQ ID NO: 130 | KCQLSGNCLPD |
| SEQ ID NO: 131 | KCQLSGDCLPD |
| SEQ ID NO: 132 | HCALSGTCPDD |
| SEQ ID NO: 133 | HCAGSGTCPED |
| SEQ ID NO: 134 | TCLQGGDCIPD |
| SEQ ID NO: 135 | SCLQGGDCIPD |
| SEQ ID NO: 136 | TCKATGTCPPD |
| SEQ ID NO: 137 | TCKQAGTCPSD |
| SEQ ID NO: 138 | TCKIAGNCPAD |
| SEQ ID NO: 139 | ACKISNTCPPD |
| SEQ ID NO: 140 | CKQSGTCPDD |
| SEQ ID NO: 141 | CKASNTCPPD |
| SEQ ID NO: 142 | CKAAGTCPPD |
| SEQ ID NO: 143 | CKASGTCPPD |
| SEQ ID NO: 144 | CKQSGTCPPD |
| SEQ ID NO: 145 | CKVTGTCPAD |
| SEQ ID NO: 146 | CKATGTRPAD |
| SEQ ID NO: 147 | CKVAGTCPPD |
| SEQ ID NO: 148 | CKAAGTCPAD |
| SEQ ID NO: 149 | CKLSGTCPED |
| SEQ ID NO: 150 | CKAAGTCPSD |
| SEQ ID NO: 151 | CKLTGTCPPD |
| SEQ ID NO: 152 | CQLGADCPPD |
| SEQ ID NO: 153 | CQLSGNCLPD |
| SEQ ID NO: 154 | CQLSGDCLPD |
| SEQ ID NO: 155 | CALSGTCPDD |
| SEQ ID NO: 156 | CAGSGTCPED |
| SEQ ID NO: 157 | CLQGGDCIPD |
| SEQ ID NO: 158 | CKATGTCPPD |
| SEQ ID NO: 159 | CKQAGTCPSD |
| SEQ ID NO: 160 | CKIAGNCPAD |
| SEQ ID NO: 161 | CKISNTCPPD |

TABLE 1-continued

| List of L2 peptide immunogens (and variants thereof) | |
|---|---|
| SEQ ID NO: 162 | GCKQAGTCPP |
| SEQ ID NO: 163 | GCKASNTCPP |
| SEQ ID NO: 164 | GCKAAGTCPP |
| SEQ ID NO: 165 | SCKAAGTCPP |
| SEQ ID NO: 166 | TCKLAGTCPP |
| SEQ ID NO: 167 | GCKASGTCPP |
| SEQ ID NO: 168 | TCKQSGTCPP |
| SEQ ID NO: 169 | TCKVTGTCPA |
| SEQ ID NO: 170 | TCKATGTRPA |
| SEQ ID NO: 171 | TCKVAGTCPP |
| SEQ ID NO: 172 | TCKAAGTCPP |
| SEQ ID NO: 173 | TCKASGTCPP |
| SEQ ID NO: 174 | TCKAAGTCPA |
| SEQ ID NO: 175 | TCKLSGTCPE |
| SEQ ID NO: 176 | TCKAAGTCPS |
| SEQ ID NO: 177 | TCKLTGTCPP |
| SEQ ID NO: 178 | QCQLGADCPP |
| SEQ ID NO: 179 | KCQLSGNCLP |
| SEQ ID NO: 180 | KCQLSGDCLP |
| SEQ ID NO: 181 | HCALSGTCPD |
| SEQ ID NO: 182 | HCAGSGTCPE |
| SEQ ID NO: 183 | TCLQGGDCIP |
| SEQ ID NO: 184 | SCLQGGDCIP |
| SEQ ID NO: 185 | TCKATGTCPP |
| SEQ ID NO: 186 | TCKQAGTCPS |
| SEQ ID NO: 187 | TCKIAGNCPA |
| SEQ ID NO: 188 | ACKISNTCPP |
| SEQ ID NO: 189 | CKLAGTCPP |
| SEQ ID NO: 190 | CKASNTCPP |
| SEQ ID NO: 191 | CKAAGTCPP |
| SEQ ID NO: 192 | CKASGTCPP |
| SEQ ID NO: 193 | CKQSGTCPP |
| SEQ ID NO: 194 | CKVTGTCPA |
| SEQ ID NO: 195 | CKATGTRPA |
| SEQ ID NO: 196 | CKVAGTCPP |
| SEQ ID NO: 197 | CKAAGTCPA |
| SEQ ID NO: 198 | CKLSGTCPE |
| SEQ ID NO: 199 | CKAAGTCPS |
| SEQ ID NO: 200 | CKLTGTCPP |

TABLE 1-continued

List of L2 peptide immunogens (and variants thereof)

| | |
|---|---|
| SEQ ID NO: 201 | CQLGADCPP |
| SEQ ID NO: 202 | CQLSGNCLP |
| SEQ ID NO: 203 | CQLSGDCLP |
| SEQ ID NO: 204 | CALSGTCPD |
| SEQ ID NO: 205 | CAGSGTCPE |
| SEQ ID NO: 206 | CLQGGDCIP |
| SEQ ID NO: 207 | CKATGTCPP |
| SEQ ID NO: 208 | CKQAGTCPS |
| SEQ ID NO: 209 | CKIAGNCPA |
| SEQ ID NO: 210 | CKISNTCPP |
| SEQ ID NO: 211 | DVINKVEQTT |
| SEQ ID NO: 212 | DVINKVEQST |
| SEQ ID NO: 213 | DVINKVEQKT |
| SEQ ID NO: 214 | DVLNKVEQTT |
| SEQ ID NO: 215 | DVVNKVEQTT |
| SEQ ID NO: 216 | DVINKVESTT |
| SEQ ID NO: 217 | DVINKVEQNT |
| SEQ ID NO: 218 | DVVPKVEGDT |
| SEQ ID NO: 219 | DVIPKVEGDT |
| SEQ ID NO: 220 | DIIPRVEQNT |
| SEQ ID NO: 221 | DIIPRLEQNT |
| SEQ ID NO: 222 | DIIPRVEQDT |
| SEQ ID NO: 223 | DVIPKVEGTT |
| SEQ ID NO: 224 | DIIPKVEQKT |
| SEQ ID NO: 225 | DVIPKVEGST |
| SEQ ID NO: 226 | DIIPKVEHNT |
| SEQ ID NO: 227 | DVIPKVEQNT |
| SEQ ID NO: 228 | DVIPKVEHNT |
| SEQ ID NO: 229 | DVINKVEHTT |
| SEQ ID NO: 230 | DVRNKVEGTT |
| SEQ ID NO: 231 | DVKNKVEADT |
| SEQ ID NO: 232 | DVKNKVEANT |
| SEQ ID NO: 233 | DVKNKVENNT |
| SEQ ID NO: 234 | DVKNKVEQTT |
| SEQ ID NO: 235 | DVKNKFENST |
| SEQ ID NO: 236 | DVQNKFEGNT |
| SEQ ID NO: 237 | DIQNKIEQTT |
| SEQ ID NO: 238 | DVIKRYEQTT |
| SEQ ID NO: 239 | VINKVEQTT |
| SEQ ID NO: 240 | VINKVEQST |
| SEQ ID NO: 241 | VINKVEQKT |
| SEQ ID NO: 242 | VLNKVEQTT |
| SEQ ID NO: 243 | VVNKVEQTT |
| SEQ ID NO: 244 | VINKVESTT |
| SEQ ID NO: 245 | VINKVEQNT |
| SEQ ID NO: 246 | VVPKVEGDT |
| SEQ ID NO: 247 | VIPKVEGDT |
| SEQ ID NO: 248 | IIPRVEQNT |
| SEQ ID NO: 249 | IIPRLEQNT |
| SEQ ID NO: 250 | IIPRVEQDT |
| SEQ ID NO: 251 | VIPKVEGTT |
| SEQ ID NO: 252 | IIPKVEQKT |
| SEQ ID NO: 253 | VIPKVEGST |
| SEQ ID NO: 254 | IIPKVEHNT |
| SEQ ID NO: 255 | VIPKVEQNT |
| SEQ ID NO: 256 | VIPKVEHNT |
| SEQ ID NO: 257 | VINKVEHTT |
| SEQ ID NO: 258 | VRNKVEGTT |
| SEQ ID NO: 259 | VKNKVEADT |
| SEQ ID NO: 260 | VKNKVEANT |
| SEQ ID NO: 261 | VKNKVENNT |
| SEQ ID NO: 262 | VKNKVEQTT |
| SEQ ID NO: 263 | VKNKFENST |
| SEQ ID NO: 264 | VQNKFEGNT |
| SEQ ID NO: 265 | IQNKIEQTT |
| SEQ ID NO: 266 | VIKRYEQTT |
| SEQ ID NO: 267 | INKVEQTT |
| SEQ ID NO: 268 | INKVEQTT |
| SEQ ID NO: 269 | INKVEQKT |
| SEQ ID NO: 270 | LNKVEQTT |
| SEQ ID NO: 271 | VNKVEQTT |
| SEQ ID NO: 272 | INKVESTT |
| SEQ ID NO: 273 | INKVEQNT |
| SEQ ID NO: 274 | VPKVEGDT |
| SEQ ID NO: 275 | IPKVEGDT |
| SEQ ID NO: 276 | IPRVEQNT |
| SEQ ID NO: 277 | IPRLEQNT |

TABLE 1-continued

List of L2 peptide immunogens (and variants thereof)

| SEQ ID NO: 278 | IPRVEQDT |
| SEQ ID NO: 279 | IPKVEGTT |
| SEQ ID NO: 280 | IPKVEHKT |
| SEQ ID NO: 281 | IPKVEGST |
| SEQ ID NO: 282 | IPKVEHNT |
| SEQ ID NO: 283 | IPKVEQNT |
| SEQ ID NO: 284 | INKVEHTT |
| SEQ ID NO: 285 | RNKVEGTT |
| SEQ ID NO: 286 | KNKVEADT |
| SEQ ID NO: 287 | KNKVEANT |
| SEQ ID NO: 288 | KNKVENNT |
| SEQ ID NO: 289 | KNKVEQTT |
| SEQ ID NO: 290 | KNKFENST |
| SEQ ID NO: 291 | QNKFEGNT |
| SEQ ID NO: 292 | QNKIEQTT |
| SEQ ID NO: 293 | IKRYEQTT |
| SEQ ID NO: 294 | TGYIPLQTR |
| SEQ ID NO: 295 | TGYVPLGST |
| SEQ ID NO: 296 | TGYVPLGNT |
| SEQ ID NO: 297 | TGYVPLSTG |
| SEQ ID NO: 298 | TGYIPLQST |
| SEQ ID NO: 299 | TGYVPVGST |
| SEQ ID NO: 300 | TGYVPLQTS |
| SEQ ID NO: 301 | TGYVPLTTG |
| SEQ ID NO: 302 | RGCKQXGTCPPDVINKVEQ |
| SEQ ID NO: 303 | RGCKAXNTCPPDVINKVEQ |
| SEQ ID NO: 304 | RGCKAXGTCPPDVINKVEQ |
| SEQ ID NO: 305 | QSCKAXGTCPPDVLNKVEQ |
| SEQ ID NO: 306 | QSCKAXGTCPPDVVNKVEQ |
| SEQ ID NO: 307 | QTCKQXGTCPPDVINKVEQ |
| SEQ ID NO: 308 | QTCKQXGTCPPDVVNKVEQ |
| SEQ ID NO: 309 | RTCKQXGTCPPDVINKVES |
| SEQ ID NO: 310 | RTCKQXGTCPPDVINKVEQ |
| SEQ ID NO: 311 | KGCKAXGTCPPDVINKVEQ |
| SEQ ID NO: 312 | RTCKQXGTCPPDVVPKVEG |
| SEQ ID NO: 313 | RTCKQXGTCPPDVIPKVEG |
| SEQ ID NO: 314 | RTCKVXGTCPADVVPKVEG |
| SEQ ID NO: 315 | RTCKAXGTRPADVIPKVEG |
| SEQ ID NO: 316 | STCKAXGTCPPDVIPKLEG |
| SEQ ID NO: 317 | RTCKQXGTCPPDIIPRLEQ |
| SEQ ID NO: 318 | RTCKQXGTCPPDIIPRVEQ |
| SEQ ID NO: 319 | KTCKVXGTCPPDVIPKVEG |
| SEQ ID NO: 320 | KTCKAXGTCPPDVIPKVEG |
| SEQ ID NO: 321 | STCKAXGTCPPDVIPKVEG |
| SEQ ID NO: 322 | RTCKAXGTCPPDVIPKVEG |
| SEQ ID NO: 323 | STCKAXGTCPADVIPKVEG |
| SEQ ID NO: 324 | KTCKLXGTCPEDVINKVEQ |
| SEQ ID NO: 325 | KTCKQXGTCPPDIIPKIEG |
| SEQ ID NO: 326 | KTCKQXGTCPPDIVPKVEG |
| SEQ ID NO: 327 | STCKQXGTCPPDIIPRVEQ |
| SEQ ID NO: 328 | KTCKQXGTCPPDVIPKVEG |
| SEQ ID NO: 329 | QTCKAXGTCPSDIIPKVEH |
| SEQ ID NO: 330 | QTCKAXGTCPPDVIPKVEQ |
| SEQ ID NO: 331 | QTCKLXGTCPPDVIPKVEH |
| SEQ ID NO: 332 | QTCKAXGTCPSDVINKVEH |
| SEQ ID NO: 333 | KQCQLXADCPPDVRNKVEG |
| SEQ ID NO: 334 | AKCQLXGNCLPDVKNKVEA |
| SEQ ID NO: 335 | AKCQLXGDCLPDVKNKVEA |
| SEQ ID NO: 336 | RHCALXGTCPDDVKNKVEN |
| SEQ ID NO: 337 | KHCAGXGTCPEDVKNKVEQ |
| SEQ ID NO: 338 | KTCLQXGDCIPDVKNKFEN |
| SEQ ID NO: 339 | RSCLQXGDCIPDVQNKFEG |
| SEQ ID NO: 340 | QTCKAXGTCPPDVIPKVEG |
| SEQ ID NO: 341 | KTCKQXGTCPPDVVPKVEG |
| SEQ ID NO: 342 | RTCKQXGTCPPDVINKVEG |
| SEQ ID NO: 343 | KTCKQXGTCPSDVINKVEG |
| SEQ ID NO: 344 | KTCKLXGTCPEDVVNKIEQ |
| SEQ ID NO: 345 | RTCKQXGTCPPDVVDKVEG |
| SEQ ID NO: 346 | STCKAXGTCPPDVVNKVEG |
| SEQ ID NO: 347 | PTCKIXGNCPADIQNKFEN |
| SEQ ID NO: 348 | PACKIXNTCPPDIINKYEN |
| SEQ ID NO: 349 | RGCKQXGTCPPD |
| SEQ ID NO: 350 | RGCKAXNTCPPD |
| SEQ ID NO: 351 | RGCKAXGTCPPD |
| SEQ ID NO: 352 | QSCKAXGTCPPD |
| SEQ ID NO: 353 | QTCKQXGTCPPD |
| SEQ ID NO: 354 | RTCKQXGTCPPD |

TABLE 1-continued

| List of L2 peptide immunogens (and variants thereof) | |
|---|---|
| SEQ ID NO: 355 | KGCKAXGTCPPD |
| SEQ ID NO: 356 | PTCKAXGTCPPD |
| SEQ ID NO: 357 | RTCKVXGTCPAD |
| SEQ ID NO: 358 | RTCKAXGTRPAD |
| SEQ ID NO: 359 | KTCKVXGTCPPD |
| SEQ ID NO: 360 | KTCKAXGTCPPD |
| SEQ ID NO: 361 | RTCKAXGTCPPD |
| SEQ ID NO: 362 | STCKAXGTRPPD |
| SEQ ID NO: 363 | STCKAXGTCPAD |
| SEQ ID NO: 364 | KTCKLXGTCPED |
| SEQ ID NO: 365 | ATCKQXGTCPPD |
| SEQ ID NO: 366 | STCKQXGTCPPD |
| SEQ ID NO: 367 | QTCKAXGTCPSD |
| SEQ ID NO: 368 | QTCKLXGTCPPD |
| SEQ ID NO: 369 | KQCQLXADCPPD |
| SEQ ID NO: 370 | AKCQLXGNCLPD |
| SEQ ID NO: 371 | AKCQLXGDCLPD |
| SEQ ID NO: 372 | RHCALXGTCPDD |
| SEQ ID NO: 373 | KHCAGXGTCPED |
| SEQ ID NO: 374 | KTCLQXGDCIPD |
| SEQ ID NO: 375 | RSCLQXGDCIPD |
| SEQ ID NO: 376 | QTCKAXGTCPPD |
| SEQ ID NO: 377 | KTCKQXGTCPED |
| SEQ ID NO: 378 | KTCKQXGTCPSD |
| SEQ ID NO: 379 | STCKAXGTCPPD |
| SEQ ID NO: 380 | PTCKIXGNCPAD |
| SEQ ID NO: 381 | PACKIXNTCPPD |
| SEQ ID NO: 382 | GCKQXGTCPPD |
| SEQ ID NO: 383 | GCKAXNTCPPD |
| SEQ ID NO: 384 | ACKAXGTCPPD |
| SEQ ID NO: 385 | SCKAXGTCPPD |
| SEQ ID NO: 386 | KCKAXGTCIPD |
| SEQ ID NO: 387 | GCKAXGTCPPD |
| SEQ ID NO: 388 | KCKAXGTCPPD |
| SEQ ID NO: 389 | TCKVXGTCPAD |
| SEQ ID NO: 390 | TCKAXGTRPAD |
| SEQ ID NO: 391 | TCKVXGTCPPD |
| SEQ ID NO: 392 | SCKLXGTCPPD |
| SEQ ID NO: 393 | SCKQXGTCPSD |
| SEQ ID NO: 394 | TCKAXGTCPAD |
| SEQ ID NO: 395 | TCKLXGTCPED |
| SEQ ID NO: 396 | TCKAXGTCPSD |
| SEQ ID NO: 397 | TCKLXGTCPPD |
| SEQ ID NO: 398 | QCQLXADCPPD |
| SEQ ID NO: 399 | KCQLXGNCLPD |
| SEQ ID NO: 400 | KCQLXGDCLPD |
| SEQ ID NO: 401 | HCALXGTCPDD |
| SEQ ID NO: 402 | HCAGXGTCPED |
| SEQ ID NO: 403 | TCLQXGDCIPD |
| SEQ ID NO: 404 | SCLQXGDCIPD |
| SEQ ID NO: 405 | TCKAXGTCPPD |
| SEQ ID NO: 406 | TCKQXGTCPSD |
| SEQ ID NO: 407 | TCKIXGNCPAD |
| SEQ ID NO: 408 | ACKIXNTCPPD |
| SEQ ID NO: 409 | CKQXGTCPDD |
| SEQ ID NO: 410 | CKAXNTCPPD |
| SEQ ID NO: 411 | CLAXGTCPAD |
| SEQ ID NO: 412 | CLAXGTCPPD |
| SEQ ID NO: 413 | CKLXGTCPAD |
| SEQ ID NO: 414 | CKVXGTCPAD |
| SEQ ID NO: 415 | CKAXGTRPAD |
| SEQ ID NO: 416 | CKVXGTCPPD |
| SEQ ID NO: 417 | CKAXGTCPAD |
| SEQ ID NO: 418 | CKLXGTCPED |
| SEQ ID NO: 419 | CKAXGTCPSD |
| SEQ ID NO: 420 | CKLXGTCPPD |
| SEQ ID NO: 421 | CQLXADCPPD |
| SEQ ID NO: 422 | CQLXGNCLPD |
| SEQ ID NO: 423 | CQLXGDCLPD |
| SEQ ID NO: 424 | CALXGTCPDD |
| SEQ ID NO: 425 | CAGXGTCPED |
| SEQ ID NO: 426 | CLQXGDCIPD |
| SEQ ID NO: 427 | CKAXGTCPPD |
| SEQ ID NO: 428 | CKQXGTCPSD |
| SEQ ID NO: 429 | CKIXGNCPAD |
| SEQ ID NO: 430 | CKIXNTCPPD |
| SEQ ID NO: 486 | KTCKQSGTCPSDVVNKVEG |

TABLE 1-continued

List of L2 peptide immunogens (and variants thereof)

SEQ ID NO: 487  QTCKAAGTCPSDVIPKIEH

SEQ ID NO: 488  KTCKQSGTCPPDVIDKVEG

SEQ ID NO: 489  STCKAAGTCPPDVIPKVKG

SEQ ID NO: 490  KTCKQSGTCPSD

SEQ ID NO: 491 ((SEQ ID NO: 2)x3 +
(SEQ ID NO: 487)x3 + (SEQ ID NO: 77)x3 with a
tripeptide (GGP) linker):
KTCKQAGTCPPDIIPKVEGGGPKTCKQAGTCPPDIIPKVEGGGPKTCK
QAGTCPPDIIPKVEGGGPQTCKAAGTCPSDVIPKIEHGGPQTCKAAGT
CPSDVIPKIEHGGPQTCKAAGTCPSDVIPKIEHGGPSTCKAAGTCPPD
VVNKVEGGGPSTCKAAGTCPPDVVNKVEGGGPSTCKAAGTCPPDVVNK
VEG SEQ ID NO: 492 ((SEQ ID NO: 2) + (SEQ ID
NO: 487) + (SEQ ID NO: 77))x3 with a tripeptide
(GGP) linker
KTCKQAGTCPPDIIPKVEGGGPQTCKAAGTCPSDVIPKIEHGGPSTCK
AAGTCPPDVVNKVEGGGPKTCKQAGTCPPDIIPKVEGGGPQTCKAAGT
CPSDVIPKIEHGGPSTCKAAGTCPPDVVNKVEGGGPKTCKQAGTCPPD
IIPKVEGGGPQTCKAAGTCPSDVIPKIEHGGPSTCKAAGTCPPDVVNK
VEG

***X = Gly (G) or Ala (A)

TABLE 2

List of thioredoxin variants

SEQ ID NO: 493 (variant thiorexodin polypeptide
from hyperthermophile archaebacterium *Pyrococcus
furiosus*)
MIIEYDGEIDFTKGRVVLWFSIPGCGPCRLVERFMTELSEYFEDIQIV
HINAGKWKNIVDKFNILNVPTLVYLKDGREVGRQNLIRSKEEILKKLK
ELQE

TABLE 2-continued

List of thioredoxin variants

SEQ ID NO: 494 (variant thiorexodin polypeptide
from hyperthermophile archaebacterium
*Thermococcus kodakarensis*)
MIVEYDENVDFTKGKAVLWFSIPGCGPCRLVEAFMKELSEEFGEIAIV
HVNAEKWSGLVEGFRILNVPTLVYLKDGKEVARQNLIRGKGEVLIKFE
EPREL SEQ ID NO: 495 (variant thiorexodin polypeptide
from hyperthermophile archaebacterium
*Thermococcus onnurineus*)
MIREFDGDFGKVERAKYALLWFSSPGCGPCRMIEPFMHELSEEYKEVE
FWEVDVEKHLPLAEKFDVMNVPTLIYLKEGNEIARQNLVRKKEEVEEK
LMMLLGSDS SEQ ID NO: 496 (variant of thiorexodin poly-
peptide from hyperthermophile archaebacterium
*Thermococcus sibiricus*)
MIHEYDGKIDFNRGKVVLWFSIQGCGPCRLVESFMEEVSEEFSEIRFI
HVGAEKWSNIVKRFEVLNVPTLVYLKDGKEVARQNLIRSKEEVLAKIE
ELHE SEQ ID NO: 497 (Dimer of *Escherichia coli*
thioredoxin variants)
MSDKIIHLTDDSFDTDVLKADGAILVDFWAEWCGPCKMIAPILDEIAD
EYQGKLTVAKLNIDQNPGTAPKYGIRGIPTLLLFKNGEVAATKVGALS
KGQLKEFLDANLAGGGSEGGGSEGGGSEGGGSEGGGSEGGGSEGGGM
SDKIIHLTDDSFDTDVLKADGAILVDFWAEWCGPCKMIAPILDEIAD
EYQGKLTVAKLNIDQNPGTAPKYGIRGIPTLLLFKNGEVAATKVGALS
KGQLKEFLDANLA SEQ ID NO: 498 (Trimer of *Escherichia coli*
thioredoxin variants)
MSDKIIHLTDDSFDTDVLKADGAILVDFWAEWCGPCKMIAPILDEIAD
EYQGKLTVAKLNIDQNPGTAPKYGIRGIPTLLLFKNGEVAATKVGALS
KGQLKEFLDANLAGGGSEGGGSEGGGSEGGGSEGGGSEGGGSEGGGM
SDKIIHLTDDSFDTDVLKADGAILVDFWAEWCGPCKMIAPILDEIAD
EYQGKLTVAKLNIDQNPGTAPKYGIRGIPTLLLFKNGEVAATKVGALS
KGQLKEFLDANLAGGGSEGGGSEGGGSEGGGSEGGGSEGGGSEGGGM
SDKIIHLTDDSFDTDVLKADGAILVDFWAEWCLSCKMIAPILDEIADE
YQGKLTVAKLNIDQNPGTAPKYGIRGIPTLLLFKNGEVAATKVGALSK
GQLKEFLDANLA

---

The invention claimed is:

1. An immunogenic fusion polypeptide comprising:
   (a) a scaffold polypeptide selected from the group consisting of thioredoxin polypeptides, and thioredoxin polypeptides from thermophile bacteria; and
   (b) a L2 peptide as set forth in one of SEQ ID NOs: 1-15, 20-22 and 31-479, wherein the scaffold polypeptide constrains the structure of the L2 peptide.

2. The immunogenic fusion polypeptide of claim 1, wherein the scaffold polypeptide is a thioredoxin polypeptide selected from the group consisting of:

(a) a polypeptide as set forth in one of SEQ ID No: 24, SEQ ID No: 25, SEQ ID No: 26, SEQ ID No: 27, Of and SEQ ID No: 28; and (b) a variant polypeptide that is at least 70% identical to one of the sequences set forth in SEQ ID No: 24, SEQ ID No: 25, SEQ ID No: 26, SEQ ID No: 27, and SEQ ID No: 28.

3. The immunogenic fusion polypeptide according to claim 1, wherein the L2 peptide is selected from the group consisting of SEQ ID NO: 2, 3, 4, 5, 6, 7, 8, 9, 10, 11, 12, 13, 14, 15, 31 and 32.

4. The immunogenic fusion polypeptide according to claim 1, wherein the L2 peptide has the sequence as shown in SEQ ID NO:2.

5. The immunogenic fusion polypeptide according to claim 1, wherein the immunogenic polypeptide comprises a multimer of the L2 peptide.

6. The immunogenic fusion polypeptide according to claim 1, wherein the immunogenic polypeptide has the sequence shown in SEQ ID NO: 29 or 30.

7. A vaccine comprising the immunogenic fusion polypeptide according to claim 1.

8. A method of immunizing a subject against infection with human papillomavirus (HPV) comprising administering a vaccine comprising the immunogenic fusion polypeptide of claim 1.

9. A method for producing an antibody against the immunogenic fusion polypeptide of claim 1, comprising the steps:

(a) providing the immunogenic fusion polypeptide;

(b) immunizing a host with the immunogenic fusion polypeptide; and (c) harvesting the resulting antibody against the immunogenic fusion polypeptide.

10. The method of claim 9, wherein the antibody is against human papillomavirus (HPV) genotypes 52, 2, 27, 57 and/or 11.

11. The method of claim 9, wherein the antibody is polyclonal or monoclonal.

12. The immunogenic fusion polypeptide of claim 1, wherein:

(a) the scaffold polypeptide is selected from the group consisting of SEQ ID Nos: 24, 25, 26, 27, 28, and 493-496; and (b) the L2 peptide is selected from the group consisting of SEQ ID Nos: 2, 3, 4, 5, 6, 7, 8, 9, 10, 11, 12, 13, 14, 15, 31 and 32.

13. The immunogenic fusion polypeptide of claim 1, wherein the L2 peptide is inserted within the sequence of a thioredoxin polypeptide.

14. An immunogenic fusion polypeptide comprising:

(a) a scaffold polypeptide which is a thioredoxin polypeptide;

(b) an L2 peptide as set forth in one of SEQ ID NOs: 1-15, 20-22 and 31-479, wherein the scaffold polypeptide constrains the structure of the L2 peptide; and wherein the thioredoxin polypeptide comprises a display site having the sequence of CGPC (SEQ ID NO: 23), and wherein the L2 peptide is inserted between (a) C and G of the display site, (b) G and P of the display site, or (c) P and C of the display site.

15. The immunogenic fusion polypeptide of claim 1, wherein the immunogenic polypeptide comprises more than one L2 peptides having the same sequence or at least 70% sequence identity.

16. An immunogenic fusion polypeptide comprising:

(a) a scaffold polypeptide which is a thioredoxin polypeptide from a thermophile bacterium; and (b) an L2 peptide as set forth in one of SEQ ID NOs: 1-15, 20-22 and 31-479, wherein the scaffold polypeptide constrains the structure of the L2 peptide.

* * * * *